(12) United States Patent
Mao et al.

(10) Patent No.: US 8,778,627 B2
(45) Date of Patent: Jul. 15, 2014

(54) ENZYME SUBSTRATE COMPRISING A FUNCTIONAL DYE AND ASSOCIATED TECHNOLOGY AND METHODS

(75) Inventors: Fei Mao, Fremont, CA (US); Hui Cen, Oakland, CA (US); Wai-Yee Leung, San Ramon, CA (US)

(73) Assignee: Biotium, Inc., Hayward, CA (US)

( * ) Notice: Subject to any disclaimer, the term of this patent is extended or adjusted under 35 U.S.C. 154(b) by 1 day.

(21) Appl. No.: 13/326,009

(22) Filed: Dec. 14, 2011

(65) Prior Publication Data

US 2012/0115129 A1 May 10, 2012

Related U.S. Application Data

(63) Continuation of application No. 12/095,322, filed as application No. PCT/US2006/061167 on Nov. 21, 2006, now Pat. No. 8,092,784.

(51) Int. Cl.
*C12Q 1/40* (2006.01)
*C12Q 1/48* (2006.01)
*C12Q 1/37* (2006.01)
*C07D 263/60* (2006.01)

(52) U.S. Cl.
CPC ...... *C12Q 1/37* (2013.01); *C12Q 1/485* (2013.01); *C07D 263/60* (2013.01); *C12Q 1/48* (2013.01)
USPC .................. 435/23; 435/15; 435/24; 548/217

(58) Field of Classification Search
CPC .................................................... C07D 263/60
USPC .............. 424/9.6; 435/4, 23, 15, 24; 530/330; 548/217
See application file for complete search history.

(56) References Cited

U.S. PATENT DOCUMENTS

| | | |
|---|---|---|
| 4,557,862 A | 12/1985 | Mangel et al. |
| 4,694,070 A | 9/1987 | Mitchell et al. |
| 4,801,534 A | 1/1989 | Mitchell et al. |
| 5,030,721 A | 7/1991 | Kasai et al. |
| 5,208,148 A | 5/1993 | Haugland et al. |
| 5,321,130 A | 6/1994 | Yue et al. |
| 5,403,928 A | 4/1995 | Arrhenuis |
| 5,436,134 A | 7/1995 | Haugland et al. |
| 5,437,980 A | 8/1995 | Haugland |
| 5,534,416 A | 7/1996 | Millard et al. |
| 5,576,424 A | 11/1996 | Mao et al. |
| 5,582,977 A | 12/1996 | Yue et al. |
| 5,641,629 A | 6/1997 | Pitner et al. |
| 5,741,657 A | 4/1998 | Tsien et al. |
| 5,863,753 A | 1/1999 | Haugland et al. |
| 5,955,604 A | 9/1999 | Tsien et al. |
| 6,031,094 A | 2/2000 | Tsien et al. |
| 6,348,317 B1 | 2/2002 | Thompson et al. |
| 6,750,024 B2 | 6/2004 | Lee et al. |
| 6,956,032 B1 | 10/2005 | Waggoner |
| 6,979,530 B2 | 12/2005 | Yan et al. |
| 7,446,202 B2 | 11/2008 | Dallwig et al. |
| 7,655,409 B2 | 2/2010 | Dallwig et al. |
| 8,092,784 B2 | 1/2012 | Mao et al. |
| 2003/0044353 A1 | 3/2003 | Weissleder et al. |
| 2003/0215863 A1 | 11/2003 | Chow et al. |
| 2005/0118669 A1 | 6/2005 | Tsien et al. |
| 2005/0227309 A1 | 10/2005 | Corry et al. |
| 2005/0261176 A1 | 11/2005 | Glick et al. |
| 2005/0272053 A1 | 12/2005 | Mao et al. |

FOREIGN PATENT DOCUMENTS

| | | |
|---|---|---|
| BE | 668894 A | 12/1965 |
| DE | 929080 C | 8/1955 |

OTHER PUBLICATIONS

Biotium, Inc. Catalog. Fluorescent Probes and Related Biochemical Reagents for Life Science, 2005-2006.
Birrell, et al. Allosteric interactions within subsites of a monomeric enzyme: kinetics of fluorogenic substrates of PI-specific phospholipase. Biophys J. May 2003;84(5):3264-75.
Brooker et al. Color and Constitution. V. 1 The Absorption of Unsymmetrical Cyanines. Resonance as a Basis for a Classification of Dyes. J. Am. Chem. Soc. 1942;64:199-210.
Cai et al. Design and synthesis of rhodamine 110 derivative and caspase-3 substrate for enzyme and cell-based fluorescent assay. Bioorg Med Chem Lett. Jan. 8, 2001;11(1):39-42.
Diaz, et al. Molecular recognition of taxol by microtubules. Kinetics and thermodynamics of binding of fluorescent taxol derivatives to an exposed site. J Biol Chem. Aug. 25, 2000;275(34):26265-76.
Fernandez-Santana et al. Conjugation of 5-azido-3-oxapentyl glycosides with thiolated proteins through the use of thiophilic derivatives. Glycoconj J. Jun. 1998;15(6):549-53.
Foerster, T. Intermolecular energy transfer and fluorescence. Ann. Phys. 1948; 2:55-75. (Abstract only).
Gao et al. Novel fluorogenic substrates for imaging beta-lactamase gene expression. J Am Chem Soc. Sep. 17, 2003;125(37):11146-7.
Gaugain et al. DNA bifunctional intercalators. I. Synthesis and conformational properties of an ethidium homodimer and of an acridine ethidium heterodimer. Biochemistry. Nov. 28, 1978;17(24):5071-8.

(Continued)

*Primary Examiner* — Susan Hanley
(74) *Attorney, Agent, or Firm* — Wilson Sonsini Goodrich & Rosati

(57) ABSTRACT

Enzyme substrates and associated technology of the present invention are provided. An enzyme substrate of the invention may comprise a biologically functional fluorescent dye and an enzyme-specific substrate moiety attached in such a way that the functionality of the functional dye is diminished. An enzymatic reaction may cleave at least a portion of the substrate moiety from the enzyme substrate to provide a more functional product dye. This product dye may be nonfluorescent or weakly fluorescent, in general, and relatively fluorescent, in a particular condition, such as when bound to a partner biological molecule or an assembly of partner biological molecules. An enzyme substrate of the present invention may thus be useful in fluorescence detection, and/or in any of a variety of useful applications, such as the detection of enzymatic activity in a cell-free system or in a living cell, the screening of drugs, or the diagnosis of disease.

9 Claims, 30 Drawing Sheets

(56) References Cited

OTHER PUBLICATIONS

Hassner, et al. Charge-shift probes of membrane potential. Synthesis. J. Org. Chem. 1984;49:2546-2551. (1984).

International search report and written opinion dated Jun. 13, 2008 for PCT Application No. US2006/061167.

Kirkpatrick, P. Use of near-infrared spectroscopy in the adult. Philos Trans R Soc Lond B Biol Sci. Jun. 29, 1997;352(1354):701-5.

Kren et al. Glycosylation of silybin. J. Chem. Soc. Perkin Trans. 1997;1:2467-2474.

Lowe, et al. Apoptosis in cancer. Carcinogenesis. 2000; 21(3):485-495.

Nakamura, et al. Tyrosine phosphorylation of p130Cas is involved in actin organization in osteoclasts. J. Biol. Chem. 1998; 273:11144-11149.

Paschalidou, et al. Highly sensitive intramolecularly quenched fluorogenic substrates for renin based on the combination of L-2-amino-3-(7-methoxy-4-coumaryl)propionic acid with 2,4-dinitrophenyl groups at various positions. Biochem J. Sep. 15, 2004;382(Pt 3):1031-8.

Reed, et al. Drug discovery opportunities from apoptosis research. Curr Opin Biotechnol. Dec. 2000;11(6):586-92.

Rotman et al. Fluorogenic substrates for beta-D-galactosidases and phosphatases derived from flurescein (3,6-dihydroxyfluoran) and its monomethylether. Proc Natl Acad Sci U S A. Jul. 1963;50:1-6.

Rukavishnikov, et al. Synthesis of a new fluorogenic substrate for the continuous assay of mammalian phosphoinositide-specific phospholipase. Bioorg Med Chem Lett. Apr. 19, 1999;9(8):1133-6.

Scheigetz et al. Synthesis of fluorescein phosphates and sulfates. Organic Prep. Proc. Int. 1997; 29(5): 561-568.

Stryer, et al. Energy transfer: a spectroscopic ruler. Proc Natl Acad Sci U S A. Aug. 1967;58(2):719-26.

Taliani, et al. A continuous assay of hepatitis C virus protease based on resonance energy transfer depsipeptide substrates. Anal Biochem. Aug. 15, 1996;240(1):60-7.

Tromberg, et al. Non-invasive measurements of breast tissue optical properties using frequency-domain photon migration. Philos Trans R Soc Lond B Biol Sci. Jun. 29, 1997;352(1354):661-8.

Wang, et al. Design and synthesis of new fluorogenic HIV protease substrates based on resonance energy transfer. Tetrahedon Lett. 1990;31:6493-6496.

Watkins, et al. Effect of changing the quaternizing group on the trypanocidal activity of dimidium bromide. Nature. 1952; 169:506.

Watkins, et al. Trypanocides of the phenanthridine series. Part I. The effect of changing the quaternary grouping in dimidium bromide. J. Chem. Soc. 1952;3059-3064.

Wellington, et al. Caspases and neurodegeneration: on the cutting edge of new therapeutic approaches. Clin Genet. Jan. 2000;57(1):1-10.

Zaikova, et al. Synthesis of fluorogenic substrates for continuous assay of phosphatidylinositol-specific phospholipase C. Bioconjug Chem. Mar.-Apr. 2001;12(2):307-13.

Zhang, et al. N-Ac-DEVD-N'-(Polyfluorobenzoyl)-R110: novel cell-permeable fluorogenic caspase substrates for the detection of caspase activity and apoptosis. Bioconjug Chem. Mar.-Apr. 2003;14(2):458-63.

Zlokarnik, et al. Quantitation of transcription and clonal selection of single living cells with beta-lactamase as reporter. Science. Jan. 2, 1998;279(5347):84-8.

U.S. Appl. No. 14/051,187, filed Oct. 10, 2013, Mao et al.

U.S. Appl. No. 13/891,406, filed May 10, 2013, Mao et al.

Kojima, et al. A new and highly sensitive fluorescence assay for collagenase-like peptidase activity. Analytical Biochemistry. 1979; 100:43-50.

Leytus, et al. New class of sensitive and selective fluorogenic substrates for serine proteinases. Amino acid and dipeptide derivatives of rhodamine. Biochem J. 1983 Nov. 1;215(2):253-60.

Leytus, et al. Rhodamine-based compounds as fluorogenic substrates for serine proteinases. Biochem J. Feb. 1, 1983;209(2):299-307.

Liu, et al. Fluorescent molecular probes V: a sensitive caspase-3 substrate for fluorometric assays. Bioorg Med Chem Lett. Nov. 15, 1999;9(22):3231-6.

Scheper, et al. Two new fluorogenic substrates for the detection of Penicillin-G-acylase activity. Anal. Chim. Acta. 1986; 182:203-206.

Isacsson, et al. Solid-phase synthesis of asymmetric cyanine dyes. Tetrahedron Letters. 2001; 42:3207-3210.

Svanvik, et al. Light-up probes: thiazole orange-conjugated peptide nucleic acid for detection of target nucleic acid in homogeneous solution. Anal Biochem. May 15, 2000;281(1):26-35.

Tok, et al. Aminoglycoside hybrids as potent RNA antagonists. Tetrahedron. 1999; 55:5741-5758.

Table 2. Enzyme Substrates Associated with Structure 1 and Associated Information

| Substrate No. | $R_1$ | $R_2$ | $R_3$ | Target Enzyme | Cellular Localization Site of Enzyme Substrate | Cellular Site of DYE | $\lambda_{abs}/\lambda_{em}$ (nm / nm) |
|---|---|---|---|---|---|---|---|
| 1 | Z-DEVD-, where DEVD = SEQ ID NO: 1 | H | $CH_3(CH_2)_{15}$- | caspase-3 | cytoplasm | DNA / RNA | 518 / 605 |
| 2 | Z-VEID-, where VEID = SEQ ID NO: 2 | H | $CH_3(CH_2)_{15}$- | caspase-6 | cytoplasm | DNA / RNA | 518 / 605 |
| 3 | Z-IPR- | H | $CH_3(CH_2)_{15}$- | trypsin | cytoplasm / lysosome | DNA / RNA | 518 / 605 |
| 4 | Ac-F- | Ac-F- | $CH_3CH_2$- | chymotrypsin | cytoplasm / mitochondrion | DNA / RNA | 518 / 605 |
| 5 | Z-AA- | H | $CH_3CH_2$- | elastase | cytoplasm / mitochondrion | DNA / RNA | 518 / 605 |
| 6 | Z-AA- | Z-AA- | $CH_3CH_2$- | elastase | cytoplasm / mitochondrion | DNA / RNA | 518 / 605 |
| 7 | Z-FR- | Z-FR- | $CH_3(CH_2)_{17}$- | cathepsins B and L | cytoplasm / membrane | DNA / RNA | 518 / 605 |
| 8 | Z-LEED-, where LEED = SEQ ID NO: 3 | H | $CH_3CH_2$- | caspase-13 | (membrane-impermeable) | DNA / RNA | 518 / 605 |

*FIG. 10*

Table 3. Enzyme Substrates Associated with Structure 2 and Associated Information

| Substrate No. | W | L | B | Target Enzyme | Cellular Site of Enzyme Substrate | Cellular Site of DYE or DYE-B' | $\lambda_{abs} / \lambda_{em}$ (nm / nm) |
|---|---|---|---|---|---|---|---|
| 9 | NH | -(CH$_2$)-3- | Z-DEVD·, where DEVD = SEQ ID NO: 1 | caspase-3 | (membrane-impermeable) | DNA / RNA | 518 / 605 |
| 10 | NH | -(CH$_2$)-3- | Z-VEID·, where VEID = SEQ ID NO: 2 | caspase-6 | (membrane-impermeable) | DNA / RNA | 518 / 605 |
| 11 | NH | -(CH$_2$)-3- | Z-LEED·, where LEED = SEQ ID NO: 3 | caspase-13 | (membrane-impermeable) | DNA / RNA | 518 / 605 |
| 12 | NH | -(CH$_2$)-3- | Z-F· | chymotrypsin | cytoplasm / mitochondrion | DNA / RNA | 518 / 605 |
| 13 | NH | -(CH$_2$)-3- | Suc-AAAA·, where AAAA = SEQ ID NO: 4 | elastase | cytoplasm | DNA / RNA | 518 / 605 |
| 14 | NH | -(CH$_2$)-3- | Suc-AA· | elastase | cytoplasm / mitochondrion | DNA / RNA | 518 / 605 |
| 15 | NH | -(CH$_2$)-3- | Suc-ESQNY·PIVN-, where ESQNYPIVN = SEQ ID NO: 5 | HIV protease | cytoplasm | DNA / RNA | 518 / 605 |
| 16 | NH | -(CH$_2$)-3- | Suc-EHPFH·LVIH-, where EHPFHLVIH = SEQ ID NO: 6 | renin protease | cytoplasm | DNA / RNA | 518 / 605 |
| 17 | S | -(CH$_2$)-3- | [cephalosporin-type structure with thiophene, β-lactam, CO$_2$H, and CH$_2$ groups] | β-lactamase | cytoplasm | DNA / RNA | 518 / 605 |

FIG. 11

Table 4. Enzyme Substrates Associated with Structure 4 and Associated Information

| Substrate No. | X | n | n' | m' | m" | R8 | R9 | W | B |
|---|---|---|---|---|---|---|---|---|---|
| 18 | S | 0 | 2 | 0 | 0 | fused benzene ring | | O | HO-C(=O)-(CH$_2$)$_3$-C(=O)-NH- [β-lactam structure with S, N, C=O, CO$_2$H, C=CH-CH$_2$-] |
| 19 | S | 0 | 5 | 1 | 2 | fused benzene ring | | NH | Ac-DEVD•, where DEVD = SEQ ID NO: 1 |
| 20 | S | 1 | 3 | 1 | 2 | fused benzene ring | | NH | Ac-DEVD•, where DEVD = SEQ ID NO: 1 |
| 21 | S | 2 | 1 | 1 | 2 | fused benzene ring | | NH | Ac-DEVD•, where DEVD = SEQ ID NO: 1 |
| 22 | O | 0 | 3 | 1 | 2 | H | H | NH | Ac-DEVD•, where DEVD = SEQ ID NO: 1 |
| 23 | S | 0 | 3 | 1 | 2 | H | H | NH | Ac-DEVD•, where DEVD = SEQ ID NO: 1 |
| 24 | O | 1 | 3 | 1 | 2 | H | H | NH | Ac-DEVD•, where DEVD = SEQ ID NO: 1 |
| 25 | O | 0 | 3 | 1 | 2 | fused benzene ring | | NH | Ac-DEVD•, where DEVD = SEQ ID NO: 1 |
| 26 | O | 1 | 3 | 1 | 2 | fused benzene ring | | NH | Ac-DEVD•, where DEVD = SEQ ID NO: 1 |

| Target Enzyme | Cellular Site of Enzyme Substrate | Cellular Site of DYE or DYE-B' | $\lambda_{abs} / \lambda_{em}$ (nm / nm) |
|---|---|---|---|
| β-lactamase | cytoplasm | DNA / RNA | 515 / 530 |
| caspase-3 | cytoplasm | DNA / RNA | 515 / 530 |
| caspase-3 | cytoplasm | DNA / RNA | 642 / 660 |
| caspase-3 | cytoplasm | DNA / RNA | 748 / 770 |
| caspase | cytoplasm | DNA / RNA | 435 / 455 |
| caspase | cytoplasm | DNA / RNA | 462 / 481 |
| caspase | cytoplasm | DNA / RNA | 539 / 567 |
| caspase-3 | cytoplasm | DNA / RNA | 491 / 509 |
| caspase-3 | cytoplasm | DNA / RNA | 612 / 630 |

FIG. 12A-2

Table 4. Enzyme Substrates Associated with Structure 4 and Associated Information, continued from Figure 12A

| Substrate No. | X | n | n' | m' | m'' | R$_8$ | R$_9$ | W | B | Target Enzyme | Cellular Site of Enzyme Substrate | Cellular Site of DYE or DYE-B' | $\lambda_{abs}/\lambda_{em}$ (nm / nm) |
|---|---|---|---|---|---|---|---|---|---|---|---|---|---|
| 27 | S | 0 | 3 | 1 | 2 | fused benzene ring | | NH | Ac-LEED•, where LEED = SEQ ID NO: 3 | caspase-13 | cytoplasm | DNA / RNA | 515 / 530 |
| 28 | S | 0 | 3 | 1 | 2 | fused benzene ring | | NH | Ac-LEHD•, where LEHD = SEQ ID NO: 7 | caspase-9 and caspase-6 | cytoplasm | DNA / RNA | 515 / 530 |
| 29 | S | 0 | 3 | 1 | 2 | fused benzene ring | | NH | Ac-VDVAD•, where VDVAD = SEQ ID NO: 8 | caspase-2 | cytoplasm | DNA / RNA | 515 / 530 |
| 30 | S | 0 | 3 | 1 | 2 | fused benzene ring | | NH | Ac-VEID•, where VEID = SEQ ID NO: 2 | caspase-6 | cytoplasm | DNA / RNA | 515 / 530 |
| 31 | S | 0 | 3 | 1 | 2 | fused benzene ring | | NH | Ac-IETD•, where IETD = SEQ ID NO: 9 | caspase-8 | cytoplasm | DNA / RNA | 515 / 530 |
| 32 | S | 0 | 3 | 1 | 2 | fused benzene ring | | NH | Suc-YVAD•, where YVAD = SEQ ID NO: 10 | caspase-1 and caspase-4 | cytoplasm | DNA / RNA | 515 / 530 |
| 33 | S | 0 | 3 | 1 | 2 | fused benzene ring | | NH | CH$_3$(CH$_2$)$_{10}$CO-YVAD•, where YVAD = SEQ ID NO: 10 | caspase-1 and caspase-4 | cytoplasmic membrane | DNA / RNA | 515 / 530 |
| 34 | S | 0 | 3 | 1 | 2 | fused benzene ring | | NH | CH$_3$(CH$_2$)$_8$CO-AA• | elastase | cytoplasmic membrane | DNA / RNA | 515 / 530 |
| 35 | S | 0 | 3 | 1 | 2 | fused benzene ring | | NH | CH$_3$(CH$_2$)$_{10}$CO-FR• | cathepsin B and cathepsin L | cytoplasmic membrane | DNA / RNA | 515 / 530 |

Table 4. Enzyme Substrates Associated with Structure 4 and Associated Information, continued from Figure 12B

| Substrate No. | X | n | n' | m' | m" | $R_8$ | $R_9$ | W | B | Target Enzyme | Cellular Site of Enzyme Substrate | Cellular Site of DYE or DYE-B' | $\lambda_{abs}/\lambda_{em}$ (nm / nm) |
|---|---|---|---|---|---|---|---|---|---|---|---|---|---|
| 36 | S | 0 | 3 | 1 | 2 | fused benzene ring | | NH | $CH_3(CH_2)_6CO$-GGVV·IATVK-, where GGVVIATVK= SEQ ID NO: 11 or $CH_3(CH_2)_6CO$-GGVIA·TVK-, where GGVIATVK= SEQ ID NO: 11 | γ-secretase | cytoplasmic membrane | DNA / RNA | 515 / 530 |
| 37 | S | 0 | 2 | 0 | 0 | fused benzene ring | | O | $^{2-}O_3P$- | phosphatase | cytoplasmic membrane | DNA / RNA | 515 / 530 |
| 38 | S | 0 | 2 | 0 | 0 | fused benzene ring | | O | 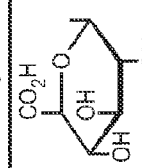 | β-glucuronidase | cytoplasm | DNA / RNA | 515 / 530 |
| 39 | S | 0 | 2 | 0 | 0 | fused benzene ring | | O | 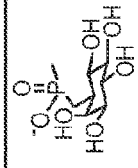 | phosphatidyl inositol-specific phospholipase C | (membrane-impermeable) | DNA / RNA | 515 / 530 |
| 40 | O | 0 | 2 | 0 | 0 | fused benzene ring | | O | 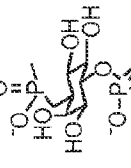 | phosphatidyl inositol-specific phospholipase C | (membrane-impermeable) | DNA / RNA | 515 / 530 |

Table 5. Enzyme Substrates Associated with Structure 6 and Associated Information

| Compound No. | n | X | $R_8$ | $R_9$ | W | B | Target Enzyme | Cellular Site of Enzyme Substrate | Cellular Site of DYE or DYE-B' | $\lambda_{abs}/\lambda_{em}$ (nm / nm) |
|---|---|---|---|---|---|---|---|---|---|---|
| 41 | 0 | S | fused benzene ring | | NH | Ac-AA• | elastase | cytoplasm / membrane | DNA / RNA | 515 / 530 |
| 42 | 0 | S | H | H | O | (sugar with CO$_2$H, OH, and H$_3$C–C–NH, =O) | N-acetyl-β-D-glucosaminidase or a chitinase | cytoplasm | DNA / RNA | 462 / 481 |
| 43 | 0 | O | fused benzene ring | | O | (sugar with CH$_2$OH, OH, and H$_3$C–C–NH, =O) | neurominidase | cytoplasm | DNA / RNA | 491 / 509 |
| 44 | 1 | S | fused benzene ring | | O | (sugar with CH$_2$OH, OH) | β-galactosidase | cytoplasm | DNA / RNA | 642 / 660 |
| 45 | 0 | S | fused benzene ring | | O | $^{2-}O_3P-$ | phosphatase | | DNA / RNA | 515 / 530 |
| 46 | 0 | S | fused benzene ring | | O | (sugar with CO$_2$H, OH) | β-glucuronidase | cytoplasm | DNA / RNA | 515 / 530 |

FIG. 13

Table 6. Enzyme Substrates Associated with Structure 7 and Associated Information

| Substrate No. | Structure | Target Enzyme | Cellular Localization Site of Enzyme Substrate | Cellular Site of DYE or DYE-B' | $\lambda_{abs} / \lambda_{em}$ (nm / nm) |
|---|---|---|---|---|---|
| 47 | 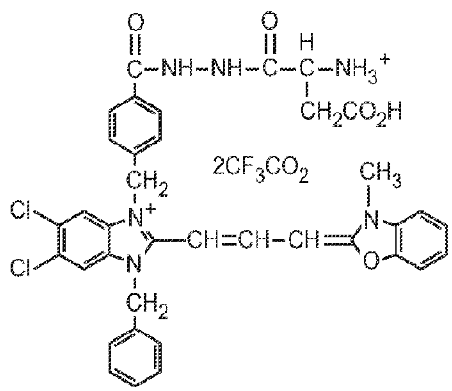 | caspase-3 and caspase-7 | cytoplasm | mitochondrion | 490 / 516 |

| | | | | | |
|---|---|---|---|---|---|
| 48 | (structure with C(=O)-NH-(CH₂)₂-NH-DVED-Ac linked to chlorinated benzimidazolium-benzoxazole chromophore, Cl⁻; where DVED = SEQ ID NO: 1) | caspase-3 | cytoplasm | mitochondrion | 490 / 516 |
| 49 | (structure with glucuronic acid-O-(CH₂)₂-NH-C(=O) linked to chlorinated benzimidazolium-benzoxazole chromophore, Cl⁻) | β-galactosidase | cytoplasm | mitochondrion | 490 / 516 |

*FIG. 14B*

Table 7. Enzyme Substrates Associated with Structure 8A or Structure 8B and Associated Information

| Sub-strate No. | Structure | Target Enzyme | Cellular Localization Site of Enzyme Substrate | Cellular Site of DYE or DYE-B⁺ | $\lambda_{abs}/\lambda_{em}$ (nm / nm) |
|---|---|---|---|---|---|
| 52 | (CH₃)₂N—⟨⟩—CH=CH—⟨N⁺⟩—CH₂C(=O)—NHNH—DVED—Ac where DEVD = SEQ ID NO: 1 | caspase-3 | cytoplasm | mitochondrion | 480 / 600 |
| 53 | (CH₃)₂N—⟨⟩—(CH=CH)₃—⟨N⁺⟩—CH₂C(=O)—NHNH—DVED—Ac where DEVD = SEQ ID NO: 1 | caspase-3 | cytoplasm | mitochondrion | 510 / 750 |
| 54 | (CH₃)₂N—⟨⟩—CH=CH—⟨N⁺⟩—CH₂CH₂—O—[sugar with CO₂⁻, OH, OH, OH] | β-galactosidase | cytoplasm | mitochondrion | 461 / 589 |
| 55 | ⟩N—⟨⟩—(CH=CH)₃—⟨N⁺⟩—CH₂C(=O)—PLG•LWA-D-R-D-R-D-R-NH₂ 4Cl⁻ where "•" indicates cleavage site; D-R-D-R-D-R-NH₂ is a modifier group to increase water-solubility of the substrate; and substrate moiety is attached to DYE via N-linkage | collagenase or gelatinase | extracellular space | cytoplasmic membrane | 510 / 750 |
| 56 | ⟩N—⟨⟩—(CH=CH)₃—⟨N⁺⟩—CH₂C(=O)—PLG•LEA-D-R-D-R-D-R-NH₂ 4Cl⁻ where "•" indicates cleavage site; D-R-D-R-D-R-NH₂ is a modifier group to increase water-solubility of the substrate; and substrate moiety is attached to DYE via N-linkage | matrix metallo-proteinase | extracellular space | cytoplasmic membrane | 510 / 750 |

FIG. 15

SEQUENCE LISTING

```
<160> NUMBER OF SEQ ID NOS: 13

<210> SEQ ID NO 1
<211> LENGTH: 4
<212> TYPE: PRT
<213> ORGANISM: Artificial Sequence
<220> FEATURE:
<223> OTHER INFORMATION: Chemically Synthesized

<400> SEQUENCE: 1

Asp Glu Val Asp
1

<210> SEQ ID NO 2
<211> LENGTH: 4
<212> TYPE: PRT
<213> ORGANISM: Artificial Sequence
<220> FEATURE:
<223> OTHER INFORMATION: Chemically Synthesized

<400> SEQUENCE: 2

Val Glu Ile Asp
1

<210> SEQ ID NO 3
<211> LENGTH: 4
<212> TYPE: PRT
<213> ORGANISM: Artificial Sqeuence
<220> FEATURE:
<223> OTHER INFORMATION: Chemically Synthesized
```

```
<400> SEQUENCE: 3

Leu Glu Glu Asp
1

<210> SEQ ID NO 4
<211> LENGTH: 4
<212> TYPE: PRT
<213> ORGANISM: Artificial Sequence
<220> FEATURE:
<223> OTHER INFORMATION: Chemically Synthesized

<400> SEQUENCE: 4

Ala Ala Ala Ala
1

<210> SEQ ID NO 5
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 5

Glu Ser Gln Asn Tyr Pro Ile Val Asn
1               5

<210> SEQ ID NO 6
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 6

Glu His Pro Phe His Leu Val Ile His
1               5

<210> SEQ ID NO 7
<211> LENGTH: 4
<212> TYPE: PRT
<213> ORGANISM: Artificial Sequence
<220> FEATURE:
<223> OTHER INFORMATION: Chemically Synthesized

<400> SEQUENCE: 7

Leu Gly His Asp
1

<210> SEQ ID NO 8
<211> LENGTH: 5
<212> TYPE: PRT
<213> ORGANISM: Artificial Sequence
<220> FEATURE:
<223> OTHER INFORMATION: Chemically Synthesized

<400> SEQUENCE: 8

Val Asp Val Ala Asp
1               5

<210> SEQ ID NO 9
<211> LENGTH: 4
<212> TYPE: PRT
<213> ORGANISM: Artificial Sequence
<220> FEATURE:
<223> OTHER INFORMATION: Chemically Synthesized

<400> SEQUENCE: 9
```

```
Ile Glu Thr Asp
1

<210> SEQ ID NO 10
<211> LENGTH: 4
<212> TYPE: PRT
<213> ORGANISM: Artificial Sequence
<220> FEATURE:
<223> OTHER INFORMATION: Chemically Synthesized

<400> SEQUENCE: 10

Tyr Val Ala Asp
1

<210> SEQ ID NO 11
<211> LENGTH: 9
<212> TYPE: PRT
<213> ORGANISM: Artificial Sequence
<220> FEATURE:
<223> OTHER INFORMATION: Chemically Synthesized

<400> SEQUENCE: 11

Gly Gly Val Val Ile Ala Thr Val Lys
1               5

<210> SEQ ID NO 12
<211> LENGTH: 4
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: t-butoxy protective group
<220> FEATURE:
<221> NAME/KEY: MISC_FEATURE
<222> LOCATION: (2)..(2)
<223> OTHER INFORMATION: t-butoxy protective group
<220> FEATURE:
<221> NAME/KEY: MISC_FEATURE
<222> LOCATION: (4)..(4)
<223> OTHER INFORMATION: t-butoxy protective group

<400> SEQUENCE: 12

Asp Glu Val Asp
1

<210> SEQ ID NO 13
<211> LENGTH: 4
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (2)..(2)
<223> OTHER INFORMATION: t-butoxy protective group
<220> FEATURE:
<221> NAME/KEY: MISC_FEATURE
<222> LOCATION: (3)..(3)
<223> OTHER INFORMATION: t-butoxy protective group
<220> FEATURE:
<221> NAME/KEY: MISC_FEATURE
<222> LOCATION: (4)..(4)
```

```
<223> OTHER INFORMATION: t-butoxy protective group

<400> SEQUENCE: 13

Leu Glu Glu Asp
1
```

ENZYME SUBSTRATE COMPRISING A FUNCTIONAL DYE AND ASSOCIATED TECHNOLOGY AND METHODS

CROSS-REFERENCE

This application is a Continuation Application which claims the benefit of U.S. application Ser. No. 12/095,322, filed Sep. 24, 2008; which claims the benefit of PCT Application No. PCT/US06/61167, filed Nov. 21, 2006; each of which is incorporated herein by reference in its entirety and to which application we claim priority under 35 USC §120.

SEQUENCE LISTING

The instant application contains a Sequence Listing which has been submitted in ASCII format via EFS-Web and is hereby incorporated by reference in its entirety. Said ASCII copy, created on Dec. 30, 2011, is named 35993-702-301-SEQLIST.txt and is 3 Kilobytes in size.

REFERENCE TO A SEQUENCE LISTING SUBMITTED IN ELECTRONIC FORMAT IN A TEXT FILE AND INCORPORATION BY REFERENCE OF THE CONTENTS THE TEXT FILE

A text file, containing the Sequence Listing for SEQ ID NO: 1 through SEQ ID NO: 13 disclosed herein, is electronically submitted herewith, hereby referred to herein, and hereby incorporated herein in its entirety, including the contents thereof, by this reference.

BACKGROUND

Fluorescent substances or fluorogenic substances, such as those that are responsive to enzyme activity, have a variety of useful applications. Such substances have been used in biological assays, for example.

Enzyme activity in a biological sample, such as a cell, a cell extract, a tissue sample, a biological fluid, a whole organism, and/or the like, is often associated with cellular metabolism, disease state, the success of a genetic manipulation, the identity of a particular microorganism, and/or the like. The ability to detect enzyme activity in a sensitive and quantitative manner may be useful for any of a variety of applications, such as use in cell biology, disease diagnosis, identification of a biological toxin, drug screening, and/or the like, for example. One way to detect enzyme activity is through the use of a fluorogenic enzyme substrate, which is a generally nonfluorescent or only weakly fluorescent compound until it is enzymatically cleaved to release a highly fluorescent dye.

Traditionally, a fluorogenic enzyme substrate has been produced by covalently linking a functional group of a fluorescent dye to a substrate moiety molecule, where the substrate moiety molecule mimics the natural enzyme substrate and thus is recognized by the enzyme being investigated. In general, the functional group of the dye, which is typically either an aromatic primary amine or an aromatic hydroxy group, is an integral part of the chromophoric core structure of the dye, in which the presence of the functional group imparts a spectral property or spectral properties unique to the dye. When the functional group of the dye is covalently linked to a substrate moiety molecule, the functionality of the functional group is changed, resulting in a dramatic blue shift in the absorption and emission wavelengths of the dye and a concomitant reduction in the fluorescent quantum yield of the dye. In some cases, the covalent linkage between the functional group and the substrate moiety molecule of the dye results in a completely colorless and nonfluorescent enzyme substrate. In general, when the functional group of the dye is an aromatic primary amine group, the substrate moiety molecule is an amino acid or a peptide that is recognized by a peptidase. In general, when the functional group of the dye is a hydroxy group, the substrate moiety molecule may be any of a variety of substrate moiety molecules, such as a glycosidyl that is recognized by a glycosidase, a phosphoryl that is recognized by a phosphatase, an alkyl that is recognized by a cytochrome P450 enzyme, or an acyl that is recognized by an esterase, for example. Enzymatic hydrolysis of the fluorogenic enzyme substrate cleaves the bond between the dye and the substrate moiety molecule, thus regenerating the fluorescent dye at a rate proportional to the level of enzyme activity.

Fluorogenic enzyme substrates have been produced using any of a number of fluorescent dyes. For example, amine-containing dyes, such as rhodamine 110, 7-amino-4-methylcoumarin, and 7-amino-4-trifluoromethylcoumarin, for example, have been used for preparing fluorogenic peptidase substrates. Further by way of example, hydroxy-containing dyes, such as fluorescein, 7-hydroxy-4-methylcoumarin, and resorufin, for example, have been used for preparing fluorogenic enzyme substrates in which the enzyme cleavage site is a bond between an oxygen atom and the enzyme substrate moiety molecule. In Table 1 below, a list of a few dyes that have been used for constructing fluorogenic enzyme substrates is provided, along with identifications of the functional group associated with each dye, the substrate moiety molecule associated with each dye, the type of linkage between the functional group and the substrate moiety molecule associated with each dye, and the enzyme that corresponds to the fluorogenic enzyme substrate associated with each dye, merely by way of example.

TABLE 1

Dyes, and Associated Functional Groups, Substrate Moiety Molecules, Linkages, and Enzymes

| Dye | Functional Group | Substrate Moiety Molecule | Linkage | Enzyme |
| --- | --- | --- | --- | --- |
| rhodamine 110 | amine | amino acid or peptide | amide bond | peptidase |
| 7-amino-4-methyl-coumarin | amine | amino acid or peptide | amide bond | peptidase |
| Fluorescein | hydroxy | carboxylic acid | ester bond | esterase |
| Fluorescein | hydroxy | β-D-galactose | ether bond | β-galactosidase |
| Fluorescein | hydroxy | α-D-glucose | ether bond | α-glucosidase |
| Fluorescein | hydroxy | β-D-cellobiose | ether bond | cellulase |
| Fluorescein | hydroxy | phosphate | phosphoester bond | phosphatase |
| Resorufin | hydroxy | alkyl | ether bond | cytochrome P450 |
| 7-hydroxy-4-methyl-coumarin | hydroxy | sulfate | sulfoester bond | aryl sulfatase |

Fluorogenic enzyme substrates have also been designed based on the principle of fluorescence resonance energy transfer (FRET). Such FRET-based design has primarily been used for preparing a fluorogenic peptidase substrate in which the enzyme must bind to both sides of the cleavage site for the enzymatic hydrolysis to take place. A FRET-based peptidase substrate has one dye, called the fluorescence donor, attached to one end of the peptide, and another dye, called the fluorescence acceptor or the fluorescence quencher, attached to the other end of the peptide. Prior to the enzymatic cleavage of the substrate, the fluorescence of the donor is substantially quenched by the quencher as a result of the physical proximity of the donor and quencher. Following the enzymatic hydrolysis of the peptide, the donor and quencher are separated, releasing the fluorescence of the donor at a rate proportional to the level of enzyme activity. There are various examples of FRET-based peptidase substrates, such as the HIV protease substrate described by Wang et al., *Tetrahedron Lett.* 31, 6493 (1990), the renin substrate described by Paschalidou et al., *Biochem. J.* 382, 1031 (2004), and the HCV substrate by Taliani et al., *Anal. Biochem.* 240, 60 (1996), for example. All of these FRET-based enzyme substrates employ a blue fluorescent donor dye. A dye having a short wavelength, such as a blue fluorescent dye, for example, is in general not desirable.

A class of fluorogenic substrates for TEM-1 β-lactamase or Bla, which is a bacterial enzyme that catalyzes the breakdown of cephalosporins with high efficiency, has been a useful variation of fluorogenic peptidase substrates. The gene that encodes for Bla has been used as a reporter gene for studying gene expression in eukaryotic cells. Several fluorogenic Bla substrates have been developed for detecting the reporter enzyme in transfected living cells. One Bla fluorogenic substrate, called CCF2, is a FRET-based compound consisting of a donor 7-hydroxycoumarin linked via a cephalosporin to an acceptor fluorescein. CCF2 is green fluorescent due to FRET from the donor to the acceptor, but becomes blue fluorescent when hydrolysis of the cephalosporin ring structure causes the elimination of the fluorescein molecule. (Zlokarnik et al., *Science* 279, 84 (1998).) FRET-based Bla substrates usually have relatively large molecular weights and poor water solubility, both of which make the substrates difficult to apply to mammalian tissues or cells with thick walls, such as yeast or plant cells, for example. New fluorogenic Bla substrates have been developed by attaching only a single dye with a phenolic group to the 3'-position of a cephalosporin. (Gao et al., *J. Am. Chem. Soc.* 125, 11146 (2003).) Enzymatic hydrolysis of the substrate releases the dye, resulting in a fluorescence increase. These new enzyme substrates have relatively small molecular weights and thus readily enter cells. However, the enzymatically released dyes from these single-dye substrates usually lack the ability to be retained in the cells, making it difficult to identify enzyme-activity-specific cells.

Further development of fluorescent or fluorogenic substances or the making or the use thereof is desirable.

BRIEF SUMMARY

The present invention provides enzyme substrates and associated technology, including associated systems, kits, methods, and the like. An enzyme substrate of the invention may comprise a biologically functional fluorescent dye and an enzyme-specific substrate moiety attached in such a way that the functionality of the functional dye is diminished. An enzymatic reaction may cleave at least a portion of the substrate moiety from the enzyme substrate to provide a more functional product dye. This product dye may be nonfluorescent or weakly fluorescent, in general, and relatively fluorescent, in a particular condition, such as when bound to a partner molecule, partner molecules, or an assembly of partner molecules. An enzyme substrate of the present invention may thus be useful in fluorescence detection, and/or in any of a variety of useful applications, such as the detection of enzymatic activity in a cell-free system or in a living cell, the screening of drugs, or the diagnosis of disease.

These and various other aspects, features, and embodiments of the present invention are further described herein. By this reference, this brief summary fully incorporates the sequence listing, any useful background, the figures, the tables, the panels, the descriptions, the structural formulas, the claims, and the abstract, to the extent same may be suitable for a summary of subject matter herein.

BRIEF DESCRIPTION OF THE DRAWINGS

A detailed description of various aspects, features and embodiments of the present invention is provided herein with reference to the accompanying drawings, which are briefly described below. The drawings are illustrative and are not necessarily drawn to scale. The drawings illustrate various aspects or features of the present invention and may illustrate one or more embodiment(s) or example(s) of the present invention in whole or in part. A reference numeral, letter, and/or symbol that is used in one drawing to refer to a particular element or feature may be used in another drawing to refer to a like element or feature.

FIG. 1 also includes an inset graphical representation of a portion of the emission spectra just described, namely, the boxed-in portion, in an enlarged form.

FIG. 2A and FIG. 2B may be collectively referred to herein as FIG. 2.

FIG. 4A, FIG. 4B, FIG. 4C and FIG. 4D may be collectively referred to herein as FIG. 4.

FIG. 5A, FIG. 5B, FIG. 5C, FIG. 5D, FIG. 5E and FIG. 5F may be collectively referred to herein as FIG. 5. The cells shown in these images were from the same cell population.

FIG. 10 is a presentation of Table 2.
FIG. 11 is a presentation of Table 3.
FIG. 12A-1 is a presentation of the first part of an initial portion of Table 4.
FIG. 12A-2 is a presentation of the second part of an initial portion of Table 4.
FIG. 12B is a presentation of an intermediate portion of Table 4 and is a continuation of FIG. 12A-1 and FIG. 12A-2.
FIG. 12C is a presentation of a final portion of Table 4 and is a continuation of FIG. 12B.
FIG. 13 is a presentation of Table 5.
FIG. 15 is a presentation of Table 7.
FIG. 16A and FIG. 16B may be collectively referred to herein as FIG. 16.
FIG. 18A and FIG. 18B may be collectively referred to herein as FIG. 18.
FIG. 20A, FIG. 20B, and FIG. 20C may be collectively referred to herein as FIG. 20.

DETAILED DESCRIPTION

Figure 1:
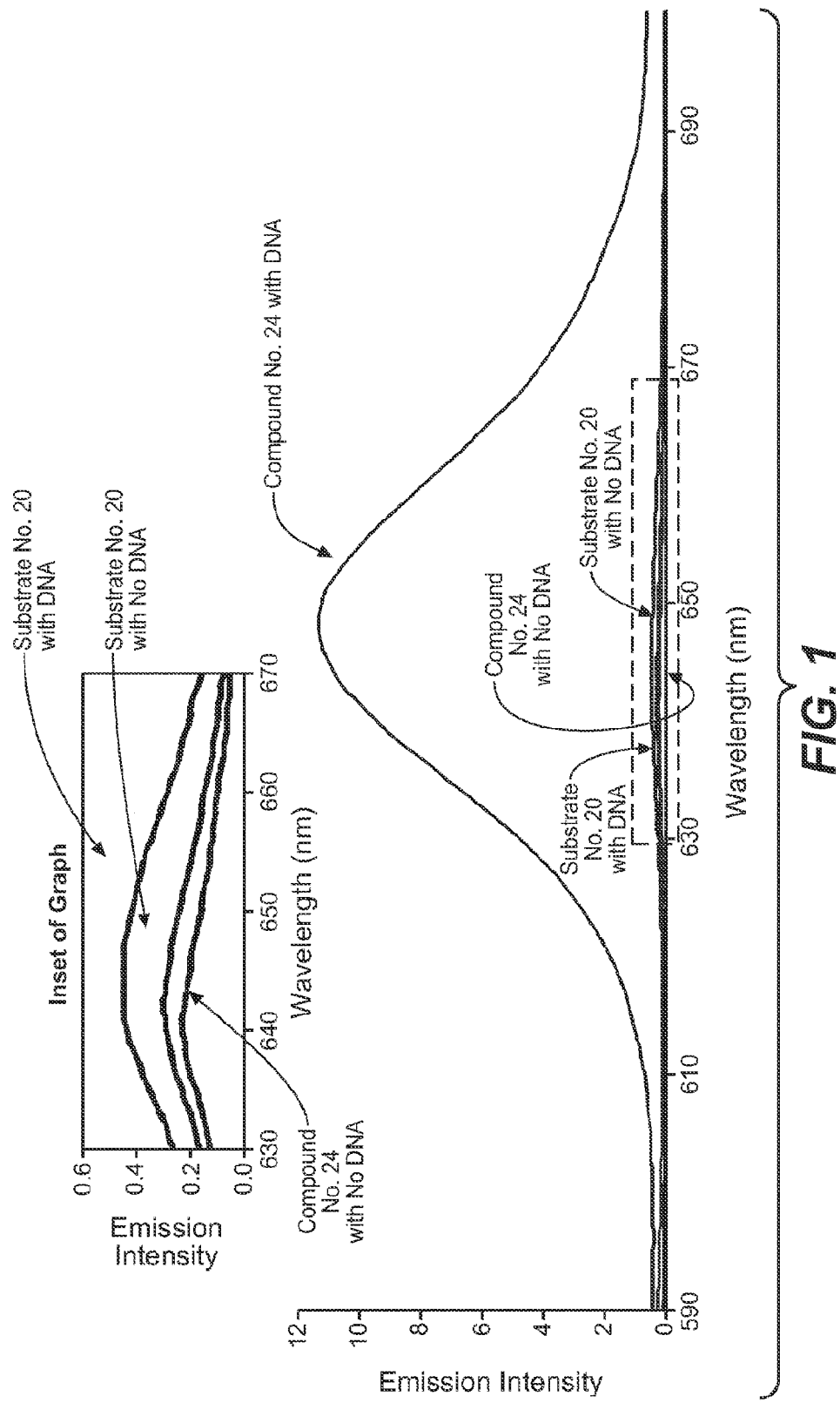
FIG. 1 is a graphical representation of relative florescence emission intensity versus wavelength (nm), or emission spectra, of the an enzyme substrate (Substrate No. 20, at 1 μM) and a control compound (Compound No. 24, at 1 μM) in the absence or presence of dsDNA (at 35 μg/mL in TE buffer), with excitation wavelength set at 600 nm and emission collection wavelength set at 660 nm, as further described in connection with Examples 22, 27 and 51.

In the description of the invention herein, it will be understood that a word appearing in the singular encompasses its plural counterpart, and a word appearing in the plural encompasses its singular counterpart, unless implicitly or explicitly understood or stated otherwise. Further, it will be understood that for any given component described herein, any of the possible candidates or alternatives listed for that component, may generally be used individually or in any combination with one another, unless implicitly or explicitly understood or stated otherwise. Additionally, it will be understood that any list of such candidates or alternatives, is merely illustrative, not limiting, unless implicitly or explicitly understood or stated otherwise. Still further, it will be understood that any figure or number or amount presented herein in connection with the invention is approximate, and that any numerical range includes the minimum number and the maximum number defining the range, unless implicitly or explicitly understood or stated otherwise. Additionally, it will be understood that any permissive, open, or open-ended language encompasses any relatively permissive to restrictive, less open to closed, or less open-ended to closed-ended language, respectively, unless implicitly or explicitly understood or stated otherwise. Merely by way of example, the word "comprising" may encompass "comprising"-, "consisting essentially of", and/or "consisting of"-type language.

Various terms are generally described below to facilitate an understanding of the invention. It will be understood that a corresponding general description of these various terms applies to corresponding linguistic or grammatical variations or forms of these various terms. It will also be understood that the general description of any term below may not apply or may not fully apply when the term is used in a non-general or more specific manner. It will also be understood that the invention is not limited to the terminology used herein, or the descriptions thereof, for the description of particular embodiments. It will further be understood that the invention is not limited to embodiments of the invention as described herein or applications of the invention as described herein, as such may vary.

Generally, the terms "stain" and "dye" may be used interchangeably and refer to an aromatic molecule capable of absorbing light in the spectral range of from about 250 nm to about 1,200 nm. Generally, the term "dye" may refer to a fluorescent dye, a non-fluorescent dye, or both. Generally, the term "fluorescent dye" refers to a dye capable of emitting light when excited by another light of appropriate wavelength.

Generally, the term "fluorogenic" refers to a state or condition of having the capability to be fluorescent following a chemical, biochemical or physical occurrence or event. Generally, the term "fluorogenic dye" refers to a nonfluorescent dye or a weakly fluorescent dye that becomes more fluorescent (such as at least two times more fluorescent, for example) upon the occurrence of a chemical, biochemical, and/or physical event.

Generally, the term "fluorescence quencher" refers to a molecule capable of quenching the fluorescence of another fluorescent molecule. Fluorescence quenching can occur via at least one of the three ways. The first type of fluorescence quenching occurs via fluorescence resonance energy transfer (FRET) (Förster, Ann. Phys. (1948); and Stryer et al., Proc. Natl. Acad. Sci. (1967)), wherein a quencher absorbs the emission light from a fluorescent molecule. The absorption peak of a FRET quencher usually has to have significant overlap with the emission peak of a fluorescent dye for the FRET quencher to be an efficient fluorescent quencher. A FRET quencher is typically a non-fluorescent dye, but can also be a fluorescent dye. When a quencher is a fluorescent dye, only the absorption property of the dye is utilized. A second type of fluorescence quenching occurs via photo-induced electron transfer (PET), wherein the quencher is an electron-rich molecule that quenches the fluorescence of a fluorescent molecule by transferring an electron to the electronically excited dye. A third type of fluorescence quenching occurs via dye aggregation, such as H-dimer formation, wherein two or more dye molecules are in physical contact with one another, thereby dissipating the electronic energy into the vibrational modes of the molecules. This type of contact fluorescence quenching can occur between two identical fluorescent dyes, or between two different fluorescent dyes, or between a fluorescent dye and a FRET quencher, or between a fluorescent dye and a PET quencher. Other types of fluorescence quenchers, though not used as commonly, include stable free radical compounds and certain heavy metal complexes.

Generally, the term "fluorescent nucleic acid stain" or "fluorescent nucleic acid dye" refers to a dye capable of binding to a nucleic acid to form a fluorescent dye-nucleic acid complex. A fluorescent nucleic acid dye is typically non-fluorescent or weakly fluorescent by itself, but becomes highly fluorescent upon nucleic acid binding.

Generally, the term "reactive group" may refer to a "reactive group" or a "functional group" and the term "functional group" may refer to a "reactive group" or a "functional group." Either term may refer, or both terms may refer, to a bond-forming group on a dye, or to a bond-forming group on the substrate moiety molecule. Here, by way of convenience, but not limitation, a bond-forming group on the dye will generally be referred to as a functional group and a bond-forming group on the substrate moiety molecule will generally be referred to as a reactive group. The reactive group and the functional group may be, and typically are, an electrophile and a nucleophile, respectively, that can form a covalent bond.

Generally, the term "pro-substrate" or "pro-enzyme substrate" refers to an enzyme substrate precursor that can be converted to an enzyme substrate though a chemical, biochemical or photochemical process. A pro-substrate may be used to deliver a substrate that may be too polar to cross a cell membrane, for example. By way of example, an enzyme substrate comprising at least one carboxylic acid group may be made into a methyl ester or an acetoxymethyl ester (AM ester) pro-substrate, which may more easily enter cells. Further by way of example, an enzyme substrate comprising at least one phosphate group may be made into a pro-substrate by converting the phosphate group to a phosphate AM ester. Once in the cells, the pro-substrates may be catalytically hydrolyzed back into normal enzyme substrates.

Generally, the term "amino acid" may refer to a natural amino acid, an unnatural amino acid, a protected amino acid, an unprotected amino acid, and/or an amino acid comprising a fluorescence quencher.

Generally, the term "peptide" may refer to a peptide comprising all natural amino acids, a peptide comprising at least one unnatural amino acid, a peptide comprising at least one protection group, a peptide comprising at least one ester linkage in place of a normal peptide linkage, such as for improved enzyme kinetics, for example, and/or a peptide comprising a fluorescence quencher molecule.

Generally, when used in connection with a functional dye, the term "functionality" or "functionality strength" refers to the capacity of the functional dye to fluorescently bind to a partner molecule, partner molecules, an assembly of partner molecules, and/or the like, and is generally defined as: functionality strength=$k\Phi\epsilon$, where k is the association constant between the dye and the partner molecule, partner molecules, assembly of partner molecules, and/or the like; $\Phi$ is the fluorescence quantum yield of the dye bound to the partner molecule, partner molecules, assembly of partner molecules, and/or the like; and $\epsilon$ is the extinction coefficient of the dye bound to the partner molecule, partner molecules, assembly of partner molecules, and/or the like.

In the design of fluorogenic enzyme substrates, one challenge concerns the availability of suitable or desirable fluorescent dyes having various suitable or desirable properties. A desirable fluorescent dye for preparing a fluorogenic enzyme substrate should have long excitation and emission wavelengths, such as an excitation wavelength that is longer than 470 nm and emission wavelength that is longer than 500 nm. There are several dyes available, each having a different set of excitation/emission wavelengths to facilitate multicolor imaging when required. Using long excitation and emission wavelengths in detection can minimize the background signal from sample containers or other biomolecules that may be present. The background signal may be a particularly serious problem for detecting enzyme activity in living cells or tissues because numerous intracellular molecules have intrinsic fluorescence in the blue fluorescence region. For imaging biological activity in living animals, dyes with even longer wavelengths are required. Typically, near infrared (near IR) dyes with wavelengths in the 650-1200 nm region are used because light in this wavelength region has better tissue penetration. (Wyatt et al., *Phil. Trans. R. Soc. London B* 352, 661 (1997).) For these reasons, coumarin dyes, which are usually UV-excitable and blue fluorescent dyes, are not so widely used for designing fluorogenic enzyme substrates. Although both rhodamine 110 and fluorescein have desirable excitation and emission wavelengths in the green color region and have been used for constructing a variety of fluorogenic enzyme substrates, suitable red fluorescent dyes, particularly suitable red dyes for preparing red fluorogenic peptidase substrates, are lacking. A desirable dye should have only one functional group to be used for covalently linking itself to an enzyme substrate moiety molecule so that only a single enzymatic cleavage is required to release the dye, thus simplifying the kinetics of the analysis. Fluorescein and rhodamine 110, both of which have two functional groups, result in substrates that require two cleavage steps to release the parent dyes completely. A desirable dye should be minimally fluorescent, such as completely nonfluorescent, when conjugated to the substrate moiety molecule, but become highly fluorescent following the enzymatic reaction. As mentioned above, it is a challenge to find a suitable or a desirable fluorescent dye for preparing a fluorogenic enzyme substrate.

Another challenge in the design of fluorogenic enzyme substrates concerns the use of the substrates in detecting intracellular enzyme activity in living cells or tissues in a cell-specific manner. Some enzyme assays, such as ELISA and some of the preliminary drug screenings, are carried out in cell-free systems with an isolated enzyme. Some enzyme assays may be carried out with cell lysates. In some applications, however, detecting enzyme activity in living cells is highly desirable or necessary. For example, the ability to fluorescently detect a reporter enzyme in living cells in a cell-specific manner permits one to study gene expression by flow cytometry and microscopy. A substrate comprising a near IR dye may be used to image intracellular enzyme activity in live animals in real-time. Further by way of example, intracellular enzyme detection may be used for high-throughput drug screening. Although screening drug candidates with an isolated intracellular enzyme in a cell-free system can yield useful information, it does not account for the fact that many intracellular enzymes exert their activities in concert with other cellular receptors and cofactors, and does not test for the potential toxicity of the drug candidates and their efficiency in crossing cell membranes. Cell-based drug screening offers far more pharmacologically relevant information concerning not only the interaction between the drug candidate and the target binding molecule, but also the interaction between the drug candidate and the entire cellular environment.

In the design of fluorogenic enzyme substrates for intracellular enzyme detection, two issues should be addressed. One issue concerns the membrane permeability of the substrate, which is determined primarily by the individual membrane permeability of the substrate moiety molecule and the dye. Since only limited chemical modification of the substrate moiety molecule may be employed to improve its membrane permeability without changing its enzyme kinetics, it is useful to select a dye that has good membrane permeability. Another issue concerns the retention of the fluorescent product within the cell following the enzymatic reaction. One of two approaches is generally employed to facilitate such retention. One approach is to prepare an enzyme substrate using a dye with a reactive group, such as a haloalkyl group (U.S. Pat. No. 5,576,424) or a perfluorobenzoyl thiol-reactive group (Zhang et al., *Bioconjugate Chem.* 14, 458 (2003)), that is capable of conjugating the dye or the enzyme substrate to the highly polar glutathione or proteins within the cells under physiological condition. Once the enzyme substrate is hydrolyzed, the resulting dye-glutathione or dye-protein conjugate is trapped within the cells by virtue of high polarity, thus producing a fluorescence signal specific to the cells having the enzyme activity. Another approach is to prepare an enzyme substrate using a dye with a lipophilic tail, which both facilitates the delivery of the substrate moiety into the cytoplasm and enables the enzymatically released dye to remain in the cytoplasmic membranes, resulting in a cell-specific fluorescent signal. (U.S. Pat. No. 5,208,148; Cai et al., *Bioorg. Med. Chem. Lett.* 11, 39 (2001)).

A fluorogenic enzyme substrate of the present invention comprises an enzyme substrate moiety molecule and a biological functional dye. The enzyme substrate comprises dual functionality, being able to detect enzyme activity and to fluorescently stain another biomolecule and/or other biomolecules, such as an assembly of biomolecules, for example. The enzyme substrate may be useful in the detection of intracellular enzyme activity in a living cell because the enzymatically released dye may not only remain within the cell, but may also offer information on the quantity, distribution, morphology of a component of the cell, and/or the like, by way of example. The enzyme substrate may be useful for a variety of applications, such as the study of gene expression, drug screening, disease diagnosis, and/or the like, by way of example. At least some enzyme substrates of the invention comprise a near infrared (near IR) functional dye, such that the enzyme substrate may be suitable for imaging enzyme activity in real-time in living animals.

A fluorogenic enzyme substrate of the present invention may be described by the general Formula 1 set forth below, or biologically acceptable salts or pro-enzyme substrates thereof <p style="text-align:center;">DYE-(B)$_m$            Formula 1</p>

In Formula 1, the DYE by itself is a biologically functional fluorescent or fluorogenic dye capable of binding to a partner biomolecule and/or partner biomolecules, such as an assembly of partner biomolecules; independently, each B is an enzyme substrate moiety molecule capable of being transformed by an enzyme; and the subscript, m, indicates a number of substrate moiety molecule(s). The subscript, m, may be 1, 2, 3, 4 or 5. The enzymatic substrate transformation may comprise any of a variety of enzymatic actions, such as bond cleavage between the DYE and each B, bond cleavage within each substrate moiety molecule B, and or bond formation associated with each B, such as phosphorylation of each B, for example.

Herein, a biologically functional fluorogenic or fluorescent dye generally refers to a biological stain, or a dye that imparts fluorescence upon physical association with a partner biomolecule or with other partner biomolecules, such as an assembly of partner biomolecules. A partner biomolecule may be any of a variety of suitable biomolecules, such as DNA, RNA, a protein, and/or a biological receptor, merely by way of example. An assembly of partner biomolecules may be any of a variety of suitable assemblies, such as an assembly in the form of a protein assembly, such as an actin filament and/or a microtubule, merely by way of example, cell organelles, a cell organelle membrane, and/or a cytoplasmic membrane, merely by way of example. The fluorogenic or fluorescent functional dye may be any of a variety of suitable such dyes, such as a DNA dye, a RNA dye, a fluorescent ligand for a protein, proteins, a protein assembly, and/or protein assemblies, merely by way of example, a cytoplasmic membrane dye, a cell organelle dye, such as a dye for a mitochondrion, a Golgi body, an endoplasmic reticulum, a lysosome, and/or an endosome, merely by way of example. Further by way of example, as to fluorescent ligand dyes, fluorescent ligands, which, generally speaking, are fluorescently-labeled small organic molecules that may bind to a protein-based receptor molecules, may be used for the intracellular mapping of target protein molecules. For example, fluorescently-labeled taxols (*J. Biol. Chem.* 275, 26265 (2000)) may be used to visualize microtubules in cells and fluorescently-labeled phalloidins may be used to map actin filaments in cells (*J. Biol. Chem.* 273, 11144 (1998). According to an embodiment of the invention, the DYE comprises a fluorogenic functional dye. The fluorogenic functional dye may comprise a nucleic acid dye or an organelle dye, such as a mitochondrial dye, a vacuole dye, an endoplasmic reticulum (ER) dye, and/or a lysosomal dye, merely by way of example.

In Formula 1, the enzyme substrate moiety molecule B is the portion of the fluorogenic or fluorescent enzyme substrate that interacts directly with an enzyme. Generally speaking, the molecule B may resemble the natural substrate of the enzyme. The enzyme substrate transformation described above may involve a catalytic bond cleavage between the DYE and B to produce a fluorogenic or fluorescent product DYE; a catalytic bond cleavage within B to produce a fluorogenic or fluorescent product DYE-$(B')_m$, where B' comprises a portion of B and m is 1, 2, 3, 4 or 5; or a catalytic bond formation on B to produce a fluorogenic or fluorescent product DYE-$(B'')_m$, where B'' comprises B with at least one additional chemical group and m is 1, 2, 3, 4 or 5. A catalytic bond cleavage may be any suitable such cleavage, such as hydrolysis of a peptide catalyzed by a peptidase, hydrolysis of an ester catalyzed by an esterase, hydrolysis of a backbone phosphate of DNA or RNA catalyzed by a nuclease, dealkylation of an aromatic ether catalyzed by a dealkylase or cytochrome P450, deacetylation of acylated lysine side chains in histone or a similar peptide catalyzed by histone deacetylase (HDAC), or the like, merely by way of example. A catalytic bond formation may be any suitable such formation, such as phosphorylation of a peptide or a carbohydrate substrate moiety catalyzed by a kinase, acylation of a lysine residue side chain in a histone-mimicking peptide catalyzed by histone acetyltransferase (HAT), alkylation of glutathione thiol catalyzed by glutathione transferase, or the like, merely by way of example.

The enzyme substrate moiety molecule B may be any of a variety suitable such molecules, such as an amino acid that is used with a peptidase, a peptide that is used with a peptidase, an α-amino-protected ε-N-acetyllysine that is used with a histone deacetyltransferase (HDAC), a phosphoryl that is used with an alkaline or acid phosphatase, a sulfuryl that is used with a sulfatase, a carbonyl that is used with an esterase, an alkyl that is used with a cytochrome P450 enzyme, a glycosidyl that is used with a glycosidase, a phosphorylated phosphatidylinositol or an unphosphorylated phosphatidylinositol that is used with a phosphatidylinositol-specific phospholipase C, a glycosylated phosphatidylinositol that is used with a phosphatidylinositol-specific phospholipase C, an adenosine-5'-phosphate that is used with a phosphodiesterase, a nucleoside-3'-phosphate that is used with a nuclease or a ribonucleaseptide, and/or the like, merely by way of example.

When the enzyme substrate moiety molecule B is a peptide or amino acid, the peptide or the amino acid may be linked to DYE in a number of ways. One way, referred to herein as "C-linkage," comprises the linkage of the C-terminal carboxylic group of a peptide or the α-carboxylic group of an amino acid to an amine group on the DYE to form a peptide bond, which may or may not be the scissile bond. Enzymatic cleavage of the substrate prepared via C-linkage results in a product DYE that comprises a positively charged amine. Another way, referred to herein as "N-linkage," comprises the linkage of the N-terminal amine group of a peptide or the α-amine group of an amino acid to a carboxylic group on the DYE to form a peptide bond, which may or may not be the scissile bond. Enzymatic cleavage of the substrate prepared via N-linkage results in a product DYE that comprises a negatively charged carboxylate group. The choice of using C-linkage or N-linkage to produce a peptidase substrate may be based on the enzymatic cleavage requirement of the peptide/peptidase pair, whether the cleavage pattern will enhance the functionality of the functional dye following the enzymatic reaction, and/or the like, merely by way of example. Generally speaking, such a choice may be made in favor of the linkage that results in a substrate with low functionality and a fluorogenic or fluorescent product with high functionality, as use of such a substrate may provide a positive detectable signal, which may be advantageous relative to a negative detectable signal. Generally speaking, such a choice may be facilitated by reference to information on the sequence of a peptide substrate moiety, the relationship between the structure and the functionality of a functional dye, and/or the like, merely by way of example.

According to an embodiment of the invention, the substrate moiety molecule B is a peptide or an amino acid that comprises a fluorescence quencher attached to the portion of B that is cleaved from the dye following the enzymatic transformation of the substrate. A substrate of such construction may have improved signal-to-noise ratio, as any background fluorescence due to the interaction between the substrate and nucleic acid may be significantly reduced by FRET effect.

According to an embodiment of the invention, the fluorogenic or fluorescent substrate comprises only one substrate moiety B. According to another embodiment, the fluorogenic or fluorescent substrate comprises two substrate moiety molecules B, wherein each B may be the substrate moiety molecule for the same enzyme, or one B may be the substrate moiety molecule for an enzyme and the other B may be the substrate moiety molecule for another enzyme. According to an embodiment of the invention, each of the two substrate moiety molecules B is the substrate moiety for the same enzyme.

An enzyme substrate of the invention may produce a detectable fluorescence signal in response to enzyme activity by way of a process that comprises enzymatically transforming the enzyme substrate to produce a fluorogenic or fluorescent product DYE, DYE-$(B')_m$ or DYE-$(B'')_m$, and allowing the fluorogenic or fluorescent product and a partner biomolecule, partner biomolecules, and/or an assembly of partner biomolecules to interact or to bind. A detectable fluorescence signal may comprise a positive signal or a negative signal, as may depend on the relative functionality strengths of the enzyme substrate and the corresponding fluorogenic or fluorescent product of the enzymatic reaction. For example, a positive signal may result if the fluorogenic or fluorescent enzymatic product has a stronger functionality than the starting enzyme substrate. Further by way of example, a negative signal may result if the fluorogenic or fluorescent enzymatic product has a weaker functionality than the starting enzyme substrate. In a case in which the substrate is applied to a living cell or living cells, a detectable fluorescence signal may comprise a change in the fluorescent staining pattern of the cell or cells, a combination of changes in the detected fluorescence intensity and fluorescent staining pattern of the cell or cells, and/or the like, merely by way of example.

According to various embodiments of the invention, enzymatic transformation of an enzyme substrate produces a positive fluorescence signal. For example, in one such embodiment, enzymatic transformation of the starting enzyme substrate, DYE-$(B)_m$ of Formula 1, comprises a hydrolytic cleavage of the bond between the DYE and B, which results in a fluorogenic product that is substantially more functional (such as at least two times more functional, for example) than the starting enzyme substrate, thus producing a positive detectable signal. Further by way of example, in another such embodiment, enzymatic transformation of the starting enzyme substrate, DYE-$(B)_m$ of Formula 1, comprises a hydrolytic cleavage of a bond within substrate moiety B to generate a fluorogenic product DYE-B', wherein B' is a portion of B that remains attached to the DYE, that is substantially more functional (such as at least two times more functional, for example) than the starting substrate, thus producing a positive detectable signal.

The sensitivity of enzyme detection associated with the use of an enzyme substrate DYE-$(B)_m$ may be at least partly determined by the background signal, as may be determined by the functionality strength of the enzyme substrate. Generally, a DYE-$(B)_m$ of weaker functionality corresponds to a weaker interaction between the enzyme substrate and a partner biomolecule, partner biomolecules, and/or an assembly of partner biomolecules, and thus, a weaker background fluorescence signal. Accordingly to an embodiment of the invention, the fluorogenic enzyme substrate DYE-$(B)_m$ may have minimal or no functionality.

Any of various suitable methods, or any suitable combination of methods, by which a substrate moiety molecule B conjugated to the DYE reduces or eliminates the functionality of the DYE, may be employed. According to one method, a substrate moiety molecule B may serve as a steric block that is strategically attached to the DYE such that it interferes with the functionality of the DYE. Such a method may be suitable when the DYE is a nucleic acid dye or a biological ligand for a receptor, wherein the nucleic acid dye or the biological ligand may have to possess or to assume a shape that is compatible with the binding site on the nucleic acid or the receptor.

According to another method, a substrate moiety molecule B may carry a net positive charge or a net negative charge so that upon conjugation to the DYE, the substrate moiety molecule B alters the amount and/or the nature of the charge on the DYE that is associated with the functionality of the DYE. Such a method may be suitable for a DYE whose functionality is sensitive to the amount and/or the nature of the charge it carries. For example, most nucleic acid dyes are positively charged. Generally speaking, additional positive charge or charges may enhance the nucleic acid binding associated with a nucleic acid dye. (U.S. Pat. No. 5,321,13.) Attaching a substrate moiety molecule B that bears one or more negative charge(s) to the DYE may be expected to weaken or to completely diminish the nucleic acid binding ability of the DYE. (See FIGS. 1-6 and 8, and associated Examples, for example.)

Further by way of example, mitochondrial dyes generally bear a delocalized positive charge necessary for the dyes to partition into mitochondrial membranes, where there is usually a large negative membrane potential that attracts positively charged dyes. (Biotium, Inc., *Fluorescent Probes and Related Biochemical Reagents for Life Science,* 2005-2006, and references set forth therein.) Attaching a negatively charged substrate moiety molecule B to a mitochondrion-staining DYE may render the DYE less functional or non-functional. (See Examples 33 and 39, for example.)

Figure 7:
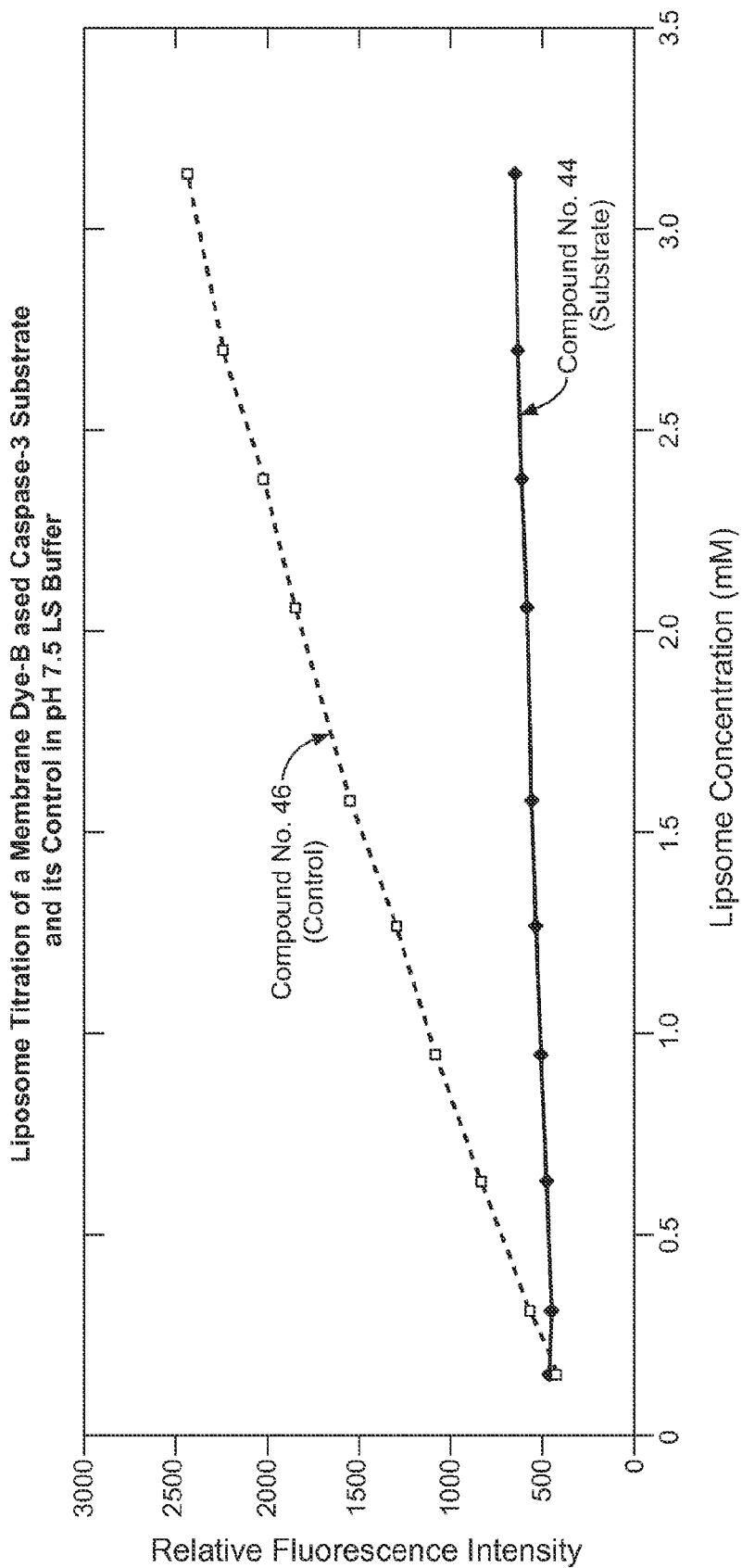
FIG. 7 is a graphical representation of relative fluorescence emission intensity versus liposome concentration (mM), or a liposome titration, of a membrane dye-based substrate (Compound No. 44) for a caspase-3 enzyme and a control (Compound No. 46), as further described in relation to Examples 48, 50 and 57.

According to yet another method, a lipophilic functional dye DYE may be made less functional or nonfunctional by the attachment of a substrate moiety molecule B having high hydrophilicity. According to yet another method, a hydrophilic functional dye DYE may be made less functional or nonfunctional by the attachment of a substrate moiety molecule B having high hydrophobicity. For example, a fluorogenic membrane DYE may be made less functional or nonfunctional via conjugation to a highly water-soluble substrate moiety molecule B. The resulting enzyme substrate, having increased water solubility by virtue of this conjugation, has a reduced ability or no ability to partition into membranes and fluoresce. (See FIGS. 7 and 9, and associated Examples, for example.) Further by way of example, a DNA-binding dye DYE may be made less functional or nonfunctional by conjugation to a membrane-bound substrate moiety molecule B, such as a membrane-bound hydrophobic peptide, for example. The resulting enzyme substrate, residing more or fully in the cell membranes, has a reduced ability or no ability to interact with the DNA in the cell nucleus until a membrane-bound enzyme cleaves the enzyme substrate to release the DYE. (See Substrate No. 36 of Table 4.)

The enzyme substrates may be prepared via a process that is now generally described. The process may comprise appreciating, identifying or determining any of various suitable properties or qualities of the substrate moiety molecule B relative to a given enzyme, such as structural configuration, bulkiness, the amount of any charge, the nature of any charge, hydrophilicity, hydrophobicity, and/or the like, merely by way of example. The process may comprise selecting a functional dye that may be reduced in functionality or de-functionalized by the substrate moiety molecule B. Such a selection may be based on any of the properties or qualities of the substrate moiety molecule B, or any other useful criteria. The process may comprise derivatizing the functional DYE so that it has a suitable functional group for conjugating the substrate moiety molecule B to the DYE. The process comprises conjugating the DYE to the substrate moiety molecule B or a precursor of the substrate moiety molecule B. The process may comprise converting the conjugate to the enzyme substrate.

Once the enzyme substrate is prepared, it may be tested. For example, the enzyme substrate may be incubated with an enzyme for which the enzyme substrate was selected or designed in the presence of at least one partner biomolecule, and/or at least one assembly of partner biomolecules, as may be appropriate in connection with a cell-free application, while the enzymatic reaction is monitored using a suitable detection device, such as a fluorescence microplate reader or a fluorometer, for example. Any detectable change in fluorescence intensity may be taken as an indicator that the substrate may be successfully used for an intended enzyme detection application in a cell-free system. (See Example 53, for example.) Further by way of example, the enzyme substrate may be incubated in at least one cell culture for an appropriate amount of time, such as about 5 minutes or more, wherein the cells of the cell culture contain an enzyme for which the enzyme substrate was selected or designed, as may be appropriate in connection with a cellular application, while the cell culture is monitored for enzymatic activity using a suitable detection device, such as a fluorescence microscope, a fluorescence flow cytometer, or a fluorescence microplate reader, for example. Any detectable change in fluorescence intensity and/or fluorescence staining pattern within the cells may be taken as an indicator that the substrate may be successfully used for an intended enzyme detection application in a cellular system. Further, once the enzyme substrate is prepared, it may be modified. For example, the enzyme substrate may be modified to facilitate obtaining a better or an optimized signal, signal-to-noise ratio, and/or the like, associated with enzyme activity detection. Such a modification may comprise modifying the substrate structure, for example, by varying the position at which the substrate moiety molecule B is attached to the DYE, varying the length of the linker between the substrate moiety molecule B and the DYE, attaching an additional fluorescence quencher molecule to the substrate moiety molecule B, and/or the like, merely by way of example.

Enzyme substrates of the present invention may vary according to the type of functional dyes that are used to produce them. Methods for practicing various aspects of the invention may also vary accordingly. Merely by way of example, various enzyme substrates and associated methods are provided below.

Enzyme Substrate Comprising Nucleic Acid Dye

An enzyme substrate of the present invention may comprise a nucleic acid dye. For the most part, a nucleic acid dye is either an intercalating dye (intercalator) or a minor-groove binding dye (minor groove binder). An intercalator is a dye that inserts itself in between two neighboring base pairs of double-stranded DNA. A minor groove binder is a dye that binds to the minor groove of double-stranded DNA.

The amount of charge on a nucleic acid dye may affect, perhaps profoundly so, the nucleic acid binding ability of the dye. Adding positively charged groups to an intercalator or a minor groove binder may enhance the nucleic acid binding of the nucleic acid dye as a result of the increased electrostatic attraction between the positively charged dye and the negatively charged DNA. (Gaugain et al., *Biochemistry* 17, 5071 (1978); U.S. Pat. No. 5,321,130.) In general, a nucleic acid dye with high nucleic acid binding affinity may provide a high fluorescence signal in the presence of nucleic acid, as a high percentage of the dye may be in the nucleic acid-bound form, which is the fluorescent form of the dye. Attaching negatively charged groups to a nucleic acid dye may decrease or completely diminish the nucleic acid binding ability of the dye, as there may be repulsive interaction between the negatively charged DNA and negatively charged dye.

The functionality of a nucleic acid dye may be sensitive to changes other than changes in the amount and/or the nature of the charge associated with the dye. By way of example, any of various structural modifications of the nucleic acid dye may affect its functionality. Further by way of example, an intercalator or a minor groove binding nucleic acid dye, may have to have or to assume a shape that fits a binding site of a nucleic acid in order for intercalation or minor groove binding to occur. Attaching a sterically bulky group to the nucleic acid dye at a suitable position may disrupt the nucleic acid-dye interaction, rendering the dye weakly functional or completely nonfunctional. The relationship between the structure and the functionality of a nucleic acid dye may be exploited in the design of enzyme substrates of the invention, as may be illustrated in the description below.

A negatively charged substrate moiety molecule B may be covalently linked to a nucleic acid dye to form an enzyme substrate. The nucleic acid dye of the enzyme substrate may have reduced functionality or may be substantially de-functionalized relative to the original nucleic acid dye by virtue of the negative charge associated with the original substrate moiety molecule B, and/or by virtue of steric bulkiness. In an enzymatic cleavage reaction, B or a portion of B associated with the negative charge may be removed to generate a fluorogenic product DYE or DYE-B', which is substantially functional (such as at least two times more functional than the dye of the starting substrate, for example) as a nucleic acid dye. A positive signal may then be generated upon the binding of DYE or DYE-B' to nucleic acid.

A suitable substrate moiety molecule B may be selected according to its application, such as its use in connection with a suitable enzyme. Merely by way of example, a negatively charged amino acid or peptidyl may be used in an application involving a peptidase (see FIGS. 1-5 and 8, and associated Examples, for example), a suitable substrate moiety molecule may be used in an application involving a β-lactamase (see Example 45, for example), a phosphoryl may be used in an application involving a phosphatase, a negatively charged glycosidyl may be used in an application involving a glycosidase (see Substrate No. 38 of Table 4, for example), a sulfuryl may be used in an application involving a sulfatase, a phosphatidylinositoyl may be used in an application involving a phosphatidylinositol-specific phospholipase C (see Substrate Nos. 39 and 40 of Table 4, for example), and/or the like. Further by way of example, a peptide or an amino acid may be linked to a functional dye via a C-linkage or a N-linkage, as previously described. A C-linkage may be used to link the substrate moiety molecule B to the DYE, so that a positively charged amine may be created on the DYE following the enzymatic reaction. A DYE of increased positive charge may have enhanced functionality, which may result in a positive detectable signal, as previously described.

A neutral substrate moiety molecule B may be covalently linked to a nucleic acid dye at a strategic position of the dye to form an enzyme substrate of the invention. Such a substrate moiety may disrupt the interaction between the dye of the enzyme substrate and nucleic acid, until the substrate moiety is sufficiently removed by the enzymatic action to form a more functional nucleic acid dye that may provide a positive detectable signal. Such a neutral substrate moiety molecule B may be any of various suitable such molecules, such as a peptide that may be used in an application involving an elastase (see Example 26, for example), an ε-N-acetyllysine residue that may be used in an application involving histone deacetyltransferase (HDAC) (see Example 23, for example), neutral glycosidyls that may be used in an application involving a glycosidase, an alkyl that may be used in an application involving cytochrome P450, and/or the like, merely by way of example.

A lipophilic substrate moiety molecule B may be covalently linked to a nucleic acid dye to form an enzyme substrate of the invention, such as one that may reside in a cell membrane, for example. The membrane-bound enzyme substrate may be catalytically cleaved by a membrane enzyme to release a functional nucleic acid dye, DYE, which may then migrate to the cell nucleus to stain nuclear DNA. (See Substrate No. 36 of Table 4, for example.) Merely by way of example, a cytoplasmic membrane-bound protease may be γ-secretase, an enzyme associated with the formation of β-amyloid plaque associated with Alzheimer's disease.

A highly functional fluorogenic or fluorescent enzyme substrate may be prepared by attaching a positively charged substrate moiety molecule B to a nucleic acid dye. Enzymatic cleavage of the substrate may provide a product DYE or DYE-B', where B' is a portion of B that does not carry a positive charge, that is less functional than the dye of the enzyme substrate. In such a case, relative to the interaction between the enzyme substrate and nucleic acid and the associated fluorescence signal, the interaction between the product DYE or DYE-B' and nucleic acid and the associated fluorescence signal, respectively, are weaker, and the detected fluorescence signal is negative. Merely by way of example, an enzyme substrate may comprise a nucleic acid dye and a polycationically charged peptide substrate moiety molecule B, and an enzymatic reaction may remove B or a portion of B that carries positive charge, such that the product DYE or DYE-B' is a less functional nucleic acid dye.

A functional fluorogenic or fluorescent substrate may be prepared from a nucleic acid dye covalently attached to a substrate for a kinase. Upon enzymatic phosphorylation of the substrate by the kinase, the functionality of the substrate may be weakened, such that a negative signal is produced.

Virtually any nucleic acid dye may be used as the DYE in the preparation of DYE-(B)$_m$ according to any of the methods described above, or any combination of such methods, provided that the nucleic acid dye has a suitable functional group or the nucleic acid dye may be derivatized to have a suitable functional group. Herein, DYE may refer to a nucleic acid dye that already comprises a functional group or a nucleic acid dye that is derivatized to comprise a functional group. A functional group may react with a reactive group to form a covalent bond. Herein, a nucleic acid dye comprising a suitable functional group may be covalently attached to a suitable substrate moiety or a suitable precursor substrate moiety comprising a suitable reactive group.

An example of a suitable nucleic acid dye may be used as in the preparation of DYE-(B)$_m$ may be any of the intercalating 3,8-diamino-6-phenylphenanthrodium dyes. The two aromatic amino groups of such a 3,8-diamino-6-phenylphenanthrodium dye are associated with the unique spectral property and the nucleic acid binding property of the dye. Any chemical modification of the amino groups may affect, perhaps significantly so, such a property or such properties of the dye. These amino groups may serve as ideal sites for attaching a substrate moiety molecule B so that a positive detectable fluorescence signal may be generated following the cleavage of the substrate moiety molecule B from the dye. A general representative structure for an enzyme substrate prepared using a 3,8-diamino-6-phenylphenanthrodium and a one- or two-peptide substrate moiety molecule B is shown as Structure 1 below.

Structure 1

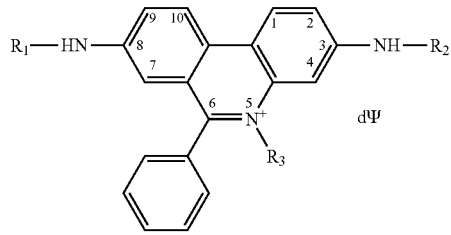

According to an embodiment of the invention, an enzyme substrate associated with Structure 1 may be generally described as follows. The substrate moiety molecule B may be a peptide or an amino acid. At least one of $R_1$ and $R_2$ may be B, where the C-terminal carbonyl of B forms the enzymatically cleavable peptide bond with the amino group of the dye. When $R_1$ or $R_2$ is not B, it is H.

$R_3$ may be a substituted or an unsubstituted C1 to C10 alkyl. The size of $R_3$ may affect the nucleic acid-binding affinity of the dye, as well as the membrane permeability of the corresponding enzyme substrate DYE-(B)$_m$. When B is a charged peptide, $R_3$ may be a C4 to a C10 alkyl, or a C4 to a C8 alkyl. When B is a neutral peptide, $R_3$ may be a C1 to a C6 alkyl.

The nucleic acid-binding affinity of the dye generally decreases as the size of $R_3$ increases. When the enzyme substrate is employed to detect enzyme activity in a cell-free system, $R_3$ may be a small alkyl, typically a methyl or an ethyl. When the enzyme substrate is employed to detect enzyme activity in live cells, DYE-(B)$_m$ should be of sufficient membrane-permeability, which is generally proportional to the overall hydrophobicity of the substrate. A larger $R_3$ may help enhance the hydrophobicity and thus the membrane-permeability of the substrate, but may compromise the overall performance of the substrate by lowering the nucleic acid binding affinity of the dye. An optimal range for the size of $R_3$ may be one that provides an enzyme substrate of Structure 1 comprising a suitable membrane-permeability for the substrate, a suitable nucleic acid binding affinity for the dye, or both. The choice of a suitable $R_3$ may also depend on the nature of the substrate moiety molecule B, which itself may either increase or decrease the hydrophobicity of the substrate.

$\psi$ may be a positively charged or negatively charged, biologically compatible counter ion. $\psi$ may serve to balance the overall charge of the enzyme substrate, such that the enzyme substrate is neutral in overall charge. Merely by way of example, a positively charged $\psi$ may be $H^+$, $Na^+$, $K^+$, $NH_4^+$, N,N,N-triethylammonium, N,N-diisopropylethylammonium, or the like. Merely by way of example, a negatively charged $\psi$ may be a halide, a sulfate, a phosphate, a perchlorate, a hexafluorophosphate, a tetrafluoroborate, or the like. d is a number of $\psi$ that serves to balance the charge of the enzyme substrate.

The 8-amino group of the dye is generally more reactive than the 3-amino group of the dye. Thus, generally, the predominant product of conjugation of B to the dye is a substrate having a single B attached to the 8-amino group, in relatively high yield and of relatively simple enzyme kinetics.

Merely by way of example, a list of enzyme substrates that are generally represented by Structure 1 above is provided in Table 2 of FIG. 10, along with information concerning same. Some general conventions apply to Table 2, as now described. In the columns labeled $R_1$ and $R_2$ of Table 2, bold-faced type is used to indicate amino acid residues associated with enzyme recognition and normal-faced type is used to indicate protection groups for amino acids or peptides. Additionally, in the column labeled $R_1$, SEQ ID NO: 1, SEQ ID NO: 2, and SEQ ID NO: 3 are associated with certain of the amino acid residues shown in bold-faced type. In the column labeled "Cellular Localization Site of Enzyme Substrate," an indication of the approximate cellular location of the enzyme substrate, if the enzyme substrate is applied to living cells, is provided. In this column, "membrane-impermeable" is indicated when the enzyme substrate may not be able to cross a cell membrane for intracellular enzyme activity detection. Such membrane-impermeable substrates may be used for cell-free enzyme activity detection, such as in a cell-free system of cell lysates, for example, or may be used extracellular enzyme activity detection, such as in a live cell system, for example. In general, each of the enzyme substrates may be used in a cell-free system, regardless of its cell membrane-permeability. In the column labeled "Cellular Site of DYE," an indication of the binding site of DYE following enzymatic cleavage is provided. Generally, in a living-cell system, the enzyme substrate is enzymatically cleaved to generate DYE at a site where the enzyme substrate is initially located, and the resulting DYE migrates to the cell nucleus where the DYE binds to dsDNA. Depending on the binding selectivity of the DYE to DNA and RNA, some of the DYE may bind to RNA in the cytoplasm. Finally, in the column labeled "$\lambda_{abs}/\lambda_{em}$ (nm/nm)," the wavelengths provided refer to the wavelengths for the DNA-bound DYE.

According to an embodiment of the invention, the substrate moiety molecule B may be attached via a linker L to the 5-position of a 3,8-diamino-6-phenylphenanthrodium. A general representative structure for an enzyme substrate prepared using such a substrate moiety molecule B is shown as Structure 2 below.

Structure 2

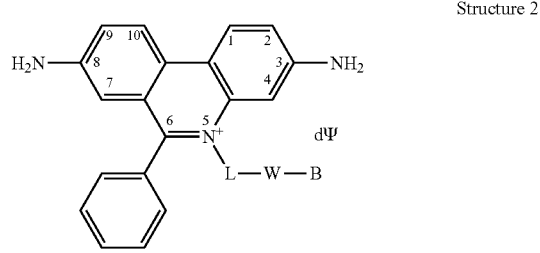

In the enzyme substrate generally represented by Structure 2 above, L may be an aliphatic C2 to about C10 linker, optionally comprising an aryl and at least one hetero atom, such as any heteroatom of the heteroatoms O, S, N, F, and Cl, for example. L may be a relatively short linker, such as a C2 to a C6 linker. In such a case, the substrate moiety molecule B may affect the functionality of the dye to a greater extent. W may be an atom or atoms suitable for the formation of a scissile bond between the DYE and B for a specific enzyme, or may be an atom or atoms suitable for the formation of a covalent link between B and the DYE, wherein the enzymatic bond formation site is on B or the enzymatic cleavage site is within B. W may be any atom or atoms of atoms O, NH and S. The substrate moiety molecule B may be an amino acid or a peptide attached to W via a C-linkage, such as an amino acid that is used with a peptidase, or a peptide that is used with a peptidase, each of which may be referred to as a peptidase substrate moiety; an α-amino-protected ε-N-acetyllysine that is used with a histone deacetyltransferase (HDAC), which may be referred to as a HDAC substrate moiety; a phosphoryl that is used with an alkaline or an acid phosphatase, which may be referred to as a phosphatase substrate moiety; a sulfuryl that is used with a sulfatase, which may be referred to as a sulfatase substrate moiety; a carbonyl that is used with an esterase, which may be referred to as an esterase substrate moiety; an alkyl that is used with a cytochrome P450 enzyme, which may be referred to as a cytochrome P450 substrate moiety; a β-D-glucuronidyl that is used with a β-glucuronidase, a β-D-galactopyranosidyl that is used with a β-D-galactosidase, an α-D-galactopyranosidyl that is used with an α-D-galactosidase, an α-D-mannopyranosidyl that is used with an α-D-mannosidase, an α-D-glucopyranosidyl that is used with an α-D-glucosidase, a β-D-glucopyranosidyl that is used with a β-D-glucosidase, a X-β-D-cellobiosidyl that is used with a β-cellobiosidase, a N-acetyl-β-D-galactosaminidyl that is used with a neuromimidase, a N-acetyl-β-D-glucosaminidyl that is used with a N-acetyl-β-D-glucosaminidase or a chitinase, each of which is a glycoside and may be referred to as a glycosidase substrate moiety; a phosphorylated or an unphosphorylated phosphatidylinositol that is used with a phosphatidylinositol-specific phospholipase C, or a glycosylated phosphatidylinositol that is used with a phosphatidylinositol-specific phospholipase C, each of which may be referred to as a phosphatidylinositol-specific phospholipase C substrate moiety; an adenosine-5'-phosphate that is used with a phosphodiesterase, which may be referred to as a phosphodiesterase substrate moiety; a nucleoside-3'-phosphate that is used with a nuclease or a ribonuclease, which may be referred to as a ribonuclease substrate moiety; a substrate moiety that is used with a β-lactamase, which may be referred to as a β-lactamase substrate moiety; or the like, merely by way of example. In Structure 2, d and ψ are as previously described in connection with Structure 1.

According to an embodiment of the invention, the substrate moiety molecule B may be a peptide or amino acid that comprises at least one enzymatically removable negative charge (ERNC). Merely by way of example, a peptide substrate moiety B may have at least two ERNCs. An ERNC generally refers to a negative charge from an aspartic acid residue, a glutamic acid residue, or a negatively charged modifying group that is attached to the peptide or the amino acid that is removed from the nucleic acid dye as a result of the enzymatic cleavage of the substrate moiety molecule B. A nucleic acid dye-based enzyme substrate that carries more ERNCs may generally be associated with a greater fluorescence signal-to-noise ratio. An excessive amount of negative charge may render it more difficult for the enzyme substrate to cross cell membranes. Thus, a consideration of how much negative charge is suitable may require some balance. Merely by way of example, in intracellular enzyme detection, the number of negative charges on an enzyme substrate may be less than 5, or less than 4. Merely by way of example, in other applications, such as cell-free enzyme detection or extracellular enzyme detection in a cell culture, tissue sample, or in a living animal, for example, generally speaking, there may be no limit on the number of ERNCs a nucleic acid dye-based enzyme substrate may carry. The charge of a neutral peptide substrate moiety or a peptide substrate moiety that has only one ERNC may be made more negative without affecting the specificity of the enzyme substrate for the enzyme, as may be accomplished by covalently attaching a negatively charged or a poly-negatively charged modifying group to the N-terminal of the substrate moiety. By way of example, a single negative charge may be added to a neutral peptide via attachment of a glutamic acid thereto, or via reaction of the N-terminal α-amine of the neutral peptide and succinic anhydride. Further by way of example, a triple negative charge may be added to the neutral peptide via attachment of a tri-aspartic peptide to the N-terminal of the neutral peptide.

According to an embodiment of the invention, the substrate moiety molecule B is a peptide or an amino acid that comprises a fluorescence quencher attached to the portion of B that is cleaved from the dye following the enzymatic transformation of the substrate. Merely by way of example, the substrate moiety molecule B may comprise a peptide that comprises a fluorescence quencher, wherein the fluorescence quencher is attached to the N-terminal of an enzyme substrate moiety for an enzyme, such as a caspase enzyme, for example, and wherein the fluorescence quencher is sufficient for removal from the dye upon enzymatic transformation of the substrate.

According to an embodiment of the invention, the substrate moiety molecule B may be a neutral substrate moiety that reduces or substantially eliminates the functionality of the nucleic acid dye. Merely by way of example, the substrate moiety molecule B may act as a steric impediment or block that interferes with the nucleic acid binding of the dye.

According to an embodiment of the invention, the substrate moiety molecule B may be a substrate moiety for β-lactamase. Merely by way of example, general representative structures for two such substrate moieties are shown as Sub-structure 1 and Sub-structure 2, respectively, below.

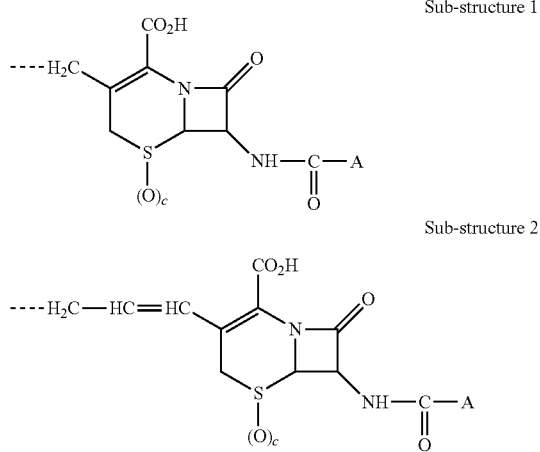

In either of Sub-structure 1 and Sub-structure 2, the dotted line represents the covalent bond between the substrate moiety and W shown in Structure 2. A may be a substituted C1 to C20 alkyl or aryl, optionally comprising at least one hetero atom, such as N, O and/or S, for example, and optionally comprising at least one negatively charged group, such as a carboxylate, a sulfonate, and/or a phosphate, for example; or A may be a fluorescence quencher; and c may be 0, 1 or 2. Examples of substrate moieties for β-lactamase appear in U.S. Pat. Nos. 5,741,657, 5,955,604, and 6,031,094, and U.S. Patent Application Publication Nos. 2005/0227309 and 2005/0118669. Any such substrate moiety may be combined with a nucleic acid dye to prepare a fluorescent or fluorogenic β-lactamase substrate.

Merely by way of example, a list of enzyme substrates that are generally represented by Structure 2 above is provided in Table 3 of FIG. 11, along with information concerning same. Some general conventions apply to Table 3, as now described. In the column labeled B of Table 3, bold-faced type is used to indicate amino acid residues associated with enzyme recognition, normal-faced type is used to indicate protection groups for amino acids or peptides, and "•" is used to indicate a peptide scissile bond. Additionally, in the column labeled B, SEQ ID NO: 1, SEQ ID NO: 2, SEQ ID NO: 3, SEQ ID NO: 4, SEQ ID NO: 5, and SEQ ID NO: 6 are associated with certain of the amino acid residues shown in bold-faced type. As to each of SEQ ID NO: 5 and SEQ ID NO: 6, the first "Glu" or "E" of the sequence, may be a modifying group. The enzymatic cleavage site associated with the β-lactamase substrate moiety B is the lactam ring, the opening of which triggers the elimination of the DYE (comprising the -L-W moiety) from the 3' position. In the columns labeled "Cellular Localization Site of Enzyme Substrate," "Cellular Site of DYE or DYE-B'," and "$\lambda_{abs}/\lambda_{em}$ (nm/nm)," applicable conventions are generally as previously described in relation to Table 2, although the Cellular Site of DYE or DYE-B' refer to the cellular site of the former or the latter, and the $\lambda_{abs}/\lambda_{em}$ refer to the wavelengths for the DNA-bound DYE or DNA-bound DYE-B'.

As previously described, substrates generally represented by Structure 1 and Structure 2 are based on 3,8-diamino-6-phenylphenanthrodium dye. Other phenanthrodium dyes may be used to prepare enzyme substrates of the invention in any suitable manner, such as that described in relation to the 3,8-diamino-6-phenylphenanthrodium dye. The preparation and use of various phenanthrodium dyes, such as drug-related use, have been described earlier. (Watkins, *J. Chem. Soc.* 3059 (1952); Watkins et al., *Nature* 169, 506 (1952).)

A general representative structure for an enzyme substrate according to an embodiment of the invention is shown as Structure 3 below.

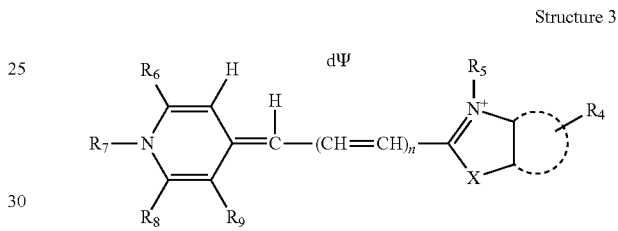

In the enzyme substrate generally represented by Structure 3 above, the DYE is an asymmetric cyanine-based nucleic acid dye. The dotted line shown in Structure 3 represents the atoms associated with formation of at least one fused aromatic ring, optionally comprising at least one nitrogen, which may or may not be quaternized. The represented atoms may be those associated with the formation of at least one fused benzene ring, merely by way of example. X may be O or S, for example. In Structure 3, n is 0, 1, 2 or 3, and d and ψ are as previously described in connection with Structure 1 and Structure 2.

At least one ligand, but no more than two ligands, of ligands $R_4$, $R_5$, $R_6$ and $R_7$ shown in Structure 3 may be represented as -L-W—B, where L, W and B are as described in relation to Structure 2. Merely by way of example, just one ligand of ligands $R_4$, $R_5$, $R_6$ and $R_7$, just one ligand of ligands $R_5$ and $R_7$, or just ligand $R_7$ may be so represented as -L-W—B.

When $R_4$ is not -L-W—B, it may be H; a C1 to about C6 alkyl; a C1 to about C6 alkoxy; a halogen; or an aryl meta to X, wherein the aryl optionally comprises at least one hetero atom of hetero atoms N, O and S. Merely by way of example, $R_4$ may be H; a methoxy meta to X; or an aryl meta to X, wherein the aryl optionally comprises at least one hetero atom of hetero atoms N, O and S. When $R_5$ is not -L-W—B, it may be a C1 to about C6 alkyl, such as a methyl, for example. When $R_6$ is not -L-W—B, it may be H; a C1 to about C10 alkyl, wherein the alkyl optionally comprises at least one hetero atom of hetero atoms N, O and S; a halogen; a C1 to C10 alkoxy or alkylmercapto, wherein the alkoxy or the alkylmercapto optionally comprises at least one hetero atom of hetero atoms N, O, and S; a C2 to about C12 dialkylamino, wherein the dalkylamino optionally comprises at least one hetero atom of hetero atoms N, O, and S; or a substituted or an unsubstituted aryl, wherein the aryl optionally comprises 1 to 3 hetero atom(s) of hetero atoms halogen, N, O and S. When $R_6$ is not -L-W—B, it may be H; a C1 to about C6 alkyl; a C1 to about C6 alkoxy or alkylmercapto; a C2 to about C12 dialkylamino, optionally comprising one N; or a substituted or an unsubstituted aryl, optionally comprising 1 to 3 hetero atom(s) of hetero atoms N, O and S, merely by way of example. When $R_7$ is not -L-W—B, it may be H; a C1 to about C10 alkyl, optionally comprising an aryl and at least one hetero atom of hetero atoms N, O, and S; or a substituted or an unsubstituted aryl, optionally containing 1 to 3 hetero atom(s) of hetero atoms halogen, N, O, and S. When $R_7$ is not -L-W—B, it may be a C1 to about C3 alkyl, optionally comprising an aryl, merely by way of example.

Independently, each of $R_8$ and $R_9$ may be H; a C1 to about C10 alkyl, optionally comprising at least one hetero atom of hetero atoms N, O, and S; a halogen; a C1 to C10 alkoxy or alkylmercapto, wherein the alkoxy or the alkylmercapto optionally comprises at least one hetero atom of hetero atoms N, O, and S; a C2 to about C12 dialkylamino, optionally comprising at least one hetero atom of hetero atoms N, O, and S; a substituted or an unsubstituted aryl, optionally comprising 1 to 3 hetero atom(s) of hetero atoms halogen, N, O and S. $R_8$ and $R_9$ may, in combination, form a fused aromatic ring, which may be further substituted 1 to 4 time(s) independently by C1-C2 alkyl, C1-C2 alkoxy, C1-C2 alkylmercapto, or a halogen. Merely by way of example, $R_8$ and $R_9$ are both H. Further, merely by way of example, $R_8$ and $R_9$, in combination, form a fused 6-membered ring, which may be further substituted one time by a methyl, methoxy, methylmercapto, or a halogen.

According an embodiment of the invention, an enzyme substrate such as that generally represented by Structure 3 above may comprise a glycosidyl, such as a glycosidyl enzyme substrate for a glycosidase enzyme, for example.

A general representative structure for an asymmetric cyanine dye-based enzyme substrate, according to an embodiment of the invention, is shown as Structure 4 below.

Structures 1, 2 and 3. Additionally, X may be O or S; each of $R_8$ and $R_9$ may be H, or $R_8$ and $R_9$, in combination, may form a fused benzene ring; and B and W are as previously described in relation to Structure 2.

Merely by way of example, a list of enzyme substrates that are generally represented by Structure 4 above is provided in Table 4 of FIG. 12, along with information concerning same. Some general conventions apply to Table 4, as now described. The general conventions set forth in relation to Table 3 generally apply to Table 4. In the column labeled B of Table 4, when the substrate moiety molecule B is a peptide, bold-faced type is used to indicate amino acid residues associated with enzyme recognition and normal-faced type is used to indicate protection groups for amino acids or peptides. Additionally, in this column, SEQ ID NO: 1, SEQ ID NO: 2, SEQ ID NO: 3, SEQ ID NO: 7, SEQ ID NO: 8, SEQ ID NO: 9, SEQ ID NO: 10, and SEQ ID NO: 11 are associated with certain of the amino acid residues shown in bold-faced type. The enzymatic cleavage site associated with the β-lactamase substrate moiety B is the lactam ring, the opening of which triggers the elimination of the DYE (comprising the -L-W moiety) from the 3' position. In the column labeled "Cellular Localization Site of Enzyme Substrate," an indication of the primary cellular location of the enzyme substrate, if the enzyme substrate is applied to living cells, is provided. In this column, "membrane-impermeable" is indicated when the enzyme substrate is primarily suitable for detecting enzyme activity in a cell-free system. In the column labeled "Cellular Site of DYE or DYE-B'," an indication of the binding site of DYE or DYE-B' following enzymatic cleavage is provided. Generally, in a living-cell application, the primary cellular location of the DYE is the cell nucleus where the DNA resides. Finally, in the column labeled "$\lambda_{abs}/\lambda_{em}$ (nm/nm)," the wavelengths provided refer to the wavelengths for the DNA-bound DYE or DNA-bound DYE-B'.

Structure 4

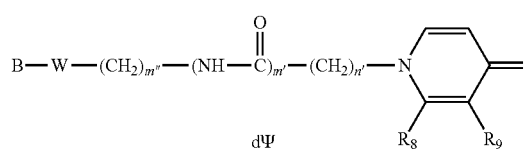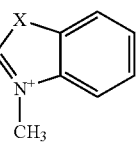

In the enzyme substrate generally represented by Structure 4 above, n may be 0, 1, 2 or 3; n' may be 1, 2, 3, 4 or 5; m' may be 0 or 1; m" is 1, when m' is 0; m" is 0, 2, 3 or 4, when m' is 1; and Ψ and d are as described previously in relation to A general representative structure for an asymmetric cyanine dye-based enzyme substrate, according to an embodiment of the invention, is shown as Structure 5 below.

Structure 5

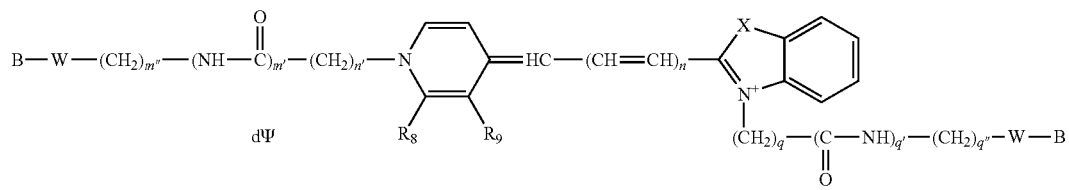

In the enzyme substrate generally represented by Structure 5 above, two substrate moiety molecules B are attached to an asymmetric cyanine dye. In Structure 5, n may be 0, 1, 2 or 3; n' may be 1, 2, 3, 4, or 5; m' may be 0 or 1; when m' is 0, m" may be 1; when m' is 1, m" may be 0, 2, 3 or 4; q may be 1, 2, 3, 4 or 5; q' may be 0 or 1; when q' is 0, q" is 1; when q' is 1, q" may be 0, 2, 3 or 4; and $\Psi$ and d are as described previously in relation to Structures 1, 2, 3 and 4. Additionally, X may be O or S; each of $R_8$ and $R_9$ may be H, or $R_8$ and $R_9$, in combination, may form a fused benzene ring; and B and W are as previously described in relation to Structure 2. The enzyme substrate represented by Structure 5 may comprise any of a number of suitable substrate moiety molecules B, such as any of those mentioned previously in relation to Structure 2, merely by way of example. Merely by way of example, the substrate moiety molecule B may comprise a peptide that comprises a fluorescence quencher, wherein the fluorescence quencher is attached to the N-terminal of an enzyme substrate moiety for an enzyme, such as a caspase enzyme, for example, and wherein the fluorescence quencher is sufficient for removal from the dye upon enzymatic transformation of the substrate.

The enzyme substrate generally represented by Structure 5 may be particularly suitable in terms of its two substrate moiety molecules B. While a single substrate moiety molecule B, when conjugated to an asymmetric cyanine dye, may be insufficient to reduce or to eliminate the functionality of the dye, two such molecules may be sufficient in this regard. When the enzyme substrate has two substrate moiety molecules B attached to the same nucleic dye, the nucleic acid-binding affinity of the dye may be significantly altered until both of the molecules are cleaved off the dye, which may result in a substantially more detectable (such as at least two times more detectable, for example) fluorescent signal, or a positive signal of increased fluorescence (such as at least two times more fluorescence, for example). In general, if an enzyme substrate comprising a single substrate moiety molecule B, such as that generally represented by Structure 4, results in a relatively poor signal-to-noise ratio, it may be useful to employ an enzyme substrate having two substrate moiety molecules B, such as that generally represented by Structure 5, instead.

A general representative structure for an asymmetric cyanine dye-based enzyme substrate, according to an embodiment of the invention, is shown as Structure 6 below.

Structure 6

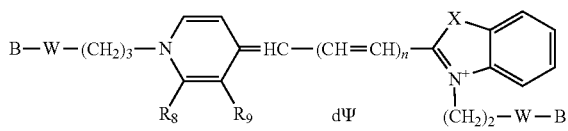

In Structure 6, n, X, $R_8$, $R_9$, B, W, d and $\Psi$ are generally as described above in relation to Structure 5. In the enzyme substrate generally represented by Structure 6 above, two substrate moiety molecules B are attached to an asymmetric cyanine dye via a two-carbon and three-carbon linker, respectively.

Merely by way of example, a list of enzyme substrates that are generally represented by Structure 6 above is provided in Table 5 of FIG. 13, along with information concerning same. The general conventions that apply to Table 5 are generally those previously described in relation to Table 3. All of the enzyme substrates provided in Table 5 may be used for enzyme activity detection in cell-free systems, such as cell lysates, for example, and may be used for extracellular enzyme activity detection, if present, in live cells, for example.

Enzyme Substrate Comprising Fluorescent Membrane Dye

A fluorogenic or fluorescent membrane dye may be a lipophilic dye that has a high tendency to partition into a lipid environment, such as that associated with a liposome membrane or a cellular membrane. In general, a membrane dye is nonfluorescent or only weakly fluorescent in an aqueous phase and becomes highly fluorescent once in a membrane, such that specific membrane staining may result. Membrane dyes have been used for cell tracing, intracellular organelle mapping and cell membrane recycling studies. Generally speaking, membrane dyes may be roughly categorized according to the mechanism or mechanisms by which they interact with a membrane. For example, a membrane dye may be roughly as having a membrane partition that is affected by membrane potential, or as having a membrane partition that is relatively unaffected by membrane potential. A dye in the former category is usually a small dye molecule that carries a delocalized positive charge or a delocalized negative charge, more typically a delocalized positive charge. Membrane staining by such a dye largely relies on the electrostatic interaction between the dye and the electrical field of the membrane. By way of example, a mitochondrial dye carrying one delocalized cation may stain a mitochondrial membrane in a membrane potential-dependent fashion. The response of the staining to a membrane potential change may be a change in fluorescence intensity, a change in fluorescence wavelength, or a combination of both. A mitochondrial dye may be used to measure mitochondrial membrane potential, which may be an important indicator of the metabolic and/or health state of the mitochondria. A dye in the latter category is usually a dye that is more hydrophobic than a dye in the former category. Membrane staining by such a dye primarily involves hydrophobic interaction between the dye and the lipid environment of the membrane. Such a membrane potential-independent membrane dye may be any of suitable such dyes, such as a cytoplasmic membrane dye, an endoplasmic reticulum (ER) dye, an endosome dye, a vacuole dye, a synaptic vesicle dye, and/or the like. Some of the more hydrophobic mitochondrial dyes are also known to stain mitochondria in a membrane potential-independent manner.

According to an embodiment of the invention, a substrate of the invention DYE-(B)$_m$ may comprise the DYE and at least one substrate moiety molecule B, wherein the subscript $_m$ may be as previously described, such as 1, merely by way of example. In this embodiment, the DYE comprises a membrane dye, the at least one substrate moiety molecule B comprises at least one highly water-soluble substrate moiety molecule B, and the enzyme substrate DYE-(B)$_m$ may be a weakly functional membrane dye. Merely by way of example, the enzyme substrate may have increased water-solubility or altered charge relative to the DYE until enzymatic cleavage of the substrate, which may result in a highly functional membrane product DYE or DYE-(B')$_m$, wherein B' is a portion of B. The product DYE is formed when a scissile bond is between DYE and each B. The product DYE-(B')$_m$ is formed when a scissile bond is within each B. Enzymatic cleavage of the substrate renders the membrane dye functional, such that in the presence of a membrane, the functional dye may partition into the membrane and a positive detectable fluorescence signal may be produced. In general, the positive fluorescence signal is increased at least about 2-fold relative to any background fluorescence associated with the starting enzyme substrate, such as at least about 10-fold or at least about 50-fold, merely by way of example.

According to an embodiment of the invention, the substrate moiety molecule B may be any of a number of suitable substrate moieties, such as a charged amino acid that is used with a peptidase, wherein the amino acid is linked to the DYE via either C-linkage or N-linkage as previously described; a charged peptide that is used with a peptidase, wherein the peptide is linked to the DYE via either C-linkage or N-linkage as previously described and the peptide may optionally comprise a fluorescence quencher that is removed from the DYE following the enzymatic transformation of the substrate; a substrate moiety that is used with a β-lactamase; a phosphoryl that is used with an alkaline or an acid phosphatase; a sulfuryl that is used with a sulfatase; a β-D-glucuronidyl that is used with a β-glucuronidase; a β-D-galactopyranosidyl that is used with a β-D-galactosidase; an α-D-galactopyranosidyl that is used with an α-D-galactosidase; an α-D-mannopyranosidyl that is used with an α-D-mannosidase; an α-D-glucopyranosidyl that is used with an α-D-glucosidase; a β-D-glucopyranosidyl that is used with a β-D-glucosidase; a X-β-D-cellobiosidyl that is used with a β-cellobiosidase; a N-acetyl-β-D-galactosaminidyl that is used with a neuromimidase; a N-acetyl-β-D-glucosaminidyl that is used with a N-acetyl-β-D-glucosaminidase or a chitinase; a phosphorylated or an unphosphorylated phosphatidylinositol that is used with a phosphatidylinositol-specific phospholipase C; a glycosylated phosphatidylinositol that is used with a phosphatidylinositol-specific phospholipase C; an adenosine-5'-phosphate that is used with a phosphodiesterase; a nucleoside-3'-phosphate that is used with a nuclease or a ribonuclease; and/or the like, merely by way of example.

When the substrate moiety molecule B is a charged peptide, it may comprise a peptide, a neutral segment of which may be involved in enzyme interaction and another segment of which may be involved in modifying, such as increasing, for example, the water-solubility of the peptide. The modification may be facilitated by a modifying group of the latter segment, whether original or added. Such modification may be useful to modify a poorly soluble neutral peptide, such that it may be used in the preparation of a membrane dye-based substrate of the invention. For example, a relatively water-insoluble tetrapeptide substrate moiety Ala-Ala-Ala-Ala (SEQ ID NO: 4) for an elastase may be made more water-soluble by attaching a highly water soluble modifier group. Such a modifier group may be any of suitable such groups, such as a poly-Asp, a poly-Glu, a poly-Lys, a poly-anionic nonpeptide group, a poly-cationic nonpeptide group, a water-soluble fluorescence quencher, and/or the like, merely by way of example.

The DYE may comprise a mitochondrial dye and the scissile bond may be such that following enzymatic cleavage the charge on the mitochondrial dye may be substantially unchanged and the mitochondrial dye may be rendered functional. The scissile bond may be any of suitable scissile bonds, such as a bond derived from a substrate moiety that relies on a hydroxy functional group from the DYE, a peptide bond derived from C-linked peptides and a low pKa amine (such as a pKa of less than 8, for example) functional group from the DYE, and/or the like. According to an embodiment of the invention, the DYE may comprise a symmetrical cyanine, an asymmetrical cyanine, a merocyanine, a styryl dye, and/or the like.

A general representative structure for an enzyme substrate, according to an embodiment of the invention, is shown as Structure 7 below.

Structure 7

dΨ

In the enzyme substrate generally represented by Structure 7, each of $R_1$ and $R_4$, independently, may be H or Cl; $R_2$ may be a C1 to C12 alkyl, such as a methyl or an ethyl, for example, a C7 to C12 arylalkyl, or a -L-W—B; each X and Y, independently, may be $(CH_3)_2C$, O, S, or $NR_3$, where $R_3$ may be a C1 to C12 alkyl, a C7 to C12 arylalkyl, or a -L-W—B; n may be 1, 2 or 3; and Ψ and d are as previously described. Additionally, B comprises a substrate moiety; L may be a C2 to C12 aliphatic linker, optionally comprising an aryl and at least one hetero atom of hetero atoms O and N; and W may be an atom or atoms O, C=O, NH or S, as may be associated with the formation of a scissile bond between W and B for a specific enzyme, or may be an atom or atoms O, C=O, NH or S, as may be associated with the formation of a covalent linkage between B and the DYE, wherein the enzyme cleavage site is within B. Structure 7 comprises no more that two -L-W—B.

According to an embodiment of the invention, in the enzyme substrate generally represented by Structure 7, $R_1$ is Cl; $R_2$ is a methyl; X is N—$R_3$, where $R_3$ is a benzyl; Y is $(CH_3)_2C$, O, or S; $R_4$ is H; each of n, d and Ψ are as described in relation to Structure 7; and -L-W—B is generally represented by Sub-structure 3 below.

Sub-structure 3

$$—CH_2—\underset{}{\underline{\phantom{XXXX}}}—(\overset{O}{\underset{\|}{C}}—NH)_{n'}—(CH_2)_{n''}—W—B$$

In -L-W—B generally represented by Sub-structure 3, W and B are as described in relation to Structure 7 above, and subscripts n' and n" are such that when n' is 0, n" may be 1 or 2, and when n' is 1, n" may be 0, 1 or 2.

According to an embodiment of the invention, in the enzyme substrate generally represented by Structure 7, $R_1$ is Cl; $R_2$ is a methyl; X is N—$R_3$, where $R_3$ is -L-W—B; Y is $(CH_3)_2C$, O, or S; $R_4$ is H; each of n, d and Ψ are as described in relation to Structure 7; and -L-W—B is generally represented by Sub-structure 3 above.

Figures 14, 14A, 14B, 14C:
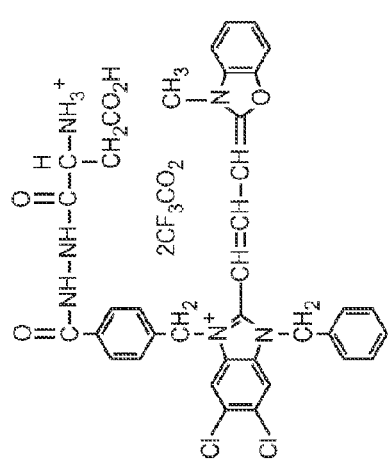
FIG. 14A is a presentation of an initial portion of Table 6.
FIG. 14B is a presentation of an intermediate portion of Table 6.
FIG. 14C is a presentation of a final portion of Table 6.
Figure 14C:
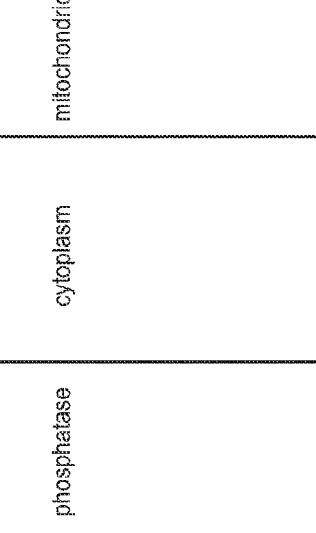

Merely by way of example, a list of enzyme substrates that are generally represented by Structure 7 above is provided in Table 6 of FIG. 14, along with information concerning same. Some general conventions apply to Table 6, as now described. In the column labeled "Structure," bold-faced type is used to indicate amino acid residues and SEQ ID NO: 1 is associated with certain of the amino acid residues shown in bold-faced type. The general conventions that apply to the columns labeled "Cellular Localization Site of Enzyme Substrate," "Cellular Site of DYE or DYE-B'," and "$\lambda_{abs}/\lambda_{em}$ (nm/nm)," Table 6 are generally those previously described in relation to Table 3. All of the enzyme substrates shown in Table 6 may be used in a cell-free system.

A membrane dye-based enzyme substrate of the invention may comprise a styryl dye and a substrate moiety molecule B.

Such an enzyme substrate, according to an embodiment of the invention, may be generally represented by Structure 8A shown below, according to an embodiment of the invention, or may be generally represented by Structure 8B shown below, according to another embodiment of the invention, merely by way of example.

enzyme substrate has a dye component and a substrate moiety component, selection or preparation of which is now described.

A functional fluorescent dye may be suitably functional to serve as a component of an enzyme substrate of the invention. For example, a functional fluorescent dye may already pos- Structure 8A

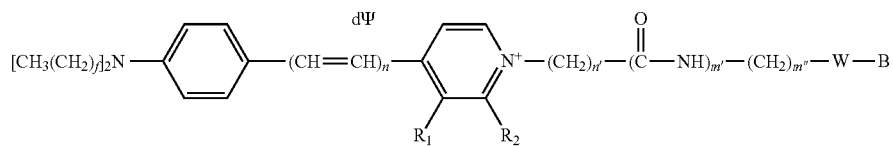

Structure 8B

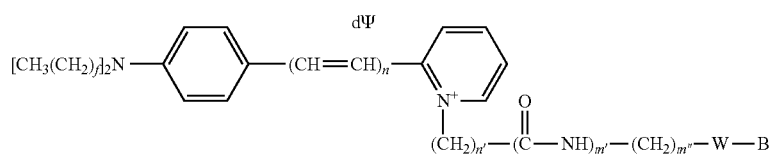

In the enzyme substrate generally represented by Structure 8A or by Structure 8B, f may be 0, 1, 2, 3, 4, 5, 6, 7, 8, 9 or 10, such as 1, 2, 3, 4, 5 or 6, for example; n may be 1, 2 or 3; n' may be 1, 2, 3, 4 or 5; m' may be 0 or 1; when m' is 0, m'' may be 1, 2, 3 or 4; when m' is 1, m'' may be 0, 2, 3 or 4; and each of W, B, ψ and d is as previously described in relation to Structure 7.

Merely by way of example, a list of membrane dye-based enzyme substrates that are generally represented by Structure 8A or Structure 8B above is provided in Table 7 of FIG. 15, along with information concerning same. Some general conventions apply to Table 7, as now described. In the column labeled "Structure," bold-faced type is used to indicate amino acid residues and SEQ ID NO: 1 is associated with a certain amino acid residue shown in bold-faced type. The general conventions that apply to the columns labeled "Cellular Localization Site of Enzyme Substrate," "Cellular Site of DYE or DYE-B'," and "$\lambda_{abs}/\lambda_{em}$ (nm/nm)" of Table 7 are generally those previously described in relation to Table 3. All of the enzyme substrates shown in Table 7 may be used in a cell-free system.

Enzyme Substrate Comprising Other Functional Fluorescent Dye

Any of a number of enzyme substrates of the invention may be prepared from functional dyes, other than those described herein, in a manner or using a method such as described herein. Any of a number of suitable functional dyes, such as a fluorescent dye-labeled receptor ligand, a lysosome dye, a Golgi dye, and/or the like, merely by way of example. For example, a fluorescent lysosomal dye, such as any commercially available LysoTracker dye, may comprise a basic amine group. The basic amine group may be necessary to such a dye, as protonation of the amine group may serve to trap the dye in an organelle, such that specific lysosomal staining results. The amine group, such as a primary amine, for example, may be blocked with an amino acid substrate moiety or a peptide substrate moiety to form a peptidase substrate of the invention, which on cleavage may provide the lysosomal dye. Preparation of Such Enzyme Substrates May be Understood in Relation to the Synthesis and example descriptions provided below concerning similar substrates.

Enzyme Substrate Synthesis

The synthesis of an enzyme substrate of the invention is now generally described. As previously described, such an enzyme substrate has a dye component and a substrate moiety component, selection or preparation of which is now described.

sess a suitable functional group, such as that sufficient for covalently connecting the dye to a substrate moiety molecule B, for example. Merely by way of example, each of a commercially available 9-amino-6-chloro-2-methoxyacridine and an ethidium bromide has at least one aromatic amino group that may serve as a suitable functional group. A fluorescent dye that may not possess suitable functionality may be derivatized for such functionality. For example, a fluorescent dye may derivatized such that is has a suitable functional group, such as that sufficient for covalently connecting the dye to a substrate moiety molecule B, for example. The functional group may be part of the chromophore core structure of the dye or may be attached to the dye via a linker molecule. The functional group may be any of a number of suitable functional groups, such as an amine group, a carboxylic group, a hydroxy group, and/or the like, merely by way of example. Any of various methods of derivatizing functional fluorescent dyes, such as any suitable method known in the art, may be employed. Merely by way of example, methods of preparing a fluorescent nucleic acid dye with a functional/reactive group have been disclosed in U.S. Pat. No. 5,863,753.

A substrate moiety B may be of suitable form to serve as a component of an enzyme substrate of the invention. Merely by way of example, a commercially available glycosyl substrate moiety may be of suitable form, such as a suitably protected form, as provided. A substrate moiety B may not be of suitable form, as just described, such that it may have to be prepared to have such form. For example, a substrate moiety B may have to be pre-assembled before it is coupled to the dye. Merely by way of example, when the substrate moiety B is a peptide, the peptide may be synthesized before being coupled to the dye. Further, merely by way of example, the substrate moiety B may be rendered protected relative to a subsequent coupling reaction, before the coupling reaction. Such protection may be pursued, for example, when the coupling reaction may be incompatible with one or more chemical group(s) of the substrate moiety B. Merely by way of example, in the case of a peptide substrate moiety B comprising amino acid residues with reactive side-chains, it may be useful or necessary to protect the reactive side-chains, before the coupling reaction. Further, merely by way of example, in the case of a glycosyl substrate moiety B having a hydroxyl and/or a carboxy, it may be useful or advantageous to protect any hydroxy and/or any carboxy that may be present, before the coupling reaction. In general, suitably-protected glycosyl substrate moiety molecules having suitable reactive groups are commercially available from several sources including Sigma-Aldrich Chemicals Co. (St. Louis, Mo.), or can be prepared as generally known.

An enzyme substrate of the present invention may be prepared from a suitable functional fluorescent dye component comprising a suitable functional group and a suitable substrate moiety B component comprising a suitable reactive group. These components may be obtained or prepared, as described above. These components are coupled via a coupling reaction. Any of various methods of coupling the components, such as any suitable method known in the art, may be employed. Merely by way of example, a precursor peptide substrate moiety B may be coupled to a functional dye to form a precursor peptidase substrate via any known method of amide bond formation. Further, merely by way of example, a precursor bromoglycosyl substrate moiety B may be coupled to a functional dye having a hydroxy group to form a precursor glycosidase substrate by following a Koenigs-Knor procedure or another suitable procedure. Still further, merely by way of example, phosphooxytrichloride may be coupled to a functional dye having a hydroxy group to form a precursor phosphatase substrate, which upon hydrolysis forms the final enzyme substrate.

A precursor substrate may be processed to provide a final enzyme substrate. Such processing may involve hydrolysis, as in the case just described, deprotection, and/or the like, merely by way of example. For example, a precursor peptidase substrate comprising one or more t-BOC-protected amine side-chain(s) or t-butyl ester-protected carboxylic acid side-chain(s) may be processed for deprotection using trifluoroacetic acid. Further by way of example, a precursor glycosidase substrate may be processed for deprotection, or the removal of hydroxyl-protecting acetyl group(s), using sodium methoxide or sodium ethoxide.

Although a general synthesis procedure, such as any described above, may be used to prepare an enzyme substrate of the invention, any of a number of other suitable synthesis procedures may be employed. Merely by way of example, in a synthesis of a peptidase enzyme substrate, the dye may be conjugated to the C-terminal amino acid, and subsequently, amino acid residues may be attached to the peptide substrate moiety B one at a time. Further, merely by way of example, a peptide substrate moiety B or a precursor peptide substrate moiety may be attached to a linker molecule L, which itself comprises a reactive group, and subsequently, the resulting L-B conjugate may be covalently linked to the reactive group of a functional dye. In general, selection of an appropriate or desirable preparation method may involve a consideration of the nature of the DYE, the nature of the substrate moiety B, and knowledge in the art.

Figure 16A:
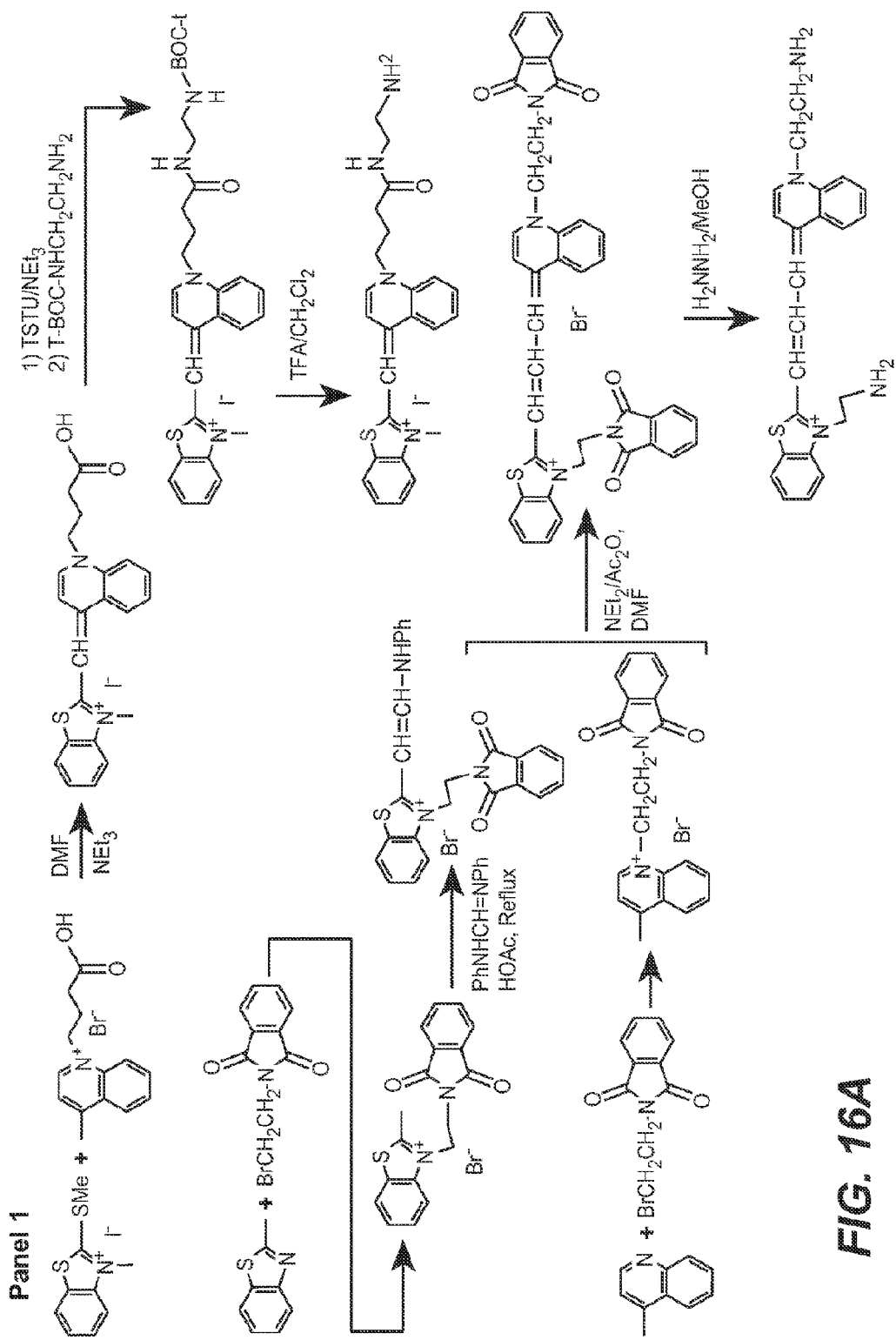
FIG. 16A is a presentation of the first part of Panel 1.
Figure 16B:
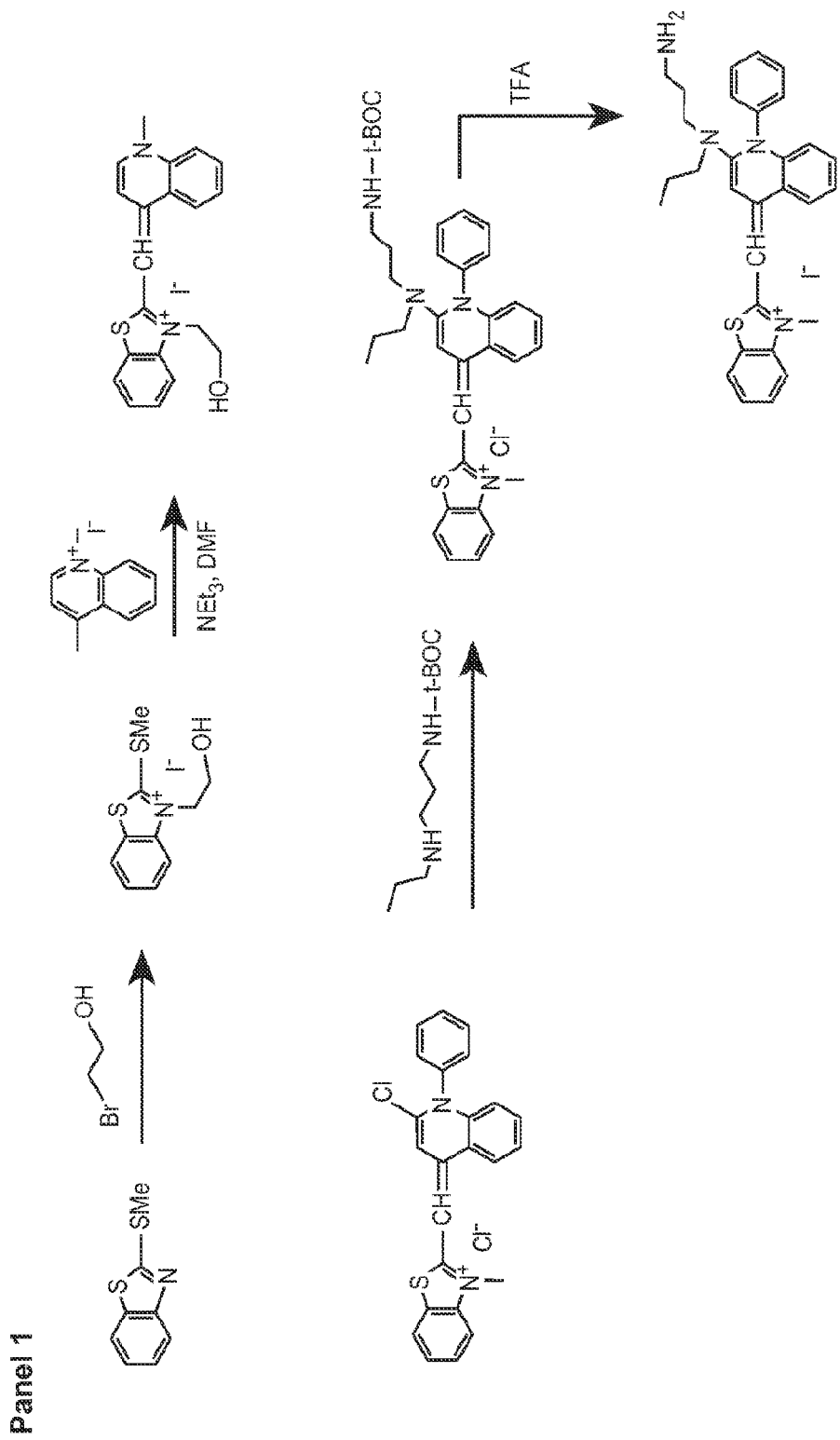
FIG. 16B is a presentation of the second part of Panel 1.

Various asymmetric cyanine dyes comprising at least one reactive group may be prepared according to various reactions that are generally represented in Panel 1 of FIG. 16. Additional information concerning the preparation of various asymmetric cyanine dyes may be found in U.S. Pat. Nos. 5,321,130, 5,436,134 and 5,863,753, and in Brooker et al., *J. Am. Chem. Soc.* 64, 199 (1942).

Figure 17:
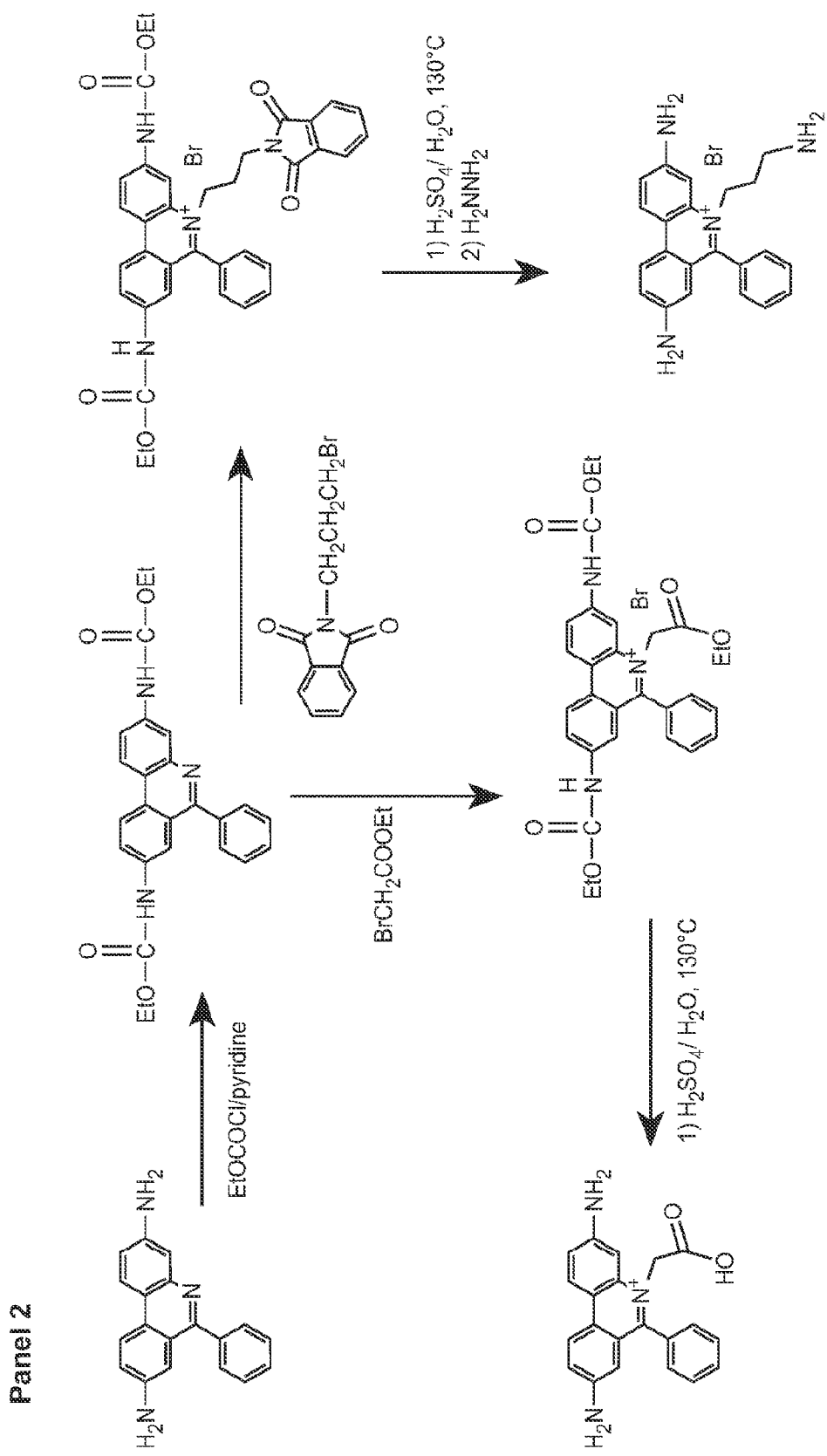
FIG. 17 is a presentation of Panel 2.

Various phenanthrodium dyes comprising at least one reactive group may be prepared according to various reactions that are generally represented in Panel 2 of FIG. 17. Additional information concerning the preparation of various phenanthrodium dyes may be found in U.S. Pat. No. 5,437,980 and references identified therein.

Figure 18A:
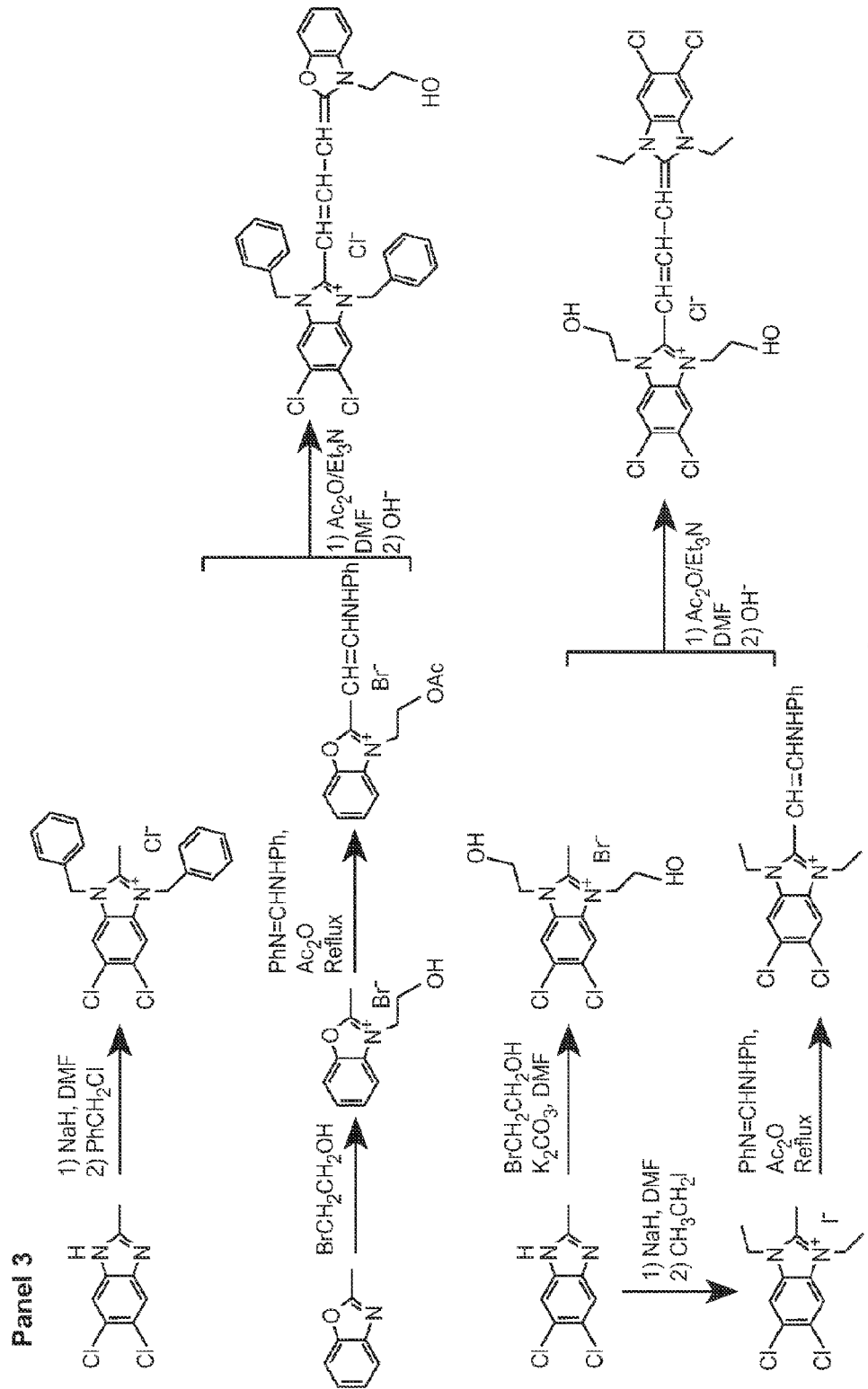
FIG. 18A is a presentation of the first part of Panel 3.
Figure 18B:
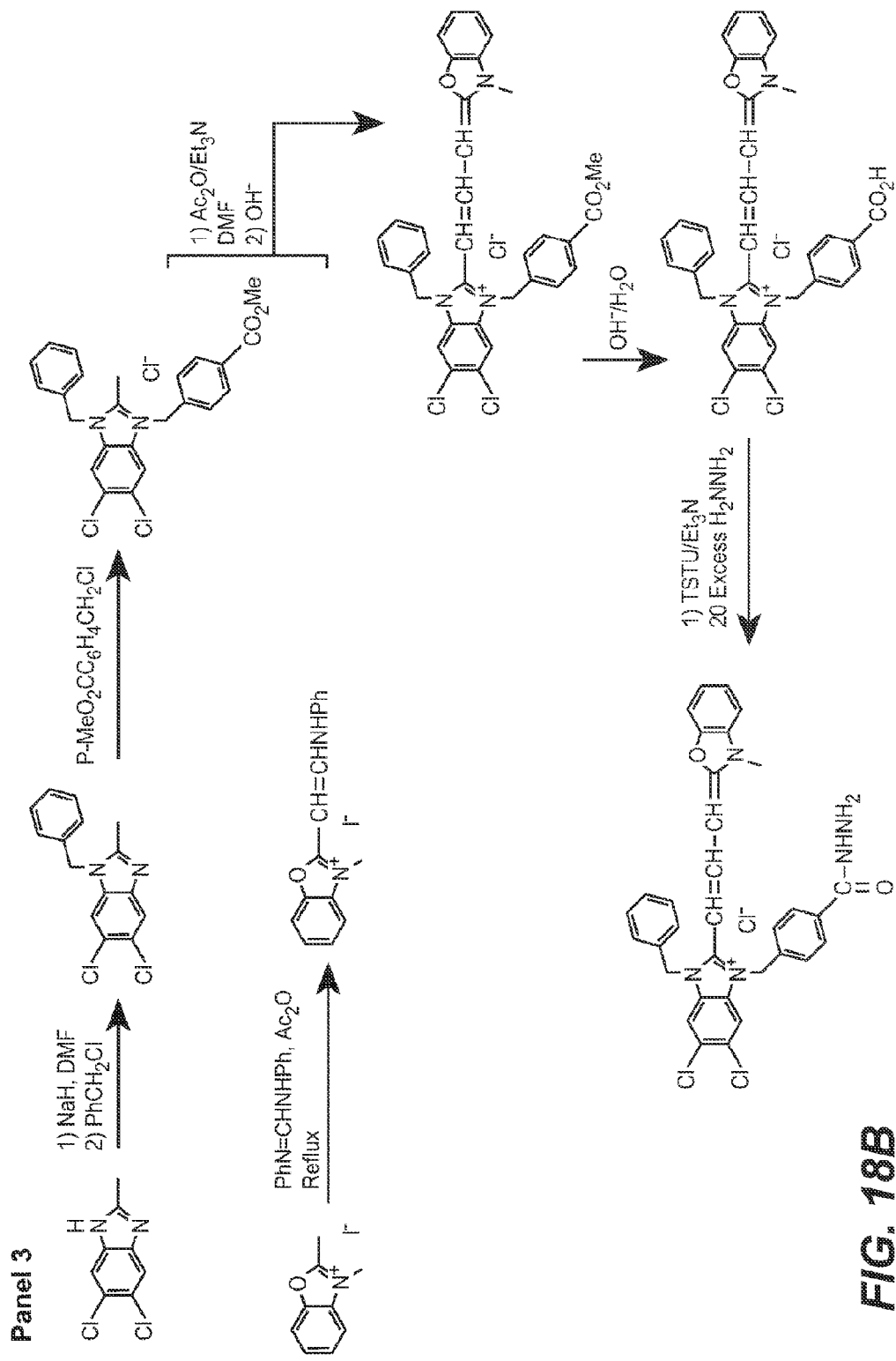
FIG. 18B is a presentation of the second part of Panel 3.

Various cyanine-based mitochondrial dyes comprising at least one reactive group may be prepared according to various reactions that are generally represented in Panel 3 of FIG. 18. Additional information concerning the preparation of various cyanine-based dyes may be found in references such as those mentioned in relation to Panel 1.

Figure 19:
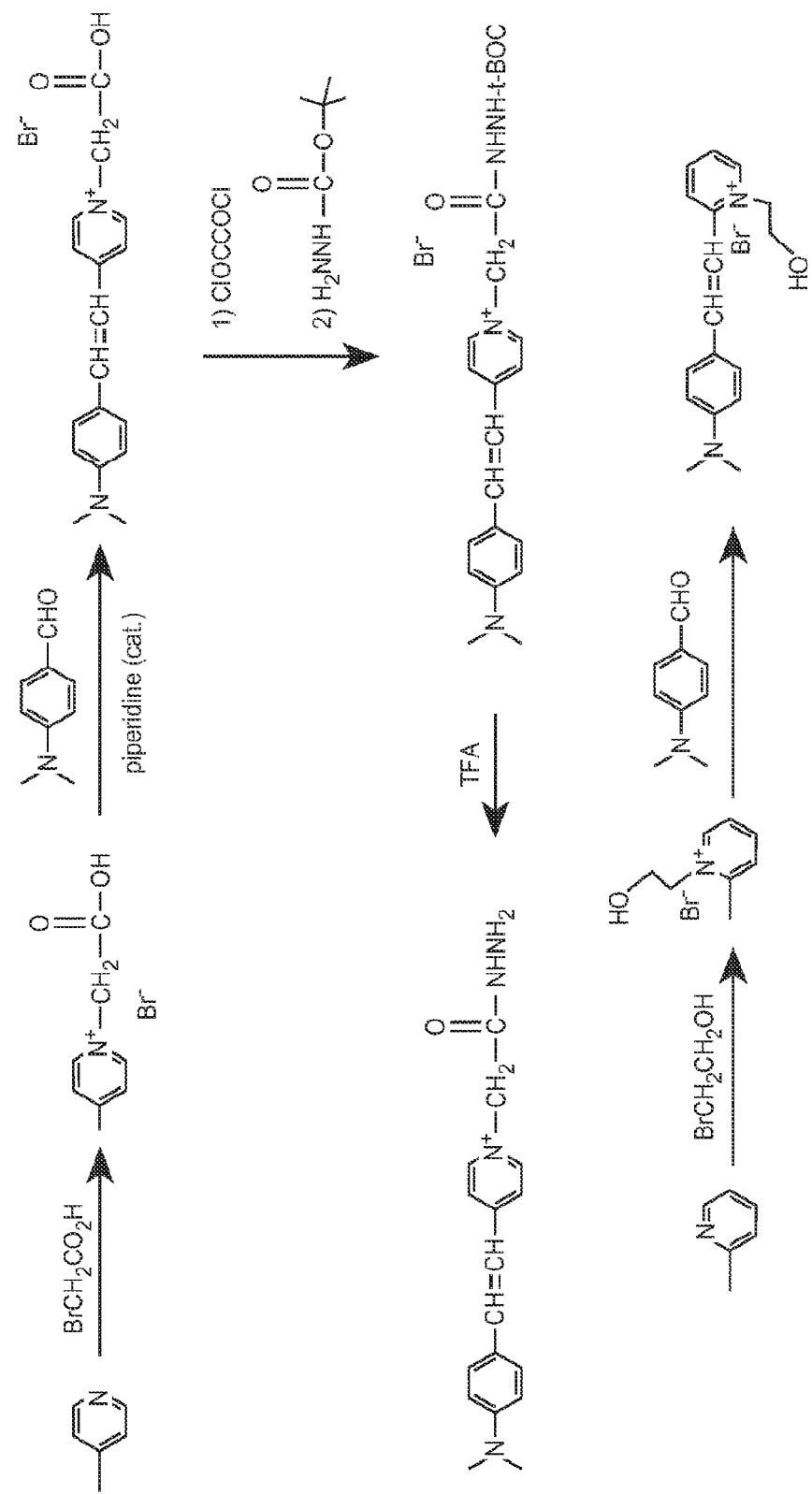
FIG. 19 is a presentation of Panel 4.

Various styryl-based mitochondrial dyes comprising at least one reactive group may be prepared according to various reactions that are generally represented in Panel 4 of FIG. 19. Additional information concerning the preparation of various styryl-based dyes may be found in Hassner et al., *J. Org. Chem.* 49, 2546 (1984).

Figure 20A:
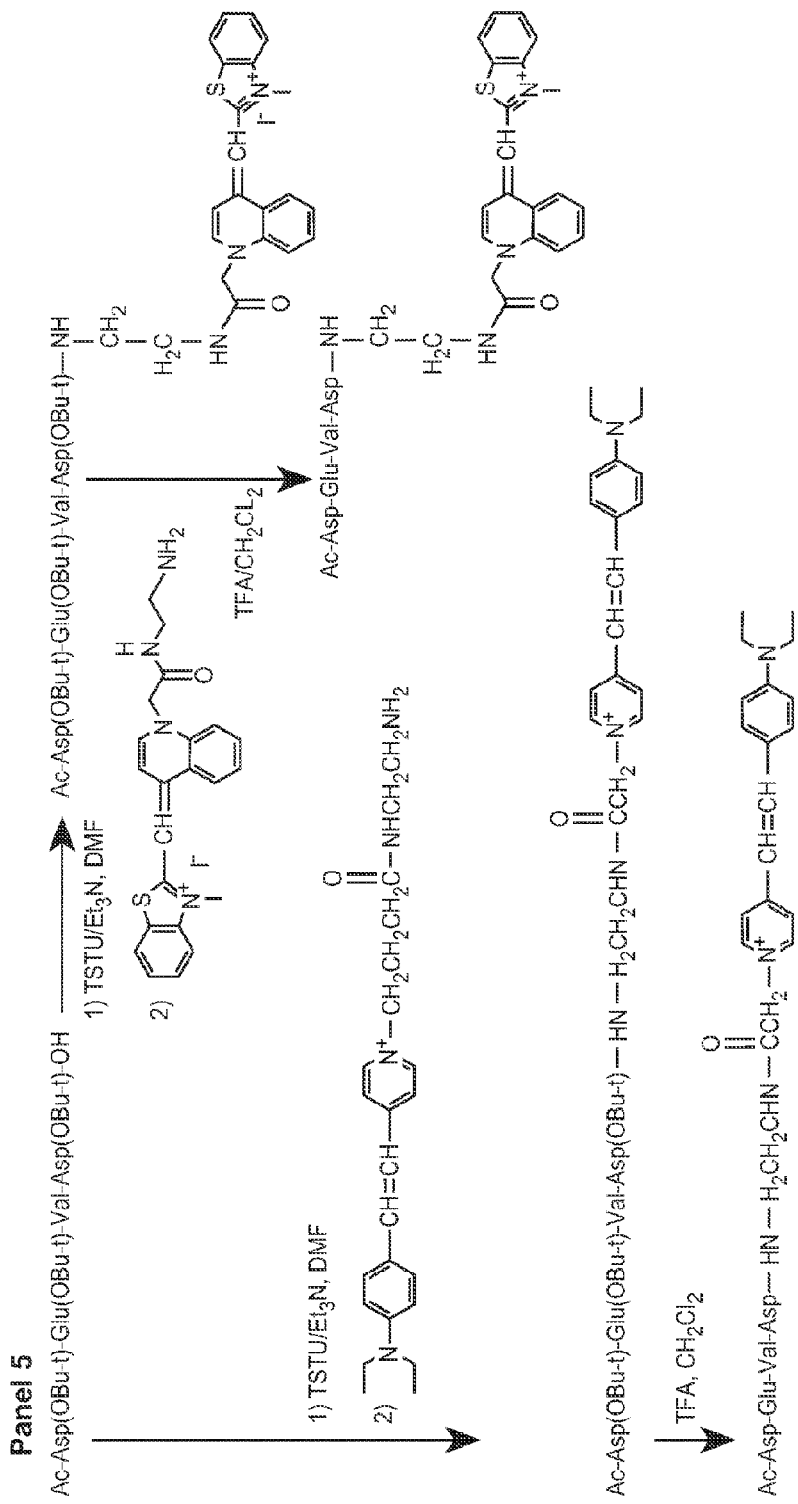
FIG. 20A is a presentation of an initial portion of Panel 5.
Figure 20B:
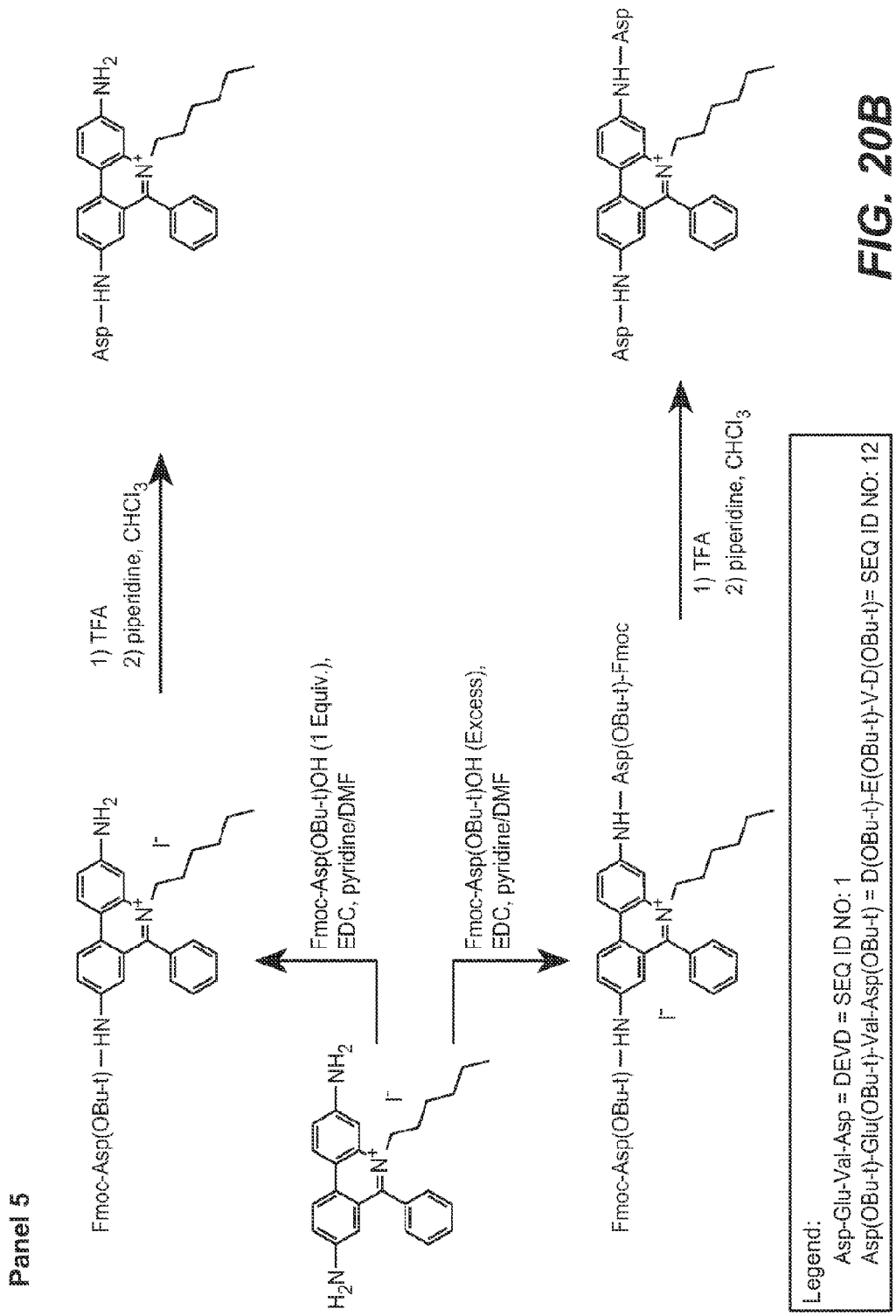
FIG. 20B is a presentation of an intermediate portion of Panel 5.
Figure 20C:
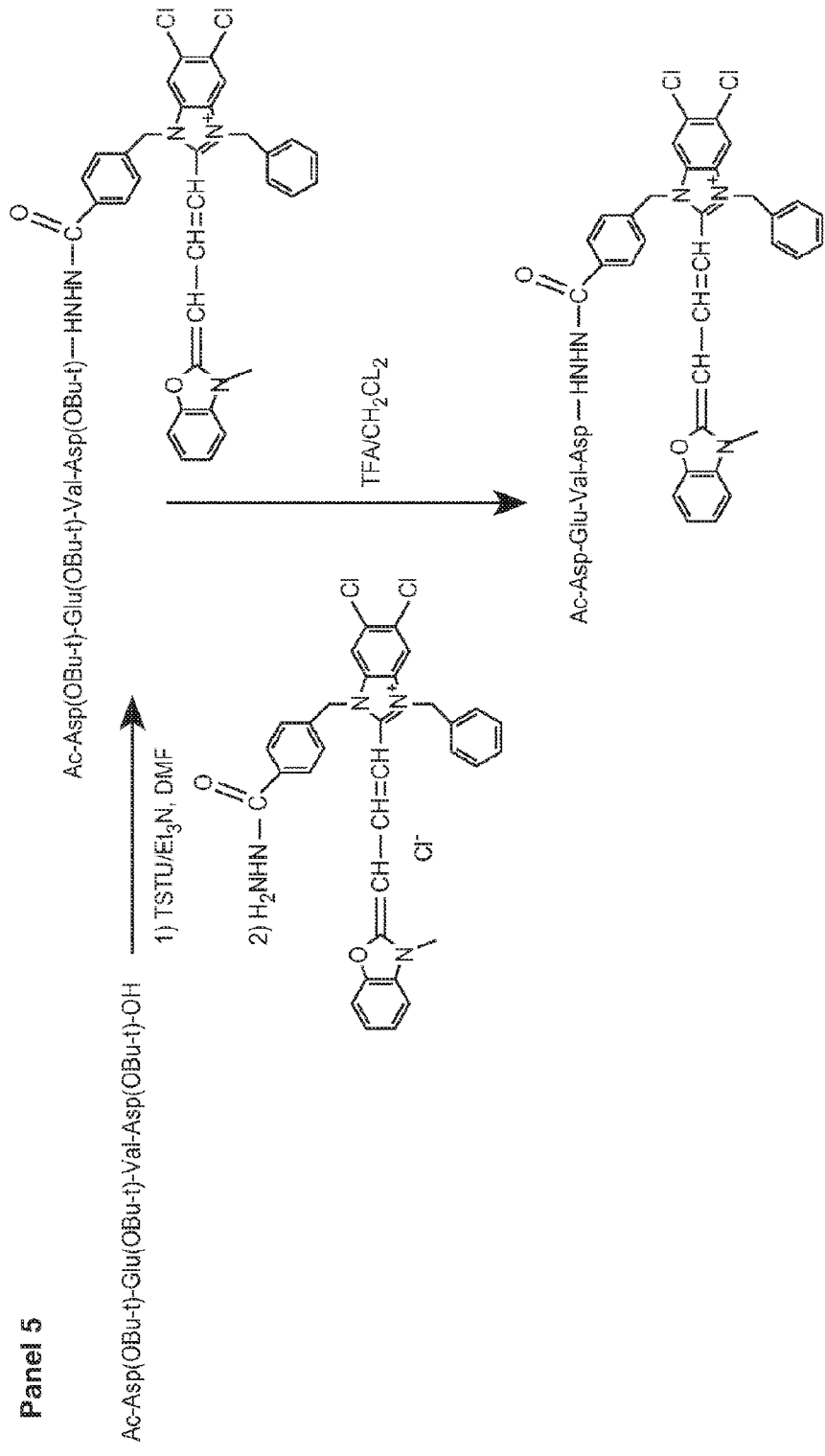
FIG. 20C is a presentation of a final portion of Panel 5.

Various peptidase substrates may be prepared using nucleic dye or mitochondrial dye according to various reactions that are generally represented in Panel 5 of FIG. 20. Panel 5 includes a legend that references Asp-Glu-Val-Asp or DEVD (SEQ ID NO: 1) and Asp(OBu-t)-Glu(OBu-t)-Val-Asp(OBu-t) or D(OBu-t)-E(OBu-t)-V-D(OBu-t) (SEQ ID NO: 12). The peptide substrate moiety Ac-Asp(OBu-t)-Glu (OBu-t)-Val-Asp(OBu-t)-OH, or Ac-D(OBu-t)-E(OBu-t)-V-D(OBu-t)-OH, where D(OBu-t)-E(OBu-t)-V-D(OBu-t) is associated with SEQ ID NO: 12, may be synthesized using techniques employed in peptide chemistry, or may be purchased from a commercial source (Zhang et al., *Bioconjugate Chem.* 14, 458 (2003). Additional information concerning the preparation of various styryl-based dyes may be found in Hassner et al., *J. Org. Chem.* 49, 2546 (1984).

Figure 21:
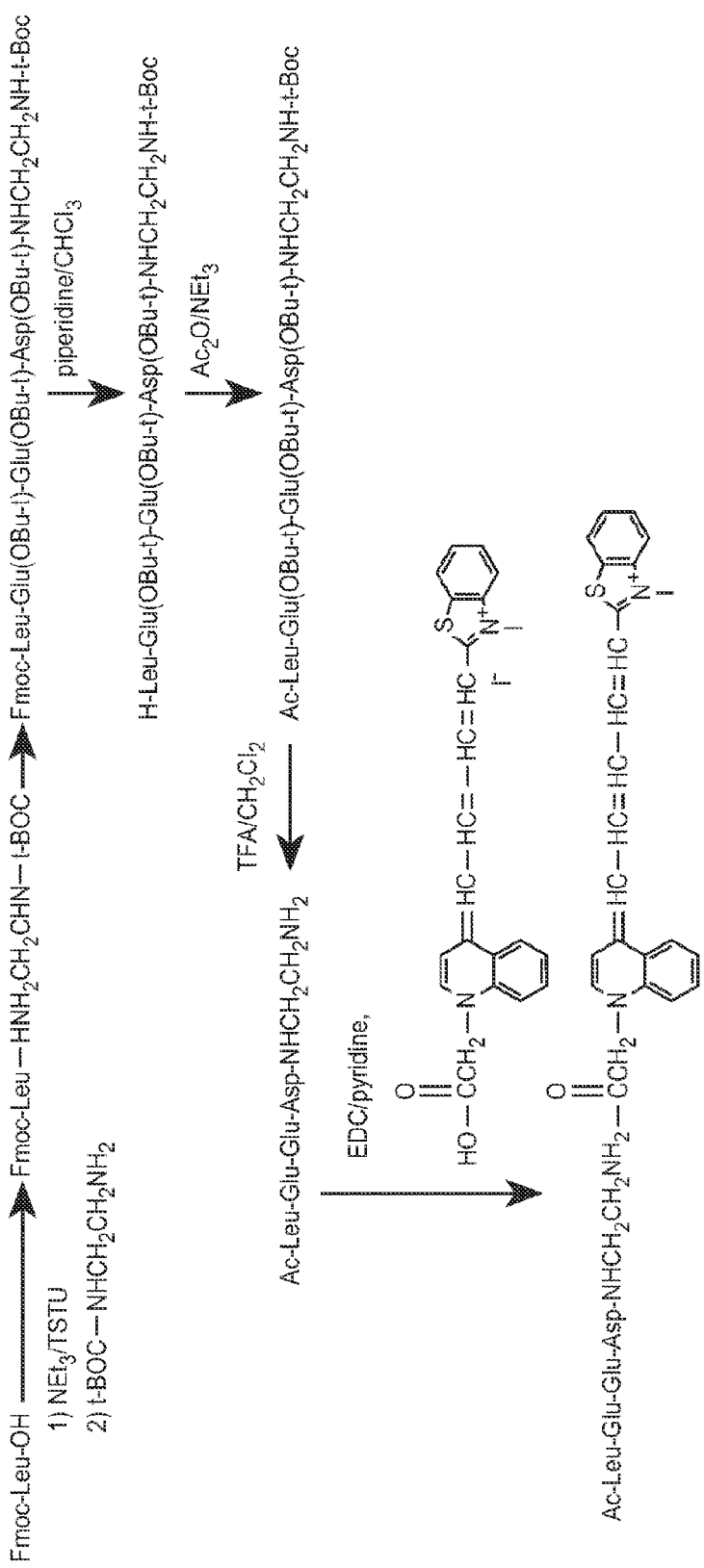
FIG. 21 is a presentation of Panel 6.

Various peptidase substrates may be prepared using a reaction that is generally represented in Panel 6 of FIG. 21. Panel 6 includes a legend that references Leu-Glu-Glu-Asp or LEED (SEQ ID NO: 3) and Leu-Glu(OBu-t)-Glu(OBu-t)-Asp(OBu-t) or L-E(OBu-t)-E(OBu-t)-D(OBu-t) (SEQ ID NO: 13).

According to the reaction generally represented in Panel 6, a precursor peptide substrate moiety B may be conjugated to a mono-protected bifunctional linker molecule and the resulting linker-precursor B may be deprotected and coupled to a dye, as generally illustrated. This method, using a common linker-precursor B, allows one to quickly prepare multiple enzyme substrates from dyes of different colors and functionalities.

Figure 22:
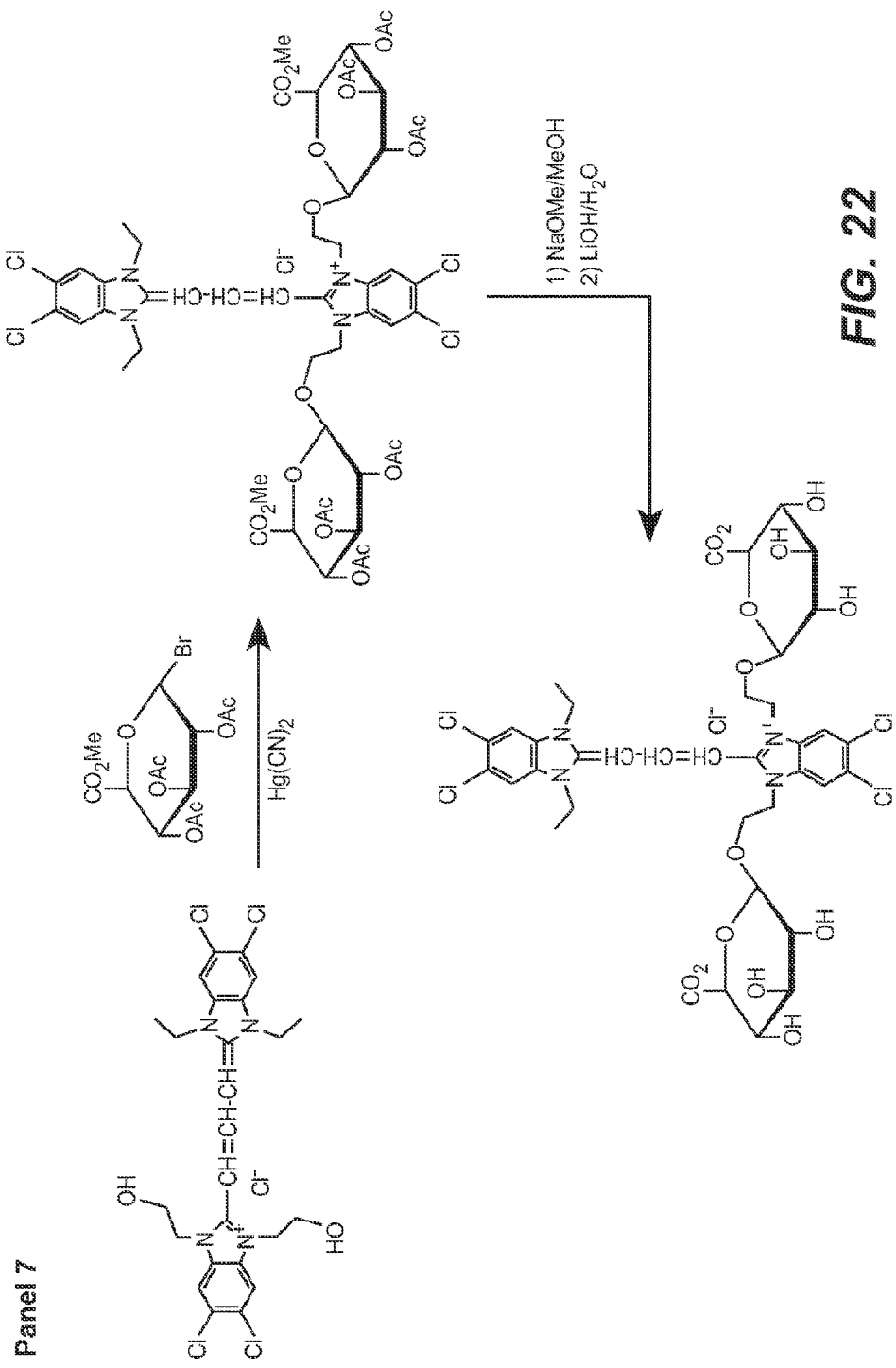
FIG. 22 is a presentation of Panel 7.

A glycosidase substrate of the invention may be prepared from a functional dye comprising at least one hydroxy group and a suitable halocarbohydrate molecule, such as a bromocarbohydrate molecule, for example, in the presence a catalyst. Methods for conjugating a halocarbohydrate to a hydroxy compound to form a glycosidic linkage have been described in U.S. Pat. Nos. 5,030,721 and 5,208,148, and in other publications (Rotman et al., *Proc. Natl. Acad. Sci. USA* 50, 1 (1963); Fernández-Santana et al., *Glycoconjugate J.* 15, 549 (1998); Křen et al., *J. Chem. Soc. Perkin Trans.* 1, 2467 (1997)). By way of illustration, the synthesis of a β-D-glucuronidase substrate from a mitochondrial dye may be carried out via a reaction that is generally represented in Panel 7 of FIG. 22.

Preparations of other enzyme substrates of the invention will be understood from the description herein and/or knowledge in the art. Merely by way of example, a phosphatase substrate of the invention may be prepared from a functional dye with a hydroxy group and phosphooxytrichloride by following a procedure described by Rotman et al., *Proc. Natl. Acad. Sci. USA* 50, 1 (1963); a sulfatase substrate of the invention may be prepared from a functional dye with a hydroxy group and chlorosulfonic acid by following a procedure of Scheigetz et al., *Organic Prep. Proc. Int.* 29, 561 (1997); and a phosphatidylinositol-specific phospholipase C substrate may be prepared as described in any of several publications, namely, Birrell et al., *Biophys. J.* 84, 3264 (2003); Zaikova et al., *Bioconjugate Chem.* 12, 307 (2001); and Rukavishnikov et al., *Bioorg. Med. Chem. Lett.* 9, 1133 (1999).

Enzyme Substrate Applications

An enzyme substrate of the invention that is specific for an enzyme or enzymes may be used to detect the activity of the enzyme or enzymes in a cell-free biological sample. In such detection, a substrate of the invention specific for the enzyme(s) and a suitable partner molecule, partner molecules, or a suitable assembly of partner molecules, which may be bound by the released functional dye, DYE or DYE-$(B')_m$, may be selected. The enzyme substrate may be placed, or dissolved, in a suitable buffer or a water-miscible organic solvent. The partner molecule, partner molecules, or assembly of partner molecules may be placed, or dissolved, in a suitable buffer. The resulting solutions may then be combined with a biological sample containing the enzyme. Fluorescence of the resulting combination may then be detected using a detection device, such as a fluorometer or a fluorescence microplate reader, for example, at wavelengths specific to the DYE or DYE-$(B')_m$. Alternatively, the enzyme substrate and the binding molecule or assembly of binding molecules may be combined in a suitable biological buffer, and the resulting combination may then be combined with the biological sample, whereupon fluorescence may be detected. In either case, the binding molecule or the assembly of binding molecules may be in an amount sufficient to saturate the functional dye, DYE or DYE-$(B')_m$, when the enzyme substrate is completely hydrolyzed.

The substrate moiety B alone or a combination of the substrate moiety B and the linkage between it and the DYE may provide the enzyme substrate with specificity for the particular enzyme(s), while the partner molecule, partner molecules, or assembly of partner molecules may provide the enzymatically-released DYE or DYE-$(B')_m$ with the binding site or sites. When the detection concerns enzyme activity in a cell-free sample, the released functional dye, DYE or DYE-$(B')_m$, may generally be a nucleic acid dye or a membrane dye, such as a mitochondrial dye or a cytoplasmic membrane dyes, for example. The binding molecule or assemblies of binding molecules may be nucleic acid(s), liposome(s), or micelle(s). According to an embodiment of the invention, the DYE or DYE-$(B')_m$ may be a nucleic acid dye and the binding molecule(s) may be nucleic acid(s), such as DNA molecule(s). Merely by way of example, a cell-free biological sample may be a cell lysate or a solution comprising, or believed to comprise, an enzyme to be detected without other cellular components from lysed cells.

Certain enzymes may be used in immunohistochemical techniques or enzyme-linked immunosorbent assays (ELISAs). In applications such as these, a fluorogenic, a chromogenic, or a chemiluminogenic enzyme substrate may be used in conjunction with an enzyme-conjugated secondary detection reagent for highly sensitive detection of an analyte. According to an embodiment of the invention, an enzyme substrate of the invention in combination with an excess of a partner molecule, partner molecules, or an assembly of partner molecules may be used in an ELISA application. Merely by way of example, the enzyme substrate may be a nucleic acid dye-based glycosidase substrate, or a nucleic acid dye-based alkaline phosphatase substrate.

An enzyme substrate of the invention that is specific for an enzyme or enzymes may be used to detect the intracellular or extracellular activity of the enzyme or enzymes in a living cell culture or living cell tissue. In such detection, a stock solution of the enzyme substrate in a buffer or a water-miscible organic solvent may be added to a standard cell culture or tissue culture. The buffer may be any of a number of suitable buffers, such as a PBS buffer, a Tris buffer, and/or the like. The water-miscible organic solvent may be any of a number of suitable such solvents, such as DMSO, DMF, methanol, ethanol, and/or the like. When an organic solvent is used, the stock solution should be of a concentration sufficient such that upon its dilution in the culture medium, the organic solvent does not interrupt cell membranes. Merely by way of example, the amount of organic solvent in the final culture medium may be about 2% or less, or about 1% or less. The cells may be incubated, such that the substrate may enter the cells and react with the enzyme. The reaction may be for a sufficient amount of time, such as on the order of about 5 minutes to about 10 hours, for example. Fluorescence may be detected via analysis of the cell culture or the tissue culture via a fluorescence microscope, a fluorescence microplate reader, a flow cytometer, and/or the like, for example. The fluorescence signal may be in the form of a change in fluorescence signal intensity at a wavelength specific to the functional dye, DYE, a fluorescence wavelength shift, a physical re-distribution of fluorescence signal within the cells, and/or the like, or any combination thereof, for example. In general, the enzymatically-released DYE or DYE-$(B')_m$ may form a cellular staining pattern that is characteristic of the cellular distribution of the partner molecule, partner molecules, and/or assembly of partner molecules. In general, washing the cell sample with a normal culture medium before examination may reduce background fluorescence from broken cells or decomposed enzyme substrate.

According to an embodiment of the invention, intracellular enzyme activity may be detected using an enzyme substrate of the invention that comprises a functional dye that is a nucleic acid dye, a mitochondrial dye, a cytoplasmic membrane dye, and/or the like. According to an embodiment of the invention, extracellular enzyme activity may detected using an enzyme substrate of the invention that comprises a functional dye, such as a membrane dye, and/or the like. The extracellular enzyme may be any suitable such enzyme, such as a gelatinase, a collagenase, a matrix metalloproteinase (MMP), and/or the like, for example.

Biological characteristics of cells and living species may be associated with the selective regulation of gene expression as a result of intrinsic developmental programs and extrinsic signals. Studies of gene expression regulation may be conducted using so-called reporter genes, which encode for easily detectable protein products, such as a fluorescent protein or an enzyme, or so-called reporter enzyme. A reporter enzyme may be detected bioluminescently or fluorescently depending on the nature of the enzyme. Firefly luciferase and *Renila* luciferase, for example, are each detected using an enzyme-specific substrate, D-luciferin and coelenterazine, respectively, which is enzymatically oxidized to produce light. Other reporter enzymes, such as β-lactamase, β-galactosidase and β-glucuronidase, may be detected fluorescently using a fluorogenic enzyme substrate specific for the enzyme. Numerous fluorogenic enzyme substrate substrates have been developed for reporter enzymes. These existing fluorogenic enzymes substrates of prior art, when applicable, release a fluorescent product that is passively trapped within cells, confined by cytoplasmic membranes. In general, the fluorescent products from these enzyme substrates merely indicate the presence of certain enzyme activity, but no additional cellular information.

According to an embodiment of the invention, an enzyme substrate comprises a functional dye that, following enzymatic cleavage, binds to a partner molecule, partner molecules, or an assembly of partner molecules. An enzyme substrate of the invention may be used in a reporter gene assay, wherein the reporter gene encodes for a reporter enzyme that hydrolyzes the substrate to release a functional dye, DYE or DYE-(B')$_m$. In general, the resulting functional dye, DYE or DYE-(B')$_m$, is not fluorescent until it binds to a partner molecule, such as DNA or RNA, for example, partner molecules, or an assembly of biological partner molecules, such as cell membranes or cellular organelles, for example. The functional dye, DYE or DYE-(B')$_m$, may provide additional cellular information by indicating the physical distribution, quantities, morphology, and/or the like, of the cellular components. According to an embodiment of the invention, an enzyme substrate of the invention that may be used for gene expression assays may be a functional dye, such as a mitochondrial dye, a lysosomal dye, an endosomal dye, a cytoplasmic membrane dye, a nucleic acid dye, and/or the like, by way of example. According to an embodiment of the invention, the functional dye may be a mitochondrial dye, a cytoplasmic membrane dye, or a nucleic acid dye. The enzyme substrates of the invention that may be used for gene expression assays may be a substrate for β-lactamase encoded by a β-lactamase gene, a β-galactosidase encoded by a lacZ gene, a β-glucuronidase encoded by a GUS gene, and/or the like, for example. According to an embodiment of the invention, a combination of an enzyme substrate of the invention and a reporter gene that encodes for a reporter enzyme may be used for high throughput screening of drug candidates, such as those whose therapeutic mechanism may involve intervening in the expression of a certain gene.

According to an embodiment of the invention, a method for determining the effect of a test substance that may be exogenously added to an enzyme is provided. In this method, the enzyme may be involved in a biological process in a test cell, the test substance may be exogenously added to the enzyme, and the effect of the test substance may be determined. Generally, such a method may comprise contacting the test cell with the test substance and the enzyme substrate of the invention that is specific for the enzyme. This may occur under various conditions, such as a condition in which the test substance interacts with an external membrane receptor of the cell or a condition in which the test substance and the enzyme substrate enter the cell, for example. The fluorescence of the text cell may be detected or recorded. The fluorescence of a control cell, which has been in contact with the enzyme substrate, but not the test substance, may also be detected or recorded. If a comparison of the fluorescence associated with the test cell and the control cell shows a difference in fluorescence, such as a difference in fluorescence intensity, fluorescence wavelength, or physical distribution, for example, such a difference may be indicative of an effect of the test substance on the enzyme. A similar method may be carried out using a reference substance that is known to have an effect on the enzyme. Comparison of the results obtained using the test substance and the reference substance may be used to evaluate, quantitatively or qualitatively, the relative effectiveness of the test substance.

According to an embodiment of the invention, an enzyme substrate of the invention that comprises a near infrared (near IR) dye, DYE, may be used for real-time in vivo imaging of any of a variety of clinically relevant targets. Generally, near IR dyes are dyes having wavelengths from about 600 nm to about 1300 nm. Merely by way of example, a suitable near IR dye, DYE, may have an absorption wavelength and an emission wavelength from about 630 to about 1200 nm. Near IR light penetrates tissues relatively easily (Wyatt et al., *Phil. Trans. R. Soc. London B* 352, 701 (1997)), such that a fluorescent IR dye may be used for optical imaging of internal tissue in a living animal, such as a human, for example. Near IR fluorescent imaging may be advantageous relative to other clinical imaging techniques for any of a number of reasons, such as multicolor imaging capability, high temporal and special resolution, avoidance of hazardous ionizing radiation, improved safety, and/or the like, for example. According to various embodiments of the invention, an enzyme substrate of the invention comprising an IR dye, DYE, may be used for, respectively, in vivo detection of enzyme activity in disease, in vivo monitoring of the efficacy of an inhibitor or an activator of an enzyme involved in a biological process, in vivo imaging of gene expression, and guiding a surgical intervention.

According to an embodiment of the invention, at least two enzyme substrates of the invention may be applied to a living cell to detect the same intracellular enzyme. In this embodiment, the substrate moiety molecules B of the enzyme substrates are specific for the same enzyme, while the functional dyes of the enzyme substrates are functionally different, such that when released, the functional dyes detect different components of the cell. Using such a method of intracellular enzyme detection, one may detect a particular intracellular enzyme and visualize multiple cellular components under a fluorescent microscope. For example, when the functionally different dyes have different fluorescence colors, multiple cellular components may be identified under a fluorescence microscope by their colors and their morphologies. Further by way of example, when the functionally different dyes have similar absorption and emission spectra, a single excitation may excite all of the functionally different dyes and the fluorescence emissions from all of these functionally different dyes may be collected within the same optical window. In general, a method of intracellular enzyme detection that employs multiple enzyme substrates, such as any of those just described, will produce a greater amount of fluorescence signal relative to a method that employs one enzyme substrate of the invention. This may be explained by the fact that in the former case, the maximal amount of fluorescence signal is not limited by the abundance of a single cellular component, as it is in the latter case.

According to an embodiment of the invention, at least two enzyme substrates of the invention may be applied to a living cell to detect the same number of intracellular enzymes. In this embodiment, each substrate moiety B of an enzyme substrate is specific for a particular enzyme, while the functional dyes of the enzyme substrates are functionally different, such that when released, the functional dyes detect different components of the cell. The functional dyes may be spectrally distinct from one another. In such a case, the presence or absence of each particular enzyme may be indicated by both the fluorescence intensity at a wavelength unique to each functional dye and by the staining of the cellular component by each functional dye.

Examples concerning enzyme substrates of the invention, and associated methods of preparation or use of same are provided below. These examples are illustrative, not limiting, as to any aspect, feature, embodiment, and/or the like, of the present invention. Other suitable modifications and adaptations of various conditions and parameters, such as those normally encountered in in vitro or in vivo assays, drug screening procedures, diagnostic procedures, and/or the like, will be appreciated as being within the spirit and scope of the invention.

EXAMPLES

Unless otherwise noted, all chemical materials used for syntheses were of at least reagent grade and were purchased

Example 1

Preparation of Compound No. 1

2-Methylbenzothiazole (4.51 g, 30 mmoles) and methyl p-toluenesulfonate (5.62 g, 30 mmoles) were mixed in a 50 mL round-bottom flask and heated at 110° C. for 24 hours. The resulting solid was triturated with ether (100 mL) and then collected by suction filtration. The collected solid was dried under vacuum at room temperature for 24 hours to give Compound No. 1, namely, 2,3-dimethylbenzothiazolium p-toluenesulfonate.

Example 2

Preparation of Compound No. 2

A suspension of Compound No. 1 (1.1 g, 3.28 mmoles) and N,N'-diphenylformamidine (1 g, 5.1 mmoles) in $Ac_2O$ (3 mL) was stirred at about 110° C. for about 1 hour. The reaction mixture was cooled to room temperature and then poured into ether (50 mL). The solid was collected from the solution by suction filtration and then dried under vacuum to give Compound No. 2, as generally represented by the structure below.

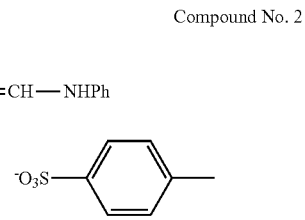

Compound No. 2

Example 3

Preparation of Compound No. 3

A mixture of lepidine (5 g) and 4-bromobutyric acid ethyl ester (5 equivalents) was heated at 130° C. for 24 hours. The oily product was thoroughly triturated with ethyl acetate, suction filtered and then dried under vacuum to give the Compound No. 3, as generally represented by the structure below.

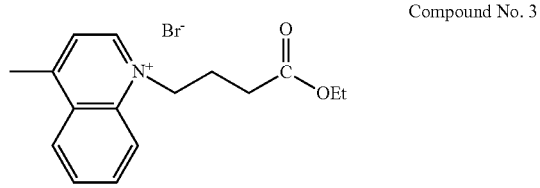 [SMILES: CCOC(=O)CCC[n+]1ccc(C)c2ccccc21 ; [Br-]]

Compound No. 3

Example 4

Preparation of Compound No. 4

Compound No. 4 was prepared from lepidine (5 g) and of 6-bromohexanoic acid (5 equivalents), using the general procedure described above in relation to Example 3.

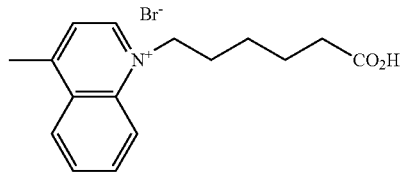

Compound No. 4

Example 5

Preparation of Compound No. 5

A mixture of 2-methylmercaptobenzothiazole and an equal molar amount of methyl p-toluenesulfonate was heated at 120° C. overnight. The resulting solid was crushed and briefly stirred in ethyl acetate. The resulting solid was collected from the resulting mixture by filtration and then dried under vacuum for 24 hours to give Compound No. 5, namely, 3-methyl-2-methylmercapto-benzothiazolium p-toluenesulfonate.

Example 6

Preparation of Compound No. 6

A mixture of Compound No. 4 (1 g) and an equal molar amount of Compound No. 5 were dissolved in dry DMF (15 mL) to give a solution. Three equivalents of triethylamine were added to the solution, and the resulting solution was stirred at room temperature overnight. The resulting orange solution was poured into a solution of NaI (10 equivalents) dissolved in water (100 mL). The resulting mixture was briefly stirred and suction filtered to collect the product, which was then dried under vacuum at 45° C. for 24 hours. The crude product was purified on a silica gel column eluted with $MeOH/CHCl_3$ (5%-20%) to give Compound No. 6, as generally represented by the structure below, which was an orange-colored solid. Compound No. 6 is an example of a nucleic acid dye comprising a carboxylic acid functional group.

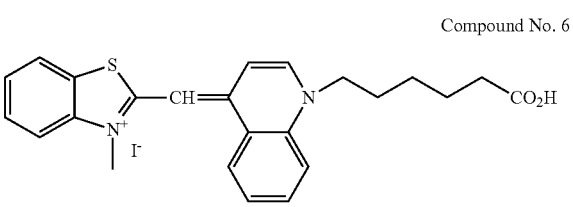 [SMILES: C[n+]1c(C=C2C=CN(CCCCCC(=O)O)c3ccccc32)sc2ccccc21 ; [I-]]

Compound No. 6

Example 7

Preparation of Compound No. 7

A solution of Compound No. 6 (1 g) dissolved in dry DMF (25 mL) was prepared. An equivalent of each of triethylamine and TSTU were added successively to the solution. After about 20 minutes of stirring, an equivalent of mono-t-Boc-ethylenediamine (Quanta Biodesign, Ltd., Powell, Ohio) in DMF (2 mL) was added dropwise. The solution was continuously stirred at room temperature for about 3 to about 4 hours and then poured into a solution of NaI (10 equivalents) in water (150 mL). A solid was collected from the resulting solution by suction filtration and then dried under high vacuum for 24 hours at 45° C. The solid was resuspended in dichloromethane (20 mL) and stirred in an ice/water bath. Trifluoroacetic acid (about 5 mL) was added dropwise to the stirred solution. Stirring continued until TLC (20% MeOH/CHCl₃/silica plate) showed completion of the deprotection reaction (about 2 to about 3 hours). The solvent was removed by rotary evaporation. A resulting gummy solid was triturated repeatedly with ether until an orange chunky solid was obtained. This solid was isolated by centrifugation and then dried under high vacuum at room temperature to give Compound No. 7, as generally represented by the structure below. Compound No. 7 is an example of a nucleic acid dye comprising an amine functional group.

Compound No. 7

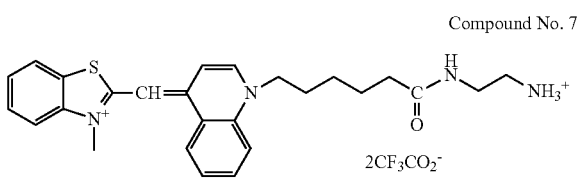 [SMILES: C[n+]1c(C=C2C=CN(CCCCCC(=O)NCC[NH3+])c3ccccc32)sc2ccccc21]

Example 8

Preparation of Compound No. 8

A solution of Fmoc-Asp(OBu-t)OH (366 mg, 0.89 mmole) in dry DMF (about 6 mL) cooled in an ice/water bath was prepared and magnetically stirred. Triethylamine (124 μL, 0.89 mmole) and HBTU (340 mg) (Dublin, Calif.) were added successively to the stirred solution. After one hour of stirring at 0-4° C., the solution was added portion-wise to a stirred solution of Compound No. 7 (400 mg) in pyridine. The resulting solution was stirred until TLC (10% MeOH/CHCl₃/silica plate) showed completion of the coupling reaction (about 1 hour). The solution was added to a stirred solution of NaI (4 g) in water (120 mL). A precipitate was collected from the solution and dried under vacuum for 24 hours. The crude product was purified on a silica gel column eluted with MeOH/CHCl₃ (5%-15%). The purified Fmoc-protected compound was suspended in CHCl₃ (8 mL). Piperidine (about 2 mL) was added to the suspension and the resulting solution was stirred until the deprotection was complete as shown by TLC (about 2 hours). The solvent and excess piperidine were removed by rotary evaporation to give a pure amino intermediate. This intermediate was coupled to the three remaining Fmoc-protected amino acids (Fmoc-Val-OH, Fmoc-Glu(OBu-t)OH and Fmoc-Asp(OBu-t)OH), one at a time, using the same procedure used for coupling the first amino acid Fmoc-Asp(OBu-t)OH, to give Compound No. 8, as generally represented by the structure below.

Compound No. 8

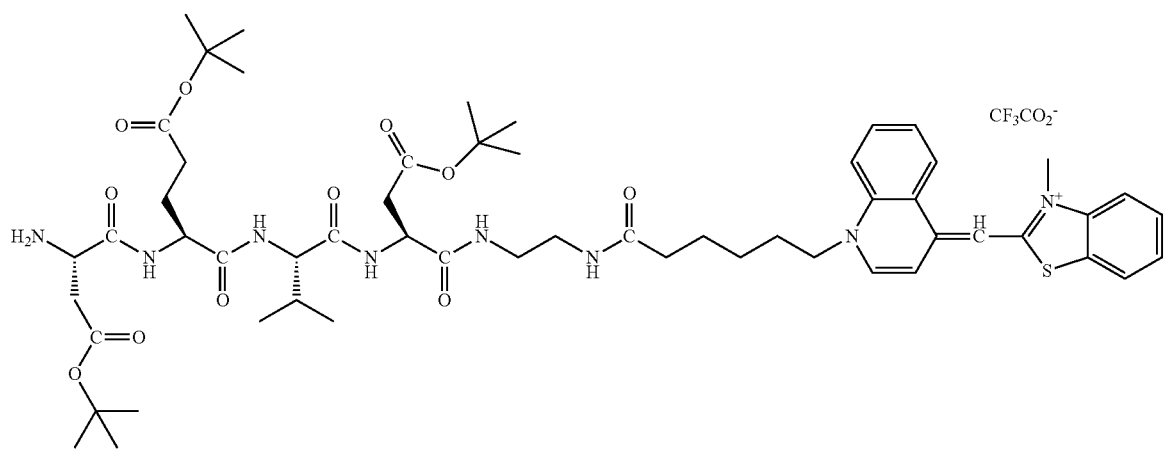

Example 9

Preparation of Compound No. 9

A solution of Compound No. 8 dissolved in DMF (5 mL) and pyridine (3 mL) was prepared and stirred. Acetic anhydride (about 1.5 mL) was added dropwise to the stirred solution. After overnight stirring, the solution was poured into a solution of NaI (3 g) in water (100 mL). A precipitate was collected from the mixture by suction filtration and then dried under high vacuum for 24 hours at room temperature. The crude product was purified on a silica gel column eluting with MeOH/CHCl₃ (5-15%) to give Compound No. 9, as generally represented by the structure below.

Compound No. 9

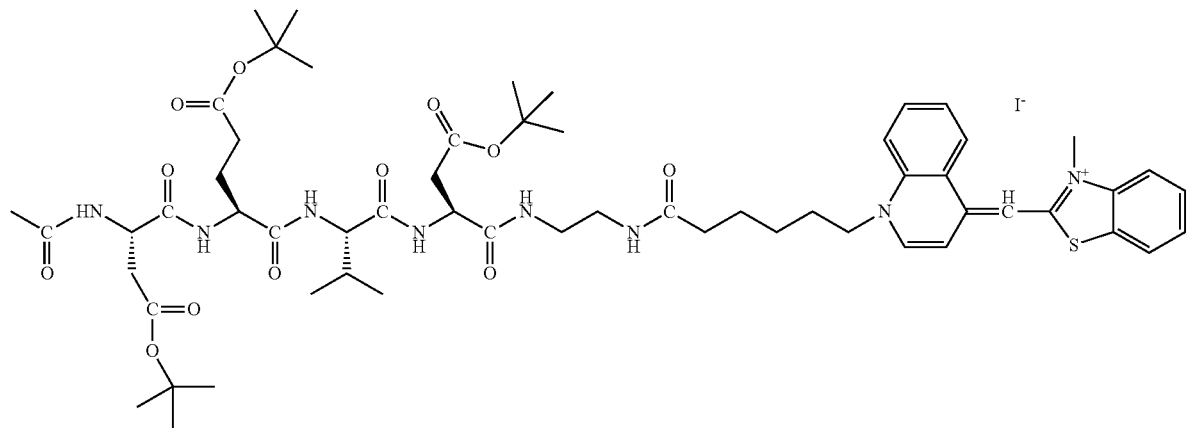

Example 10

Preparation of Substrate No. 19

A suspension of Compound No. 9 (0.35 g) in CH$_2$Cl$_2$ (16 mL) was prepared and stirred in an ice/water bath. Trifluoroacetic acid (50%, 8 mL) was added to this suspension. The resulting solution was continuously stirred for one hour at 0-4° C. and then 5 hours at room temperature. The solvent was removed from the solution by rotary evaporation and the residue was triturated with ether three times. The resulting solid was isolated by centrifugation and then dried under vacuum to give Compound No. 19, as generally represented by the structure below. HPLC of this product indicated 95% purity. Substrate No. 19 and information concerning same may be found in Table 4.

pension of Glu(OBu-t)OH (13.5 g, 66.4 mmoles) (Advanced ChemTech, Inc., Louisville, Ky.) in DMF (75 mL) and pyridine (75 mL). The resulting mixture slowly turned into a homogenous solution on continued stirring. After about 24 hours of stirring at room temperature, the solvent was removed from the solution under high vacuum at room temperature. A solution of citric acid monohydrate (about 14 g) in water (about 300 mL) was added to the resulting residue. The resulting mixture was thoroughly mixed and then extracted with ethyl acetate (about 500 mL). The ethyl acetate layer was washed with water (2×150 mL) and brine (150 mL) and then dried with anhydrous sodium sulfate. Evaporation of the solvent gave a white solid dipeptide compound, Compound No. 10, namely, Fmoc-Asp(OBu-t)-Glu(OBu-t)-OH.

Substrate No. 19

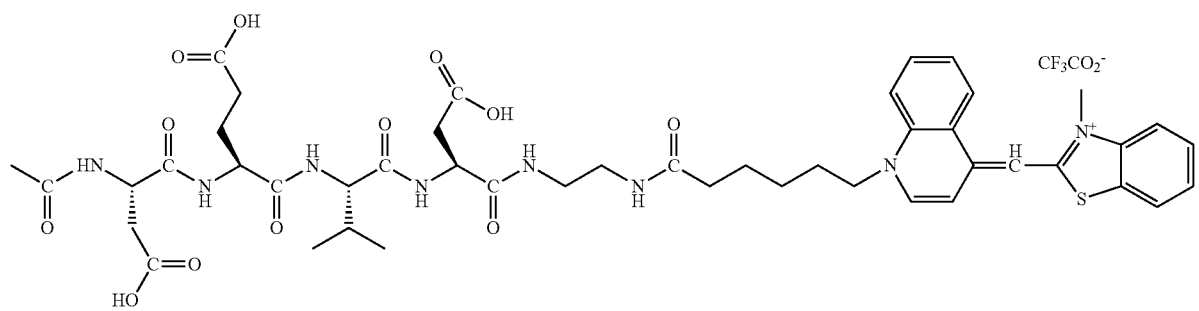

Example 11

Preparation of Compound No. 10

A solution of Fmoc-Asp(OBu-t)OH (27.3 g, 66.4 mmoles) in dry DMF (200 mL) was prepared and stirred at 0-4° C. Small portions of triethylamine (9.2 mL, 66.4 mmoles) were added to the solution, followed by a portion-wise addition of TSTU (20 g, 66.4 mmoles). After one hour of continued stirring, the solution was added portion-wise to a stirred sus-

Example 12

Preparation of Compound No. 11

Fmoc-Asp(OBu-t)OH (10.17 g) was activated using triethylamine and HBTU as generally described above in relation to Example 8 and then reacted with CBZ—NHCH$_2$CH$_2$NH$_3$$^+$Cl$^-$ in the presence of triethylamine (1 equivalent) in DMF using standard peptide coupling conditions. TLC showed that the reaction was complete in about 4 hours. The resulting mixture was poured into water (500 mL). A resulting solid was collected from the resulting solution by suction filtration and then redissolved in ethyl acetate (about 300 mL). The ethyl acetate solution was washed with brine (200 mL) and then dried with anhydrous Na₂SO₄. Following rotary evaporation of ethyl acetate, the Fmoc-protected compound was redissolved in CHCl₃ (about 100 mL) and then deprotected with piperidine using the general procedure described above in relation to Example 8. Evaporation of the solvent and excess piperidine gave Compound No. 11, namely, H-Asp(OBu-t)-NHCH₂CH₂NH—CBZ.

Example 13

Preparation of Compound No. 12

Compound No. 11 and Fmoc-Val-OH were coupled and the resulting conjugate was deprotected to give a crude product using the general procedure described above in relation to Example 8. The product was further purified on a silica gel column eluted with MeOH/EtOAc (5%) to give Compound No. 12, namely, H-Val-Asp(OBu-O—NHCH₂CH₂NH—CBZ.

Example 14

Preparation of Compound No. 13

Compound No. 10 and Compound No. 12 were coupled and the resulting conjugate was deprotected to give a crude product using the general procedure described above in relation to Example 8. The product was further purified on a silica gel column eluted with MeOH/CHCl₃ to give Compound No. 13, namely, H-Asp(OBu-t)-Glu(OBu-t)-Val-Asp(OBu-t)-NHCH₂CH₂NH—CBZ, or H-D(OBu-t)-E(OBu-t)-V-D(OBu-t)-NHCH₂CH₂NH—CBZ, where D(OBu-t)-E(OBu-t)-V-D(OBu-t) is associated with SEQ ID NO: 12.

Example 15

Preparation of Compound No. 14

Compound No. 14, namely, Ac-Asp(OBu-t)-Glu(OBu-t)-Val-Asp(OBu-O—NHCH₂CH₂NH—CBZ, or Ac-D(OBu-t)-E(OBu-t)-V-D(OBu-t)-NHCH₂CH₂NH—CBZ, where D(OBu-t)-E(OBu-t)-V-D(OBu-t) is associated with SEQ ID NO: 12, was prepared from Compound No. 13 using the general procedure described above in relation to Example 9.

Example 16

Preparation of Compound No. 15

Compound No. 14 was hydrogenated in MeOH using 5% Pd/C (5%) to give Compound No. 15, namely, Ac-Asp(OBu-t)-Glu(OBu-t)-Val-Asp(OBu-O—NHCH₂CH₂NH₂, or Ac-D(OBu-t)-E(OBu-t)-V-D(OBu-t)-NHCH₂CH₂NH₂, where D(OBu-t)-E(OBu-t)-V-D(OBu-t) is associated with SEQ ID NO: 12.

Example 17

Preparation of Compound No. 16

Compound No. 2 and Compound No. 3 were coupled using the general procedure described above in relation to Example 6 to give an ethyl ester dye intermediate, which without further purification was hydrolyzed to a free acid using NaOH/H₂O/MeOH at room temperature. The product was isolated by precipitation using HCl and then purified on a silica gel column eluted with MeOH/CHCl₃ (5-15%) to give Compound No. 16, as generally represented by the structure below. Compound No. 16 is an example of a functional dye comprising a carboxylic acid functional group.

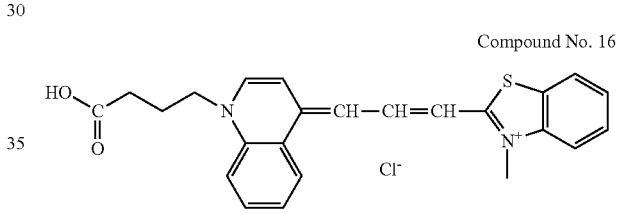

Compound No. 16

Example 18

Preparation of Compound No. 17

A solution of Compound No. 16 (95 mg, 0.18 mmol) in DMF (3 mL) at room temperature was prepared. Et₃N (30 μL, 0.22 mmol) and TSTU (54 mg, 0.18 mmol) were added to the solution. The resulting mixture was stirred at room temperature for 30 minutes and Et₃N (50 μl) and Compound No. 15 (11.7 mg, 0.16 mmol) were then added. The resulting mixture was stirred at room temperature overnight and then concentrated to dryness in vacuo. Trituration of the residue with CH₃CN gave a dark blue solid (170 mg), Compound No. 17, as generally represented by the structure below.

Compound No. 17

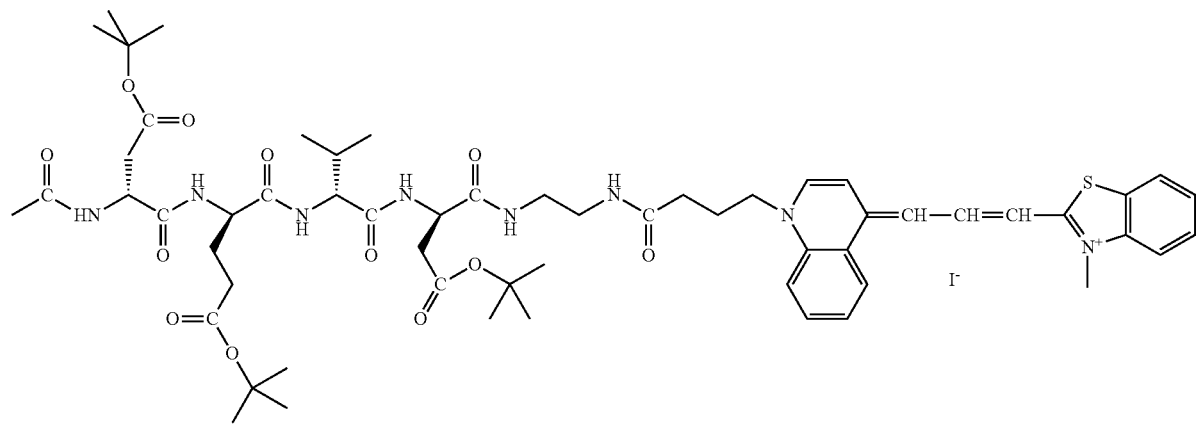

Example 19

Preparation of Substrate No. 20

A suspension of Compound No. 17 (100 mg, 0.09 mmol) in CH$_2$Cl$_2$ (8 mL) at 5° C. was prepared. TFA (2 mL) was added to the suspension. The resulting mixture was stirred at 5° C. for one hour and then at room temperature overnight. The resulting solution was concentrated to dryness in vacuo. The resulting residue was triturated with CH$_3$CN to give a dark blue solid enzyme substrate (55 mg), Substrate No. 20, as generally represented by the structure below. Substrate No. 20 and information concerning same may be found in Table 4.

Compound No. 18

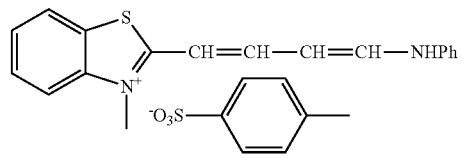

Substrate No. 20

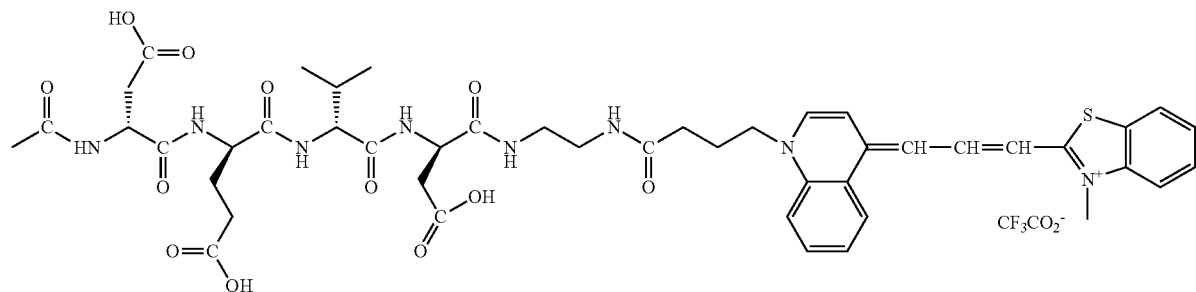

Example 20

Preparation of Compound No. 18

A mixture of Compound No. 1 (1.1 g, 3.28 mmoles) and malonaldehyde bis(phenylimine) monohydrochloride (0.85 g, 3.28 mmoles) in acetic anhydride (15 mL) was refluxed for 1 hour and then cooled to room temperature. The mixture was evaporated to dryness under high vacuum. The resulting residue was purified on a short silica gel column eluted with MeOH/CHCl$_3$ (2-10%) to give Compound No. 18, as generally represented by the structure below.

Example 21

Preparation of Compound No. 19

Compound No. 19, as generally represented by the structure below, was prepared from lepidine and bromoacetic acid using the general procedure described above in relation to Example 3.

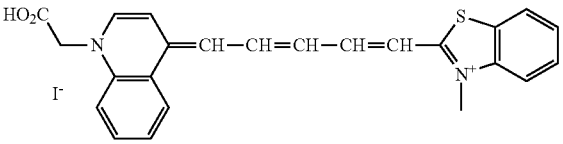

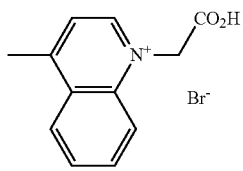

Example 22

Preparation of Compound No. 20

Compound No. 20, as generally represented by the structure below, was prepared from Compound No. 18 and Compound No. 19 using the general procedure described above in relation to Example 6. Compound No. 20 is an example a near IR asymmetrical cyanine dye having a carboxylic acid functional group.

Example 23

Preparation of Compound No. 21

A solution of BOC-Lys(Ac)-OH (100 mg, 346.8 mmol) in DMF at 5° C. was prepared. Et₃N (51 µL, 364.1 mmol) and TSTU (109 mg, 364.1 mmol) were added to the solution. The resulting mixture was stirred at 5° C. for 30 minutes and Et₃N (100 µL) and Compound No. 6 (100 mg, 148.3 mmol) were then added. The resulting mixture was stirred at 5° C. for 2 hours and then at room temperature for one hour. The solution was poured into a solution of NaI (0.5 g) in water (50 mL). A solid was collected from the mixture and then purified by column chromatography to give a dark blue solid (37.9 mg), Compound No. 21, as generally represented by the structure below. Compound No. 21 is an example of a substrate for HDAC.

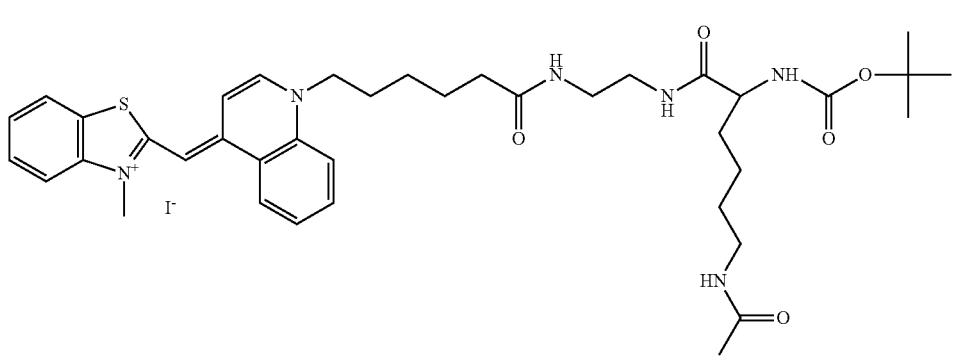

Example 24

Preparation of Compound No. 22

Compound No. 22 (98.1 mg), as generally represented by the structure below, was prepared from BOC-Lys(FMOC)—OH (128 mg, 426.8 mmol) and Compound No. 6 (125.8 mg, 186.6 mmol) using the general procedure described above in relation to Example 23.

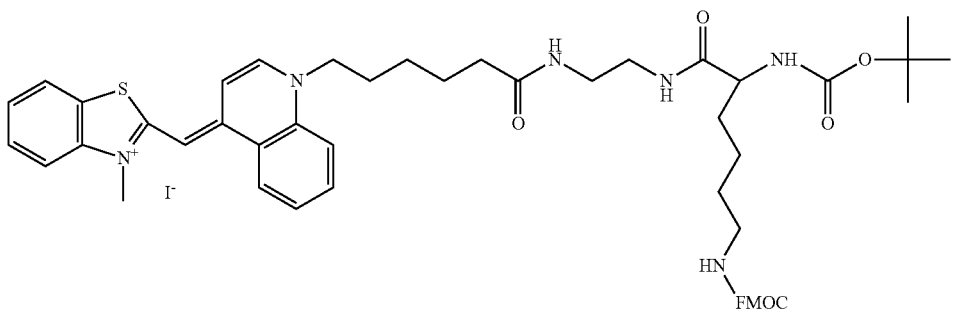

Compound No. 22

Example 25

Preparation of Compound No. 23

A solution of Compound No. 22 (90 mg) in CHCl$_3$ (2 mL) was prepared. Piperidine (100 µl) was added to the solution. The resulting mixture was stirred at room temperature for 2 hours and then concentrated to dryness in vacuo. The resulting residue was stirred as a suspension in EtOAc (5 mL) for one hour and a resulting precipitate (20 mg) was collected by suction filtration to give Compound No. 23, as generally represented by the structure below.

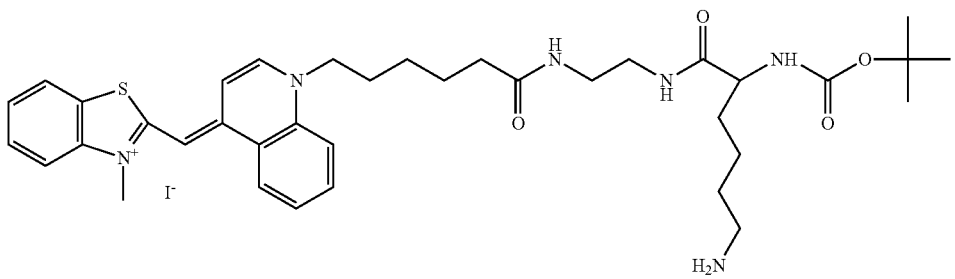

Compound No. 23

Example 26

Preparation of Substrate No. 5 and Substrate No. 6

A solution of Z-Ala-Ala-OH (600 mg, 2 mmol) in DMF (5 mL) and pyridine (5 mL) at 0° C. was prepared. EDAC (410 mg, 2.1 mmol) was added to the solution. The resulting mixture was stirred at 0° C. for 15 minutes and ethidium bromide (EB) (200 mg, 0.5 mmol) was then added. The resulting mixture was stirred at 0° C. for one hour and then at room temperature overnight. The resulting solution was concentrated to dryness in vacuo and the resulting residue was purified by column chromatography on silica gel to give a dark red solid (155 mg), Substrate No. 5, as generally represented by the structure and legend below, and another dark red solid (70 mg), Substrate No. 6, as generally represented by the structure and legend below, namely, (Z-Ala-Ala)-2-EB (70 mg). Each of Substrate No. 5 and Substrate No. 6, and information concerning same, may be found in Table 2.

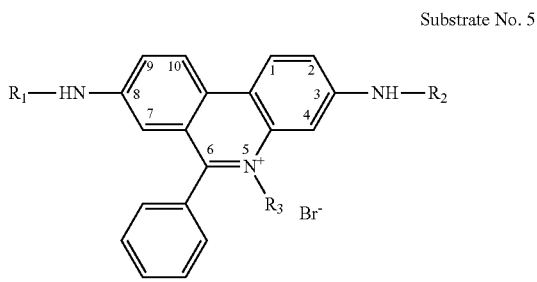

Substrate No. 5

Legend: R₁ = Z-Ala-Ala- and R₂ = H

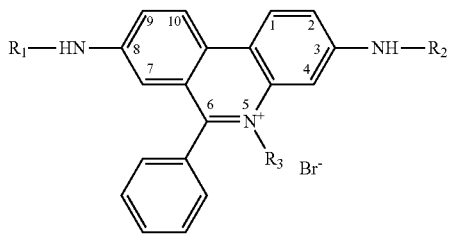

Substrate No. 6

Legend: R₁ = R₂ = Z-Ala-Ala-

Example 27

Preparation of Compound No. 24

Compound No. 24 (56 mg), as generally represented by the structure below, was prepared from Compound No. 16 (128.3 mg) using the general procedure described above in relation to Example 7.

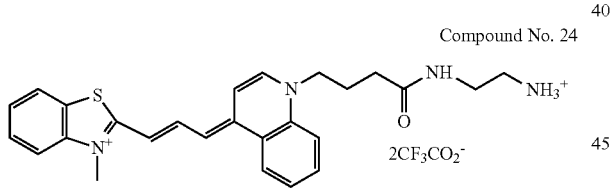

Compound No. 24

Example 28

Preparation of Compound No. 25

A suspension of sodium hydride (60% weight purity) (101 mg, 2.52 mmol) in DMF (5 mL) at 0° C. was prepared. 2-methyl-5,6-dichlorobenzimidazole (507.6 mg, 2.52 mmol) was added to the suspension in one portion. The resulting mixture was stirred at 0° C. for 30 minutes and benzyl chloride (290 µL, 2.52 mmol) was added. The resulting mixture was then stirred at room temperature overnight and concentrated to dryness in vacuo. The resulting residue was purified by column chromatography on silica gel using $CHCl_3$:EtOAc:hexanes=3:3:4 as the solvent to give an off-white solid (500 mg), Compound No. 25, as generally represented by the structure below.

Compound No. 25

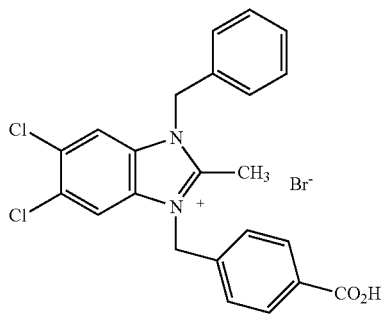

Example 29

Preparation of Compound No. 26

A mixture of Compound No. 25, namely, 1-benzyl-2-methyl-5,6-dichlorobenzimidazole (250 mg, 0.86 mmol), and 4-(bromomethyl)benzoic acid (500 mg, 2.15 mmol) in chlorobenzene (5 mL) was heated at 120° C. overnight. The resulting mixture was allowed to cool to room temperature, EtOAc (20 mL) was added, and the resulting suspension was refluxed gently for 2 hours. Compound No. 26 (326 mg), as generally represented by the structure below, was collected from the refluxed suspension by suction filtration.

Compound No. 26

Example 30

Preparation of Compound No. 27

A solution of Compound No. 26 (200 mg, 0.32 mmol) and 2-(2-anilinovinyl)-1-methylbenzoxazolium iodide (150 mg, 0.59 mmol) (prepared from 2-methylbenzoxazole using the general procedure described above in relation to Example 2) in DMF (3 mL) was prepared. Acetic anhydride (110 µL, 1.20 mmol) and $Et_3N$ (250 µL, 1.71 mmol) were added to the solution. The resulting solution was stirred at room temperature for 7 hours and EtOAc (5 mL) was added. The resulting suspension was stirred at room temperature overnight and a solid product (200 mg), Compound No. 27, as generally represented by the structure below, was collected from the suspension by suction filtration. Compound No. 27 is an example of a membrane dye comprising a carboxylic acid functional group.

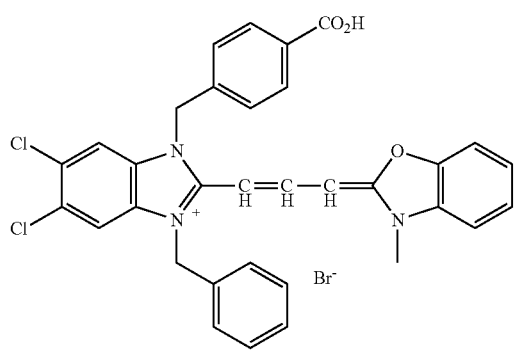

Compound No. 27

Example 31

Preparation of Compound No. 28

A solution of Compound No. 27 (100 mg, 0.15 mol) in DMF (2 mL) was prepared. Et$_3$N (25 µL, 0.18 mmol) and TSTU (45 mg, 0.15 mmol) were added to the solution. The resulting mixture was stirred at room temperature for 30 minutes and Et$_3$N (75 µL) and tert-butyl carbazate (29 mg, 0.18 mmol) were added. The mixture was stirred at room temperature overnight and then poured into a solution of NaI (0.5 g) in water (50 mL). A precipitate was collected from the resulting solution and then purified on silica gel using MeOH/CHCl$_3$. The purified compound was dissolved in CH$_2$Cl$_2$ (5 mL) and stirred at 5° C. TFA (1 mL) was added to the cooled solution. The resulting mixture was stirred at 5° C. for 2 hours and then concentrated to dryness in vacuo. The resulting product, Compound No. 28, as generally represented by the structure below, was used to prepare Compound No. 29, as described below in relation to Example 32, without further purification. Compound No. 28 is an example of a mitochondrial dye comprising a hydrazide functional group.

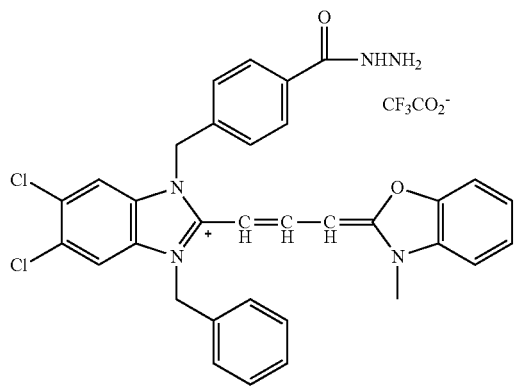

Compound No. 28

Example 32

Preparation of Compound No. 29

A solution of Fmoc-Asp(OtBu)-OH (77 mg, 0.182 mmol) in DMF (5 mL) at room temperature was prepared. Et$_3$N (30 mL, 0.21 mmol) and TSTU (55 mg, 0.185 mmol) were added to the solution. The resulting mixture was stirred at room temperature for 1 hour Et$_3$N (25 mL) and Compound No. 28 (75 mg, 0.091 mmol) were added successively. The resulting mixture was stirred at room temperature overnight and then poured into a solution of NaI (0.5 g) in water (about 50 mL). A precipitate was collected from the resulting solution and then purified by column chromatography on silica gel to give an orange solid (95 mg), Compound No. 29, as generally represented by the structure below.

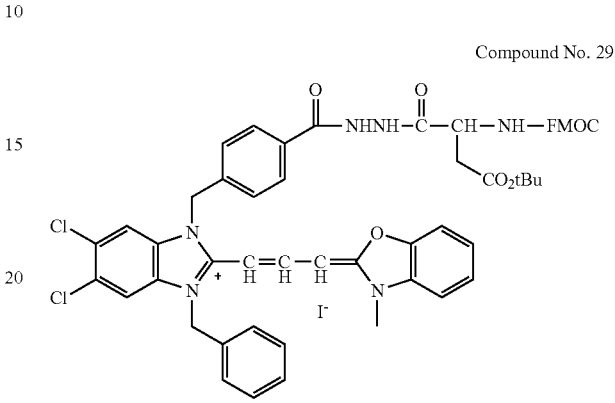

Compound No. 29

Example 33

Preparation of Substrate No. 47

A solution of Compound No. 29 (75 mg) and piperidine (0.5 mL) in CHCl$_3$ (3 mL) was stirred at room temperature for 3 hours. The resulting solution was concentrated to dryness in vacuo. The resulting residue was redissolved in CH$_2$Cl$_2$ (5 mL) and TFA (1 mL) was added to the resulting solution. The resulting mixture was stirred at room temperature overnight and then concentrated to dryness in vacuo. The resulting residue was triturated with EtOAc to give an orange solid enzyme substrate (45 mg), Substrate No. 47, as generally represented by the structure below. Substrate No. 47 and information concerning same may be found in Table 6.

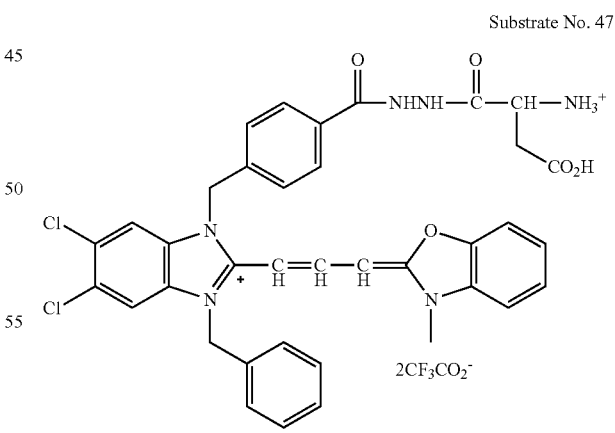

Substrate No. 47

Example 34

Preparation of Compound No. 30

5,6-Dichloro-2-methylbenzimidazole (5 g), 3-bromopropanol (6 equivalents) and K$_2$CO$_3$ (10 equivalents) were mixed in DMF (50 mL). The resulting mixture was stirred at 120° C. overnight and then poured into a saturated NaCl solution (about 200 mL). A solid product, Compound No. 30, as generally represented by the structure below, was collected from the resulting solution and dried under vacuum.

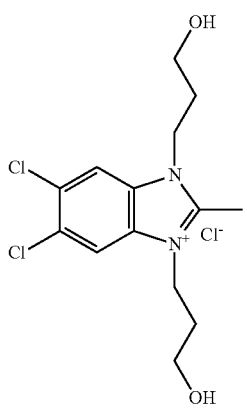

Compound No. 30

Example 35

Preparation of Compound No. 31

Compound No. 31, as generally represented by the structure below, was prepared from 5,6-dichloro-2-methylbenzimidazole and ethyl iodide using the general procedure described above in relation to Example 34.

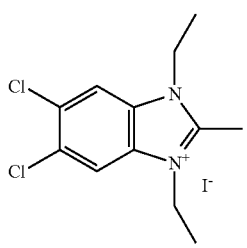

Compound No. 31

Example 36

Preparation of Compound No. 32

Compound No. 32, as generally represented by the structure below, was prepared from N,N'-diphenylformamidine (10 equivalents) and Compound No. 31 (1 equivalent) following the general procedure described above in relation to Example 2.

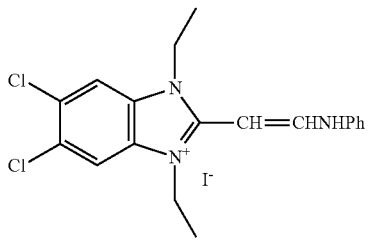

Compound No. 32

Example 37

Preparation of Compound No. 33

Compound No. 32 (1 g) and Compound No. 30 (0.7 g) were coupled using $NEt_3/Ac_2O$ via the general procedure described above in relation to Example 30. At the end of the coupling reaction, a solution of NaOH (0.5 g) in water (5 mL) was added to the resulting mixture and allowed to react for half an hour to hydrolyze any acetate form of the dye. The resulting solution was then poured into a saturated NaCl solution (100 mL). A precipitate was collected from the resulting solution and then dried under high vacuum at 50° C. for at least 24 hours to give Compound No. 33, as generally represented by the structure below.

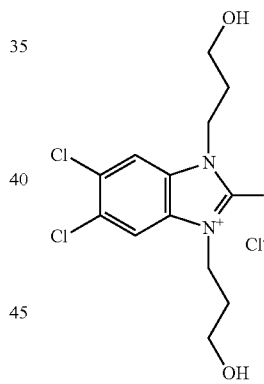

Compound No. 33

Example 38

Preparation of Compound No. 34

A mixture of Compound No. 33 (2 g, 3.2 mmoles), $Hg(CN)_2$ (2.97 g, 10.7 mmoles) and 4 Å molecular sieves (20 g) in dry $CH_3CN$ (70 mL) was stirred under nitrogen for one hour. 2,3,4-Tri-O-acetyl a-D-glucopyano-siduronic acid methyl ester (2.8 g, 7.04 mmoles) was added portion-wise to the resulting solution. The resulting mixture was stirred until TLC indicated complete reaction. The resulting mixture was suction filtered through a Celite pad to remove any precipitate. The filtrate was evaporated and the crude product, Compound No. 34, as generally represented by the structure below, was purified on a silica column eluted with MeOH/$CHCl_3$.

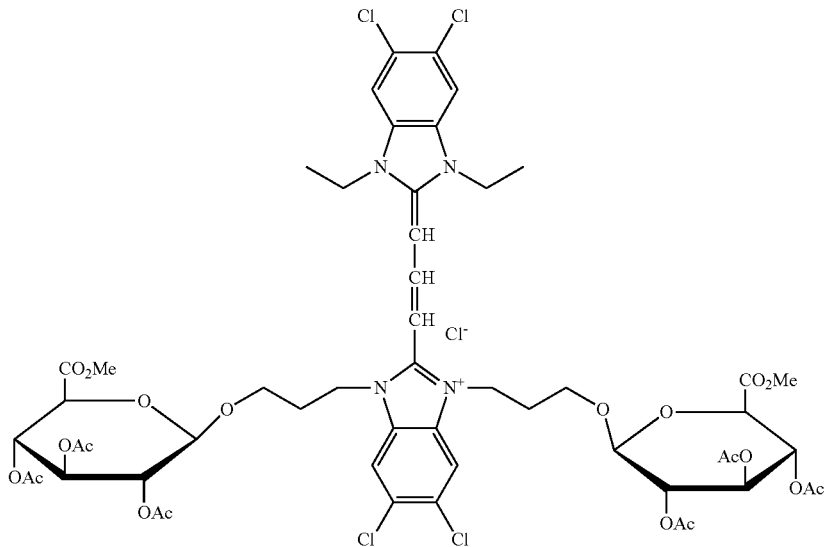

Compound No. 34

Example 39

Preparation of Compound No. 35

Compound No. 34 was deprotected using NaOMe and LiOH successively according to the general procedure described in U.S. Pat. No. 5,208,148 to give Compound No. 35, as generally represented by the structure below. Compound No. 35 is an example of an enzyme substrate for a β-glucuronidase enzyme.

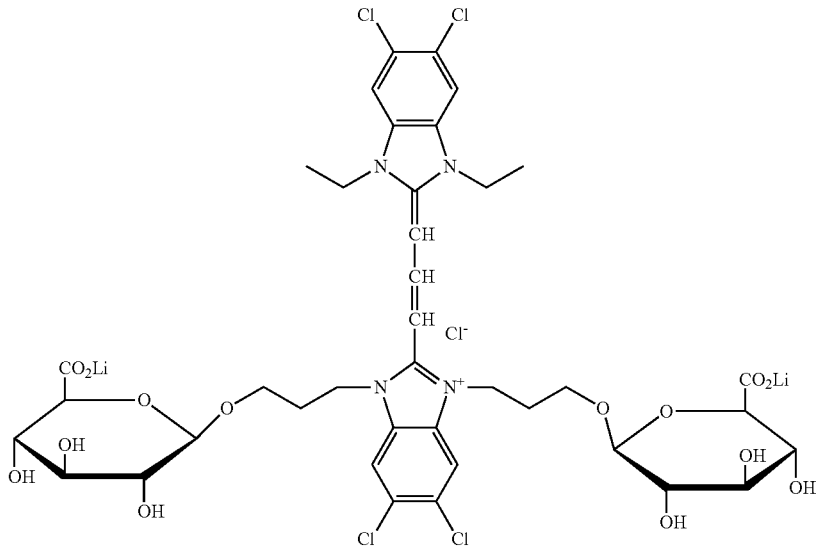

Compound No. 35

Example 40

Preparation of Compound No. 36

Compound No. 36, as generally represented by the structure below, was prepared from lepidine and 1,2-dibromoethane (20 equivalents) via the general procedure described above in relation to Example 3.

Compound No. 36

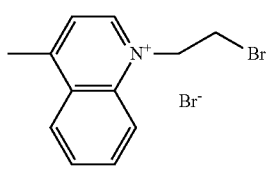

Example 41

Preparation of Compound No. 37

Compound No. 37, as generally represented by the structure below, was prepared from Compound No. 5 and Compound No. 36 via the general procedure described above in relation to Example 6.

Compound No. 37

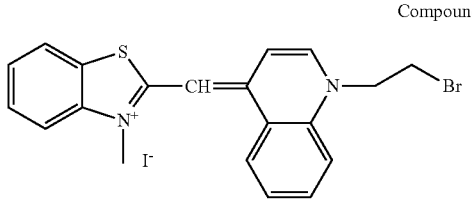

Example 42

Preparation of Compound No. 38

Compound No. 38, as generally represented by the structure below, was prepared from Compound No. 37 via treatment with KSCSOEt and then with AcNHNH$_2$ as described for thiol compounds in U.S. Pat. No. 5,955,604.

Example 43

Preparation of Compound No. 39

Compound No. 39, as generally represented by the structure below, was prepared from ACLH (Otsuka Chemical Co., Ltd., Osaka, Japan) and glutaric anhydride in the presence of triethylamine via a procedure described by Gao et al., *J. Am. Chem. Soc.* 125, 11146 (2003) for making similar compounds.

Compound No. 39

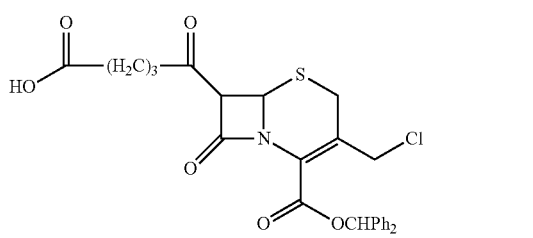

Example 44

Preparation of Compound No. 40

Compound No. 40, as generally represented by the structure below, was prepared by coupling Compound No. 38 and Compound No. 39 using a procedure similar to that described in U.S. Pat. No. 5,955,604.

Compound No. 40

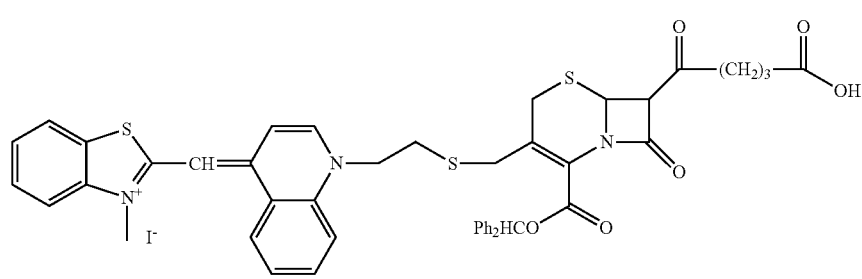

Example 45

Preparation of Compound No. 41

Compound No. 41, as generally represented by the structure below, was prepared by deprotection of Compound No. 40 using TFA/anisole as generally described by Gao et al., *J. Am. Chem. Soc.* 125, 11146 (2003). Compound No. 41 is an example of nucleic acid dye-based enzyme substrate for a β-lactamase enzyme.

Compound No. 38

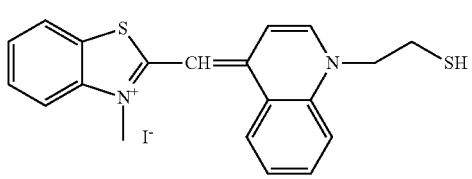

Compound No. 41

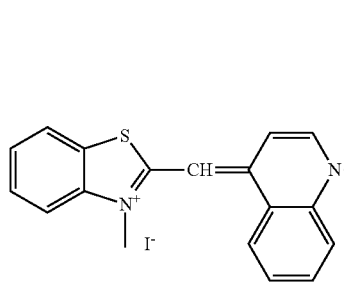

Example 46

Preparation of Compound No. 42

A mixture of picoline (10 g, 0.11 mol) and 4-bromobutyric acid (25 g, 0.15 mol) was heated at 120° C. for 5 hours. After the resulting mixture was cooled to room temperature, EtOAc (100 mL) was added and the resulting mixture was refluxed gently for 1 hour. Compound No. 42, as generally represented by the structure below, was collected from the refluxed mixture by suction filtration.

Compound No. 42

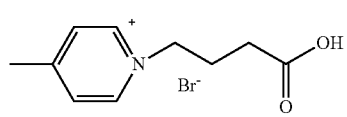

Example 47

Preparation of Compound No. 43

A mixture of 4-N,N-diethylaminobenzaldehyde (1.5 g, 8.46 mmol), Compound No. 42 (2.2 g, 8.46 mmol) and piperidine (0.1 mL, 1 mmol) in CH$_3$OH (20 mL) was stirred at reflux temperature overnight. The resulting solution was concentrated to dryness in vacuo and the resulting residue was purified by column chromatography on silica gel to give a dark red solid (3 g), Compound No. 43, as generally represented by the structure below.

Compound No. 43

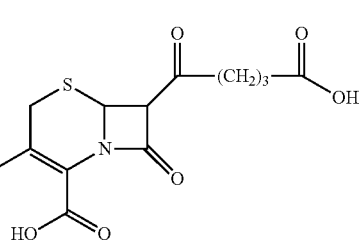

Example 48

Preparation of Compound No. 44

Compound No. 44, as generally represented by the structure below, was prepared by first coupling Compound No. 43 and Compound No. 15 according to the general procedure described above in relation to Example 18, and then deprotecting the resulting conjugate with TFA according to the general procedure described above in relation to Example 19. Compound No. 44 is an example of a membrane dye-based enzyme substrate.

Compound No. 44

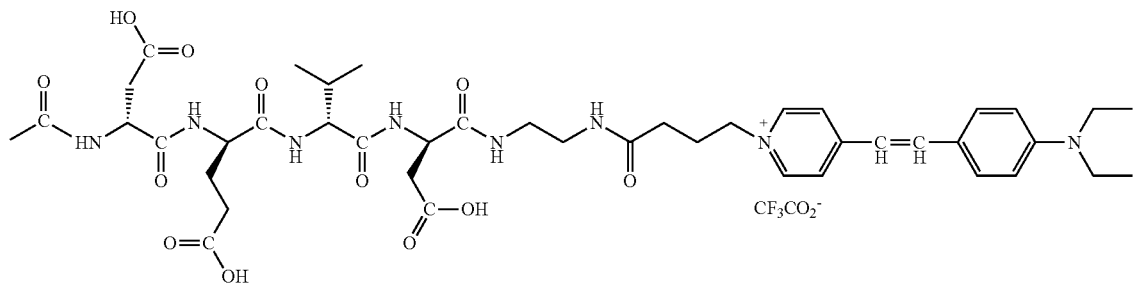

Example 49

Preparation of Compound No. 45

Compound No. 45, as generally represented by the structure below, may be prepared by coupling Compound No. 43 and the synthetic peptide Pro-Asn-Gly-Leu-Glu-Ala-D-Arg-D-Arg-D-Arg-NH$_2$ (custom-synthesized by GL Biochem (Shanghai) Ltd., Shanghai, China), or PQGLEA-D-R-D-R-D-R—NH$_2$, using the general procedure described in relation to Example 18. The resulting conjugate may be purified by preparative HPLC. Compound 45 is an example of a membrane dye-based enzyme substrate.

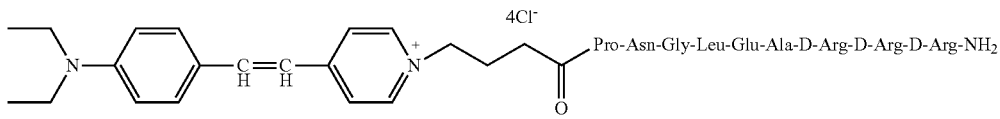

Compound No. 45

Example 50

Preparation of Compound No. 46

Compound No. 46, as generally represented by the structure below, was prepared from Compound No. 43 and mono-t-Boc-ethylenediamine according to the general procedure described above in relation to Example 7.

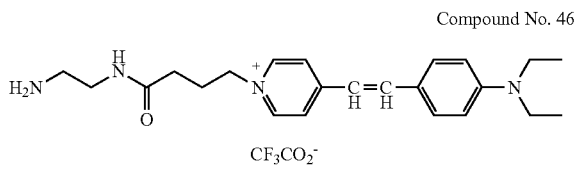

Compound No. 46

Example 51

Measurement of Fluorescence Spectra in the Presence of DNA

Stock solutions of nucleic acid dye-based substrates and respective control compounds were prepared by dissolving each compound in DMSO at 1 mg/mL concentration. The stock solutions were diluted into a pH 7.4 buffer (TE buffer) comprising Tris (10 mM), EDTA (1 mM) and NaCl (50 mM) to give a final concentration of 1 µM. Dye solutions containing an excess amount of DNA were prepared by adding a sufficient amount of calf thymus DNA calculated to yield a ratio of greater to or equal to 50 DNA base pairs per dye molecule. A fluorescence spectrum for each dye was recorded before and after the addition of DNA using a Jasco F-750 fluorescence spectrophotometer, with the fluorescence excitation wavelength set at $\lambda_A$-25 nm or 600 nm, where $\lambda_A$ is the absorption maximum for each dye in the presence or the absence of DNA, and emission collection wavelength set at 660 nm. The emission spectra associated with Substrate No. 20 and control Compound No. 24 are shown in FIG. 1. The data shows that the control Compound No. 24, the enzymatically cleaved product of Substrate No. 20, is substantially more fluorescent than Substrate No. 20 itself.

Example 52

DNA Titration of Nucleic Acid Dye-Based Substrates and Controls

Figure 2A:
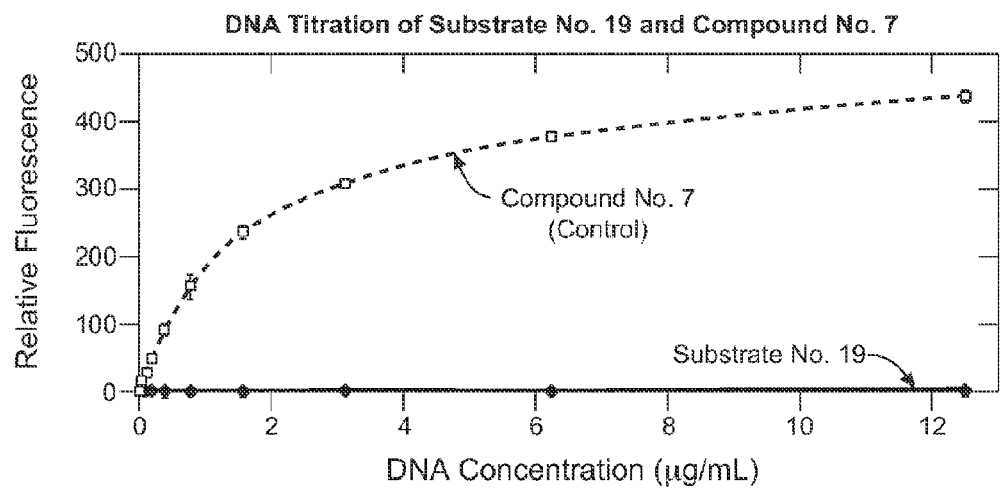
FIG. 2A is a graphical representation of relative fluorescence versus dsDNA concentration (μg/mL), or a DNA titration, of a nucleic acid dye-based substrate (Substrate No. 19, at 1 μM in TE buffer) for a caspase-3 enzyme and a control compound (Compound No. 7, at 1 μM in TE buffer), as further described in connection with Examples 7, 10 and 52.
Figure 2B:
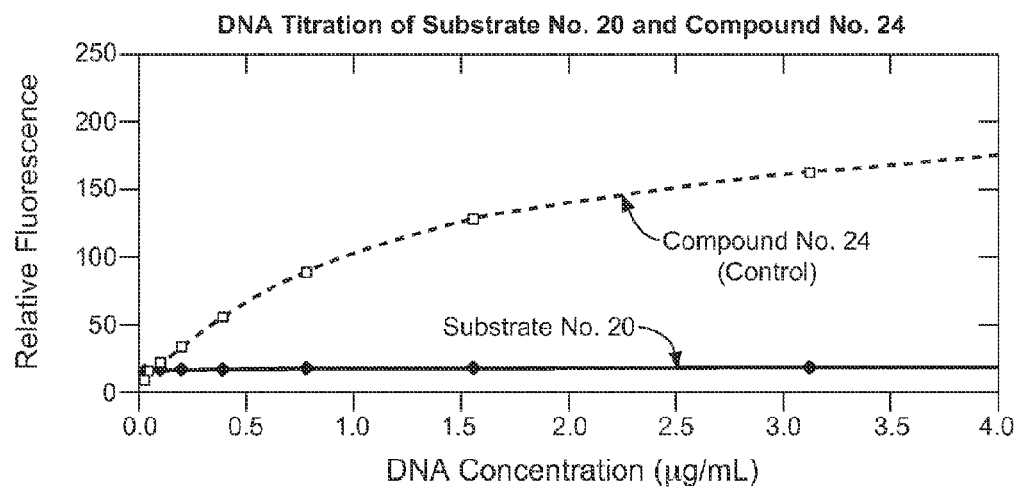
FIG. 2B is a graphical representation of relative fluorescence versus dsDNA concentration (μg/mL), or a DNA titration, of a nucleic acid dye-based substrate (Substrate No. 20, at 1 μM in TE buffer) for a caspase-3 enzyme and a control compound (Compound No. 24, at 1 μM in TE buffer), as further described in connection with Examples 19, 27 and 52.

In this example, nucleic acid dye-based caspase-3 substrates, Substrate No. 19 and Substrate No. 20, and respective control compounds, Compound No. 7 and Compound No. 24, were titrated with varying amounts of calf thymus dsDNA and the fluorescence signals of the solutions were recorded. Briefly, the substrates and the respective controls were prepared as generally described above in relation to Example 51. Multiple wells of a 96-well plate were loaded with the substrate (100 µL, 1 µM) or the respective control (100 µL, 1 µM). Each well was then titrated with 5 µL of one of the seven DNA stock solutions of 2.1, 4.1, 8.2, 16.4, 32.8 65.6 and 127.5 µg/mL concentration, respectively, in pH 7.4 TE buffer. After a 30-minute incubation at room temperature, the fluorescence reading of each well was recorded with a SpectraMax Germini XS fluorescence microplate reader (Molecular Devices Corp., Sunnyvale, Calif.), with the excitation wavelength and the emission collection wavelength set at 485 nm and 530 nm, respectively. The titration curves for each pair of substrate and control dyes are shown in FIG. 2. The data shows that the substrates are relatively insensitive to the presence of DNA over a wide DNA concentration range, while the controls, the enzymatically cleaved products of the substrates, are fluorescently responsive to the amount of DNA present.

Example 53

In Vitro Enzymatic Assay for Nucleic Acid Dye-Based Substrates for Caspase-3

Figure 3:
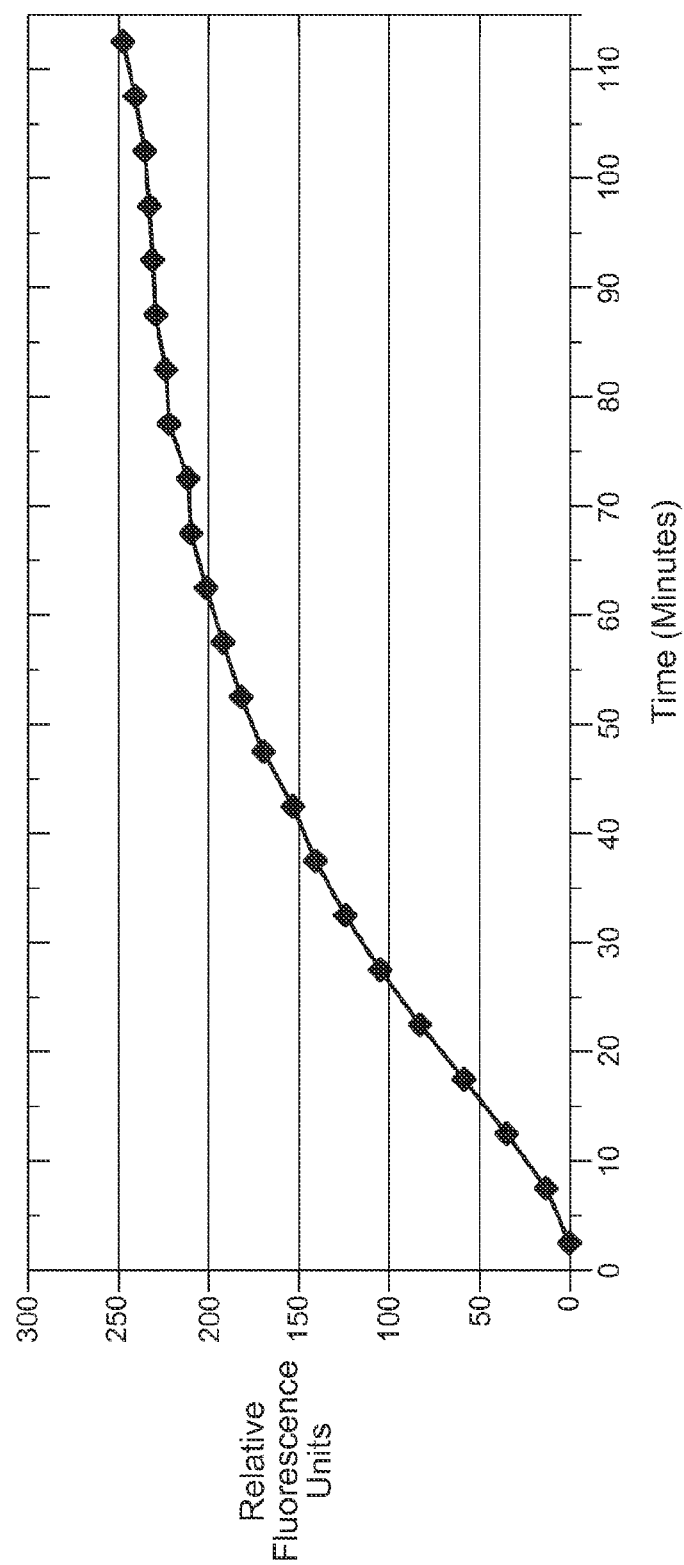
FIG. 3 is a graphical representation of relative fluorescence versus time (minutes) associated with an enzymatic assay of a nucleic acid dye-based substrate (Substrate No. 19, at 10 μM) for a caspase-3 enzyme (0.1 unit/mL) in buffer, with excitation set at 485 nm and emission collected at 530 nm, as further described in connection with Examples 10 and 53.
Figure 4A:
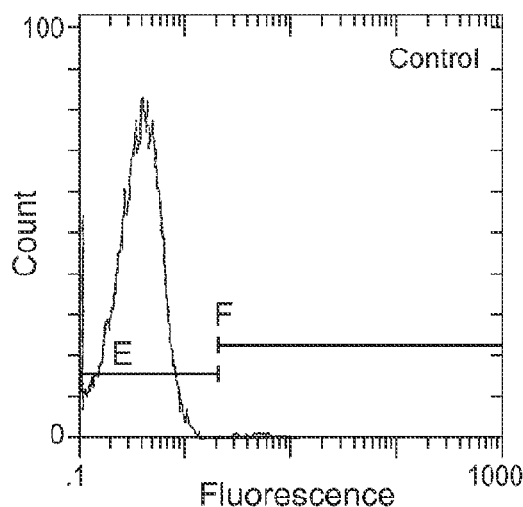
FIG. 4A is a graphical representation of a count, or number of cells, versus relative fluorescence associated with the detection of enzymatic activity of a caspase-3 enzyme in live cells via flow cytometry, using a control of uninduced Jurkat cells.
Figure 4B:
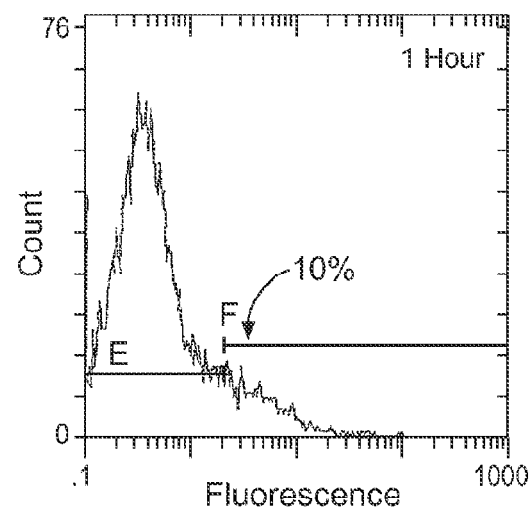
FIG. 4B is a graphical representation of a count, or number of cells, versus relative fluorescence associated with the detection of enzymatic activity of a caspase-3 enzyme in live cells via flow cytometry, using a nucleic acid dye-based substrate (Substrate No. 19, at 10 μM) for the caspase-3 enzyme that was incubated for 15 minutes with Jurkat calls that had been induced with staurosporine (at 1 μM) for 1 hour, as further described in relation to Examples 10 and 54.
Figure 4C:
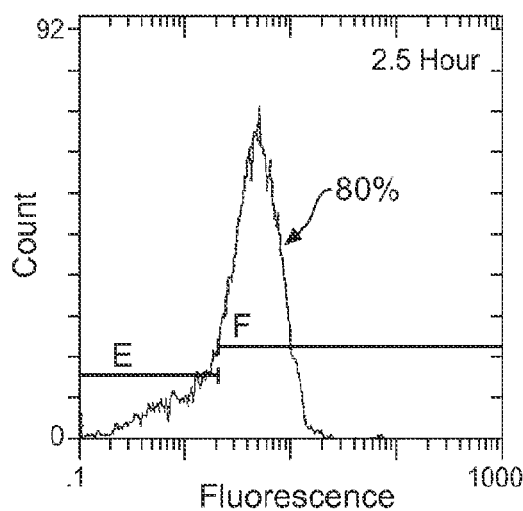
FIG. 4C is a graphical representation of a count, or number of cells, versus relative fluorescence associated with the detection of enzymatic activity of a caspase-3 enzyme in live cells via flow cytometry, using a nucleic acid dye-based substrate (Substrate No. 19, at 10 µM) for the caspase-3 enzyme that was incubated for 15 minutes with Jurkat calls that had been induced with staurosporine (at 1 µM) for 2.5 hour, as further described in relation to Examples 10 and 54.
Figure 4D:
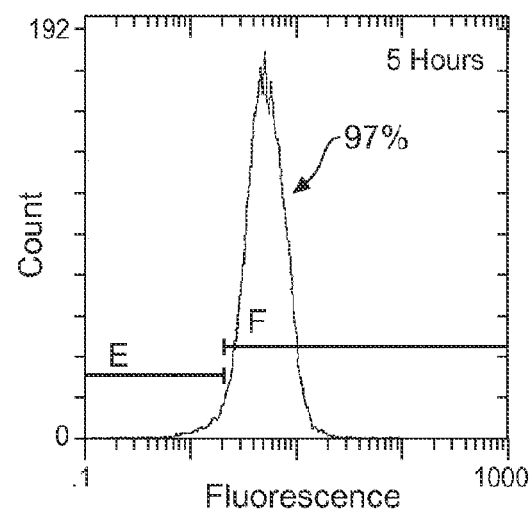
FIG. 4D is a graphical representation of a count, or number of cells, versus relative fluorescence associated with the detection of enzymatic activity of a caspase-3 enzyme in live cells via flow cytometry, using a nucleic acid dye-based substrate (Substrate No. 19, at 10 µM) for the caspase-3 enzyme that was incubated for 15 minutes with Jurkat calls that had been induced with staurosporine (at 1 µM) for 5 hour, as further described in relation to Examples 10 and 54.
Figure 5C:
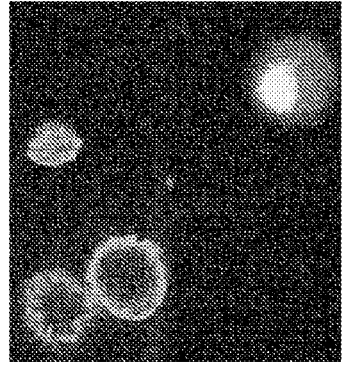
FIG. 5C is a confocal fluorescent image of apoptotic Jurkat cells (previously induced with staurosporine) that were incubated successively with a substrate (Substrate No. 19, at 10 µM) for a caspase-3 enzyme for 15 minutes and Texas Red-Annexin V for 15 minutes, as further described in relation to Examples 10 and 55.
Figure 5F:
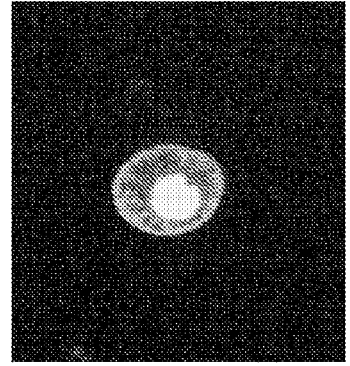
FIG. 5F is a confocal fluorescent image of apoptotic Jurkat cells (previously induced with staurosporine) that were incubated successively with a substrate (Substrate No. 19, at 10 µM) for a caspase-3 enzyme for 15 minutes and Texas Red-Annexin V for 15 minutes, as further described in relation to Examples 10 and 55.
Figure 5B:
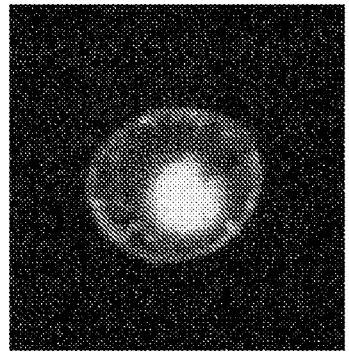
FIG. 5B is a confocal fluorescent image of apoptotic Jurkat cells (previously induced with staurosporine) that were incubated successively with a substrate (Substrate No. 19, at 10 µM) for a caspase-3 enzyme for 15 minutes and Texas Red-Annexin V for 15 minutes, as further described in relation to Examples 10 and 55.
Figure 5E:
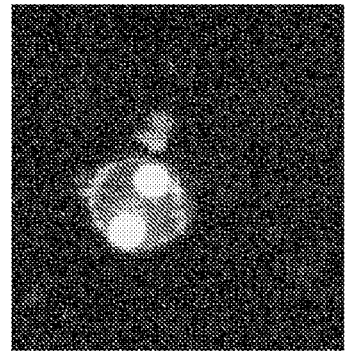
FIG. 5E is a confocal fluorescent image of apoptotic Jurkat cells (previously induced with staurosporine) that were incubated successively with a substrate (Substrate No. 19, at 10 µM) for a caspase-3 enzyme for 15 minutes and Texas Red-Annexin V for 15 minutes, as further described in relation to Examples 10 and 55.
Figure 5A:
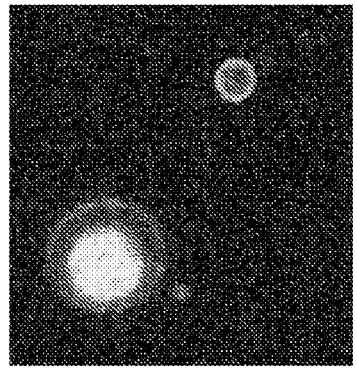
FIG. 5A is a confocal fluorescent image of apoptotic Jurkat cells (previously induced with staurosporine) that were incubated successively with a substrate (Substrate No. 19, at 10 µM) for a caspase-3 enzyme for 15 minutes and Texas Red-Annexin V for 15 minutes, as further described in relation to Examples 10 and 55.
Figure 5D:
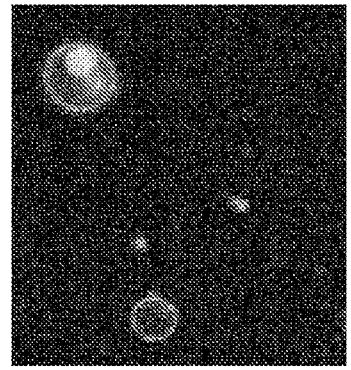
FIG. 5D is a confocal fluorescent image of apoptotic Jurkat cells (previously induced with staurosporine) that were incubated successively with a substrate (Substrate No. 19, at 10 µM) for a caspase-3 enzyme for 15 minutes and Texas Red-Annexin V for 15 minutes, as further described in relation to Examples 10 and 55.

In this example, nucleic acid dye-based caspase-3 substrates were assayed in the presence of caspase-3 and dsDNA by monitoring the fluorescence increase. In one example, Substrate No. 19 (10 µM) was incubated with caspase-3 (0.1 unit/mL) (Biovision Inc., Mountain View, Calif.) and salmon sperm dsDNA (3.3 µg/mL) in a caspase assay buffer (100 µL; HEPES buffer (50 mM, pH 7.4), NaCl (100 mM), EDTA (1 mM), CHAPS (0.1%), DTT (10 mM), PMSF (1 mM) and glycerol (10%)) in a well of a black 96-well plate. The plate was then placed in a SpectraMax Germini XS fluorescence microplate reader (Molecular Devices Corp., Sunnyvale, Calif.), with the excitation wavelength set at 485 nm and emission collection wavelength set at 530 nm, to measure the fluorescence signal over time, as shown in FIG. 3. The data demonstrates that Substrate No. 19 is a substrate for caspase-3 enzyme.

Example 54

Detection of Caspase-3 Activity in Live Cells by Flow Cytometry

In this example, Jurkat cells were used to test whether Substrate No. 19 may be used to detect caspase-3 activity, or a lack thereof, within live cells by generating a nucleic acid dye that forms fluorescence upon binding to DNA. A flask of Jurkat cells were induced with staurosporine (1 µM) for apoptosis. Aliquots of the induced Jurkat cells were taken at 1 hour, 2.5 hours and 5 hours after induction, respectively, and aliquots of uninduced Jurkat cells, which served as negative controls, were taken at the same times. Substrate No. 19 was added to each Jurkat cell culture medium to give a final concentration of 10 µM and each resulting medium was allowed to incubate for 15 minutes before undergoing flow cytometry analysis using the FL1 channel for green fluorescence. The results, shown in FIG. 4, show that the amount of staurosporine stimulation time strongly correlates with the percentage of caspase-3-positive cells identified by Substrate No. 19. For example, a stimulation time of 1 hour, 2.5 hours and 5 hours was associated with a 10%, 80% and 97% caspase-3-positive cell identification, respectively, as may be seen in the representations B, C and D of FIG. 4, respectively. One hour of staurosporine induction was required for Substrate No. 19 to reliably detect the presence of caspase-3-positive cells. Detection of intracellular caspase-3 activity via Substrate No. 19 is possible after only 15 minutes of incubation time, without necessitating cell destruction. Thus, it may be possible to continuously monitor enzymatic activity over more or less the entire course of cellular life via an enzyme substrate such as Substrate No. 19.

In this example, Jurkat cells were similarly used to evaluate DEVD-R110 (Biotium Inc., Hayward, Calif.), where DEVD is associated with SEQ ID NO: 1, a sensitive fluorogenic caspase-3 substrate that detects caspase-3 only after cell lysis. Aliquots of induced and uninduced Jurkat cells, were taken at the same intervals described above, lysed and then incubated with DEVD-R110 (where DEVD is associated with SEQ ID NO: 1) to confirm the presence or the absence of caspase-3 activity. Two hours of staurosporine induction were required for DEVD-R110 (where DEVD is associated with SEQ ID NO: 1) to detect the presence of caspase-3-positive cells (data not shown). Detection of intracellular caspase-3 activity via DEVD-R110 (where DEVD is associated with SEQ ID NO: 1) calls for cell destruction of the cells in order to access the enzyme residing within the cells. It may be possible to obtain a snap shot of intracellular enzyme activity via an enzyme substrate such as DEVD-R110 (where DEVD is associated with SEQ ID NO: 1). The differences between the results associated with Substrate No. 19 and DEVD-R110 (where DEVD is associated with SEQ ID NO: 1) suggest that the former may have some advantages relative to the latter.

Example 55

Detection of Caspase-3 Activity in Live Cells by Fluorescence Microscopy

Substrate No. 19 (10 µM) was incubated for 15 minutes with Jurkat cells that had been induced for 4 hours with staurosporine (1 µM). Separately, Substrate No. 19 (10 µM) was incubated for 15 minutes with uninduced Jurkat cells, which served as a negative control. For each of the cell cultures, cells ($1\times10^5$) were taken, pelleted and then resuspended in Annexin V binding buffer (100 µL; HEPES buffer (10 mM, pH 7.4), NaCl (140 mM) and $CaCl_2$ (2.5 mM)) in a tube, whereupon Texas Red-conjugated Annexin V (5 µL, 50 µg/mL) (Biotium Inc., Hayward, Calif.) was added to each tube. After 15 minutes of incubation at room temperature, a cell culture (5 µL) of the induced cells or the uninduced cells was spotted onto a slide, which was then mounted with a coverslip and sealed with nail polish. The cells were examined with a 510 Meta UV/Vis confocal microscope. Distinctive populations of fluorescently-labeled cells were observed, as may be seen in the images of FIG. 5, as follows: cells with only green fluorescence in cellular nuclei; cells with only red fluorescence on a cytoplasmic membrane; and cells with green fluorescence in cellular nuclei and red fluorescence on a cytoplasmic membrane. The green fluorescence is indicative of nuclear DNA staining by the nucleic acid dye that is formed from substrate cleavage via caspase-3. The red fluorescence is indicative of the staining of phosphatidylserine (PS) by the Texas Red-conjugated Annexin V, a fluorescent stain that is used to identify apoptotic cells. The staining pattern shows that the amount of PS present on the cell membranes and the amount of caspase-3 activity are not necessarily correlated, as is indicative of a heterogeneous population of apoptotic cells.

Example 56

DNA Titration of Compound No. 21 and Compound No. 23

Figure 6:
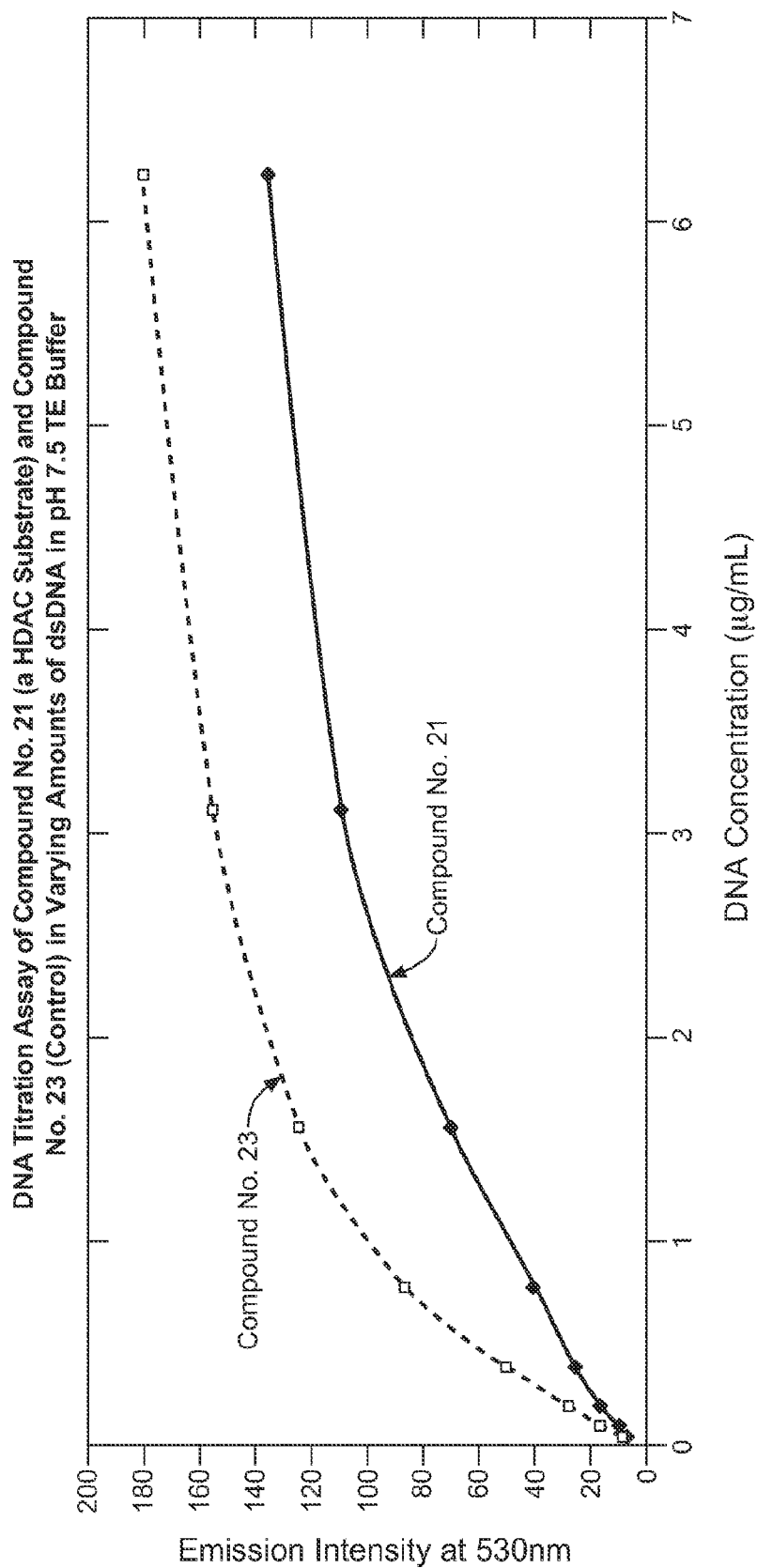
FIG. 6 is a graphical representation of relative fluorescence emission intensity versus dsDNA concentration (µg/mL), or a DNA titration, of a nucleic acid dye-based substrate (Compound No. 21, at 1 µM in TE buffer) for a histone deacetyltransferase (HDAC) enzyme and a control compound (Compound No. 23, at 1 µM in TE buffer), as further described in connection with Examples 23, 25 and 56.

DNA titrations of Compound No. 21, a nucleic acid dye-based HDAC substrate, and Compound No. 23, a control associated with Compound No. 21, were titrated with varying amounts of calf thymus dsDNA in the manner generally described above in relation to Example 52. The titration curves for substrate and the control are shown in FIG. 6. The data shows that the substrates are relatively insensitive to the presence of DNA over a wide DNA concentration range, while the controls, the enzymatically cleaved products of the substrates, are fluorescently responsive to the amount of DNA present.

Example 57

Liposome Titrations of Compound No. 44 and Compound No. 46

A stock solution (5 mM) of Compound No. 44, a membrane dye-based caspase-3 substrate, was prepared by dissolving Compound No. 44 in deionized water. A stock solution (5 mM) of Compound No. 46, the enzymatic cleavage product of Compound No. 44, was prepared by dissolving Compound No. 46 in Di-$H_2O$. A liposome stock solution was prepared by suspending 1,2-dioleyl-sn-glycero-3-phosphocholine (DOGPC) (Avanti Polar Lipids, Inc., Alabaster, Ala.) in a liposome buffer (2.5 mg/mL; pH 7.5; HEPES buffer (10 mM), NaCl (150 mM), $CaCl_2$ (2 mM) and $MgCl_2$ (2 mM)) and then sonicating the resulting suspension for 30 minutes. A solution of either Compound No. 44 or the control Compound No. 46 in the liposome buffer was prepared and the resulting solution (50 µM) was titrated with varying amounts of the liposome stock solution. Fluorescence signals associated with various such solutions were recorded on a SpectraMax Germini XS fluorescence microplate reader (Molecular Devices Corp., Sunnyvale, Calif.). Fluorescence readings associated with the substrate, Compound No. 44, or the control, Compound No. 46, were plotted in relation to the concentration of liposomes, as may be seen in FIG. 7. The membrane dye-based substrate, Compound No. 44, appeared to be relatively unresponsive to the change in liposome concentration, while the control, Compound No. 46, the enzymatic cleavage product of the substrate, appeared to be responsive to the change in liposome concentration, with the fluorescence intensity increasing as the liposome concentration increased. The data indicates that the substrate is nonfunctional as a membrane dye, while the enzymatically cleaved product of the substrate is a fully functional membrane dye that becomes fluorescent upon partitioning into membranes.

Figure 8:
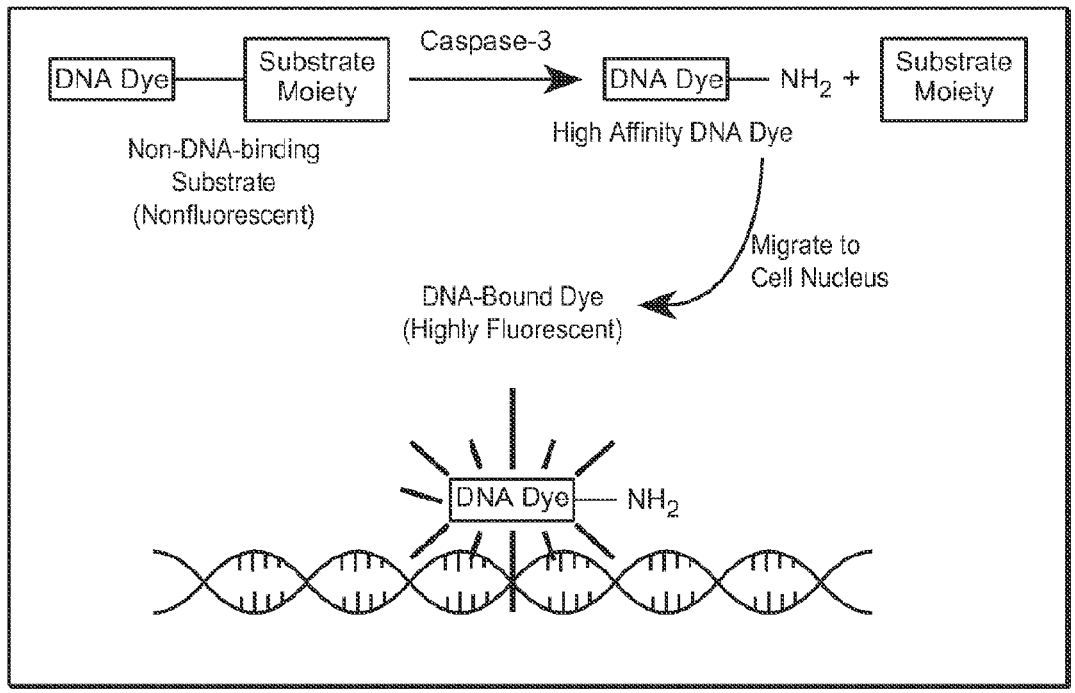
FIG. 8 is a schematic illustration of an interaction between an enzyme substrate, a nucleic acid dye-based substrate for a caspase-3 enzyme, and an enzyme, the caspase-3 enzyme, that results in an enzymatic cleavage that brings about fluorescence.
Figure 9:
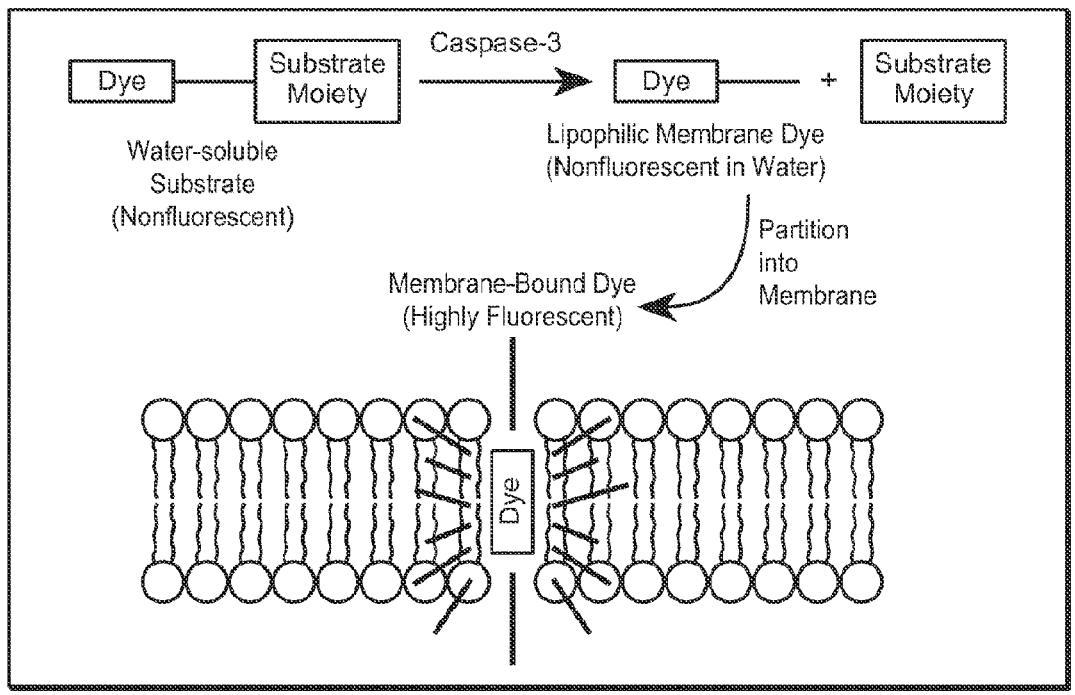
FIG. 9 is a schematic illustration of an interaction between an enzyme substrate, a membrane dye-based substrate for a caspase-3 enzyme, and an enzyme, the caspase-3 enzyme, that results in an enzymatic cleavage that brings about fluorescence.

An enzyme substrate of the invention may be used to detect the presence of an enzyme via fluorescence. FIGS. 8 and 9 provide schematic illustrations of examples of such use of enzyme substrates, which employ various biomolecules. As shown, an enzyme may be used to interact with an enzyme substrate to produce a functional dye, and a partner molecule, partner biomolecules, and/or an assembly of partner molecules may be used to interact with that functional dye to produce fluorescence. The presence or absence of fluorescence may be used as an indicator of enzyme presence or absence, respectively. Fluorescence detection may thus be employed to evaluate enzymatic activity.

Merely by way of example, an enzyme, such as caspase-3, for example, may be used to cleave a nucleic acid dye-based capase-3 substrate of the invention, as schematically illustrated in FIG. 8. The cleavage may result in a relatively or fully functional nucleic acid-binding dye that may be fluorogenic or nonfluorescent. A partner molecule, such as a DNA molecule, for example, may be used to bind to the enzymatically released nucleic acid-binding dye to form a complex of sufficiently detectable to high fluorescence. Any fluorescence generated by the complex may then be detected. Further, merely by way of example, an enzyme, such as caspase-3, for example, may be used to cleave a membrane-based caspase-3 substrate of the invention, as schematically illustrated in FIG. 9. The cleavage may result in a relatively or fully functional membrane dye that may be fluorogenic or nonfluorescent. A partner molecule or partner molecules, such as an assembly of lipid molecules, for example, may be used to enable the enzymatically released membrane dye to partition into the assembly. Merely by way of example, the assembly of lipid molecules may be a membrane and the partition of the dye may be into the membrane, as schematically illustrated in FIG. 9. Upon this partition, fluorescence may be generated and detected.

An enzyme substrate of the invention may have at least two capabilities or functionalities, one being the detection of an enzyme and another being the staining of a biomolecule or biomolecules. Such an enzyme substrate may be referred to herein as a biofunctional enzyme substrate. A bifunctional enzyme substrate of the invention may be useful in the detection of intracellular enzyme activity in live cells. This detection may be of interest because the presence or absence of enzyme activity may be accompanied by other biological change(s) within cells. An enzyme substrate of the invention may thus be useful in the detection of the enzyme activity as well as other biological event(s) within cells, such as a simultaneous biological event, for example.

Merely by way of example, an enzyme substrate of the invention may be useful in the study of apoptosis. Apoptosis, also called programmed cell death, is a normal physiological process that occurs in the development of embryos and in the maintenance of tissue homeostasis. Improperly regulated apoptosis can lead to several pathological conditions, including cancer and neurodegenerative diseases. (Reed et al., *Curr. Opin. Biotechnol.* 11, 586 (2000); Wellington et al., *Clin. Genet.* 57, 1 (2000); and Loww et al., *Carcinogenesis* 21, 485 (2000)). Apoptosis is regulated via the activation of enzymes called caspases, one of which is the caspase-3 enzyme shown in FIGS. 8 and 9. Apoptotic cells may be characterized by caspase activation and other intracellular event(s), such as the condensation of chromatin, the cleavage of nuclear DNA, nuclear blebbing, the shrinking of cell cytoplasm and organelles, and the loss of mitochondrial membrane potential, for example. A nucleic acid dye-based caspase substrate of the invention may be useful to detect caspase activity and to monitor change in the cell nucleus, as may be characteristic of apoptotic cells. (See Example 10, Substrate No. 19, and FIG. 5, for example.) A cytoplasmic membrane-based caspase substrate of the invention may be useful to detect the caspase activity and to monitor of cytoplasm shrinkage, as may be characteristic of apoptotic cells. (See Example 33, Substrate No. 47.)

An enzyme substrate of the invention may have a variety of other useful properties and uses. Merely by way of example, an enzyme substrate may be such that a fluorescent signal generated in response to enzyme activity associated with the substrate may be retained well within a cell. For example, the enzymatic product of the substrate may fluorescently and actively bind to an internal component of the cell. The retention of a fluorescence signal in this manner facilitates the intracellular detection of enzyme activity in live cell studies. Live cell studies may be of interest (relative to studies based on cell lysates, for example) because they permit continuous monitoring of the cells of interest and preserve the integrity of the overall cellular functions.

An enzyme substrate of the invention may comprise any of a variety of functional dyes having excitation and emission wavelengths that span the entire visible spectrum and extend into the near infrared spectral region. (See the wavelengths shown in Tables 2, 3, 4, 5, 6 and 7, for example.) One or more enzyme substrate(s) having different fluorescence wavelengths may be used to detect multiple enzyme activities within the same cell. One or more enzyme substrate(s) having different fluorescence emission wavelengths may be combined with one or more non-enzyme substrate fluorescent probe(s) having still different fluorescence emission wavelengths to image or to detect multiple cellular targets at the same time.

At least some of the enzyme substrates of the invention may be advantageous by virtue of their relatively long excitation and emission wavelengths. Merely by way of example, a biological sample and/or a vessel containing a biological sample may emit blue fluorescence when excited by a UV light. A fluorescent dye with an excitation wavelength and an emission wavelength of about 450 nm or more may be useful in biological imaging associated with such a sample or vessel to reduce or to minimize background fluorescence from the sample or the vessel, for example. Merely by way of example, in a biological application, a fluorescent dye having an excitation wavelength and an emission wavelength of about 470 nm or more may be usefully employed to reduce or to minimize background fluorescence. In general, an enzyme substrate of the invention may comprise a functional dye having an excitation wavelength and an emission wavelength of about 480 nm or more, as demonstrated by the information in Tables 2, 3, 4, 5, 6 and 7. For example, Substrate No. 19 of Example 10 comprises a functional dye that has an excitation wavelength of about 515 nm and emission wavelength of about 530 nm. It will be understood that an enzyme substrate comprising a functional dye associated with shorter wavelengths, such as an excitation wavelength and an emission wavelength of about 450 nm or less may be useful in any of a variety of applications, such as in a multicolor imaging experiment in which the blue fluorescence of the substrate is one of several colors useful or necessary in the experiment, merely by way of example. In general, an enzyme substrate comprising a functional dye having an excitation wavelength and an emission wavelength from about 350 nm to about 450 nm, or longer, as described above, is contemplated as being within the scope of the present invention.

At least some of the enzyme substrates of the invention may be advantageous in that they require only a single enzymatic cleavage to generate a functional dye. For example, with respect to each of Substrate No. 19 of Example 10, Substrate No. 20 of Example 19, and Substrate No. 5 of Example 26, a single enzymatic cleavage is sufficient to release a nucleic acid dye. Further by way of example, with respect to each of Substrate No. 47 of Example 33 and Compound No. 44 of Example 48, a single enzymatic cleavage is sufficient to release a membrane dye. An enzyme substrate that may be cleaved to release a functional dye via a single cleavage may accelerate the rate of enzyme detection and simplify enzyme kinetics for any quantitative analysis.

The present invention provides a number of useful enzyme substrates, such as any one or more of the following enzyme substrates: caspase, matrix metalloprotease (MMP), collagenase, gelatinase, β-lactamase, phosphatase, glycosidase, g-secretase, HCV protease, cathepsin (such as cathepsin B or cathepsin L, for example), trypsin, chymotrypsin, HIV protease, elastase, rennin protease, and phosphatidylinositol-specific phospholipase C, merely by way of example. The present invention provides a nucleic acid dye-based enzyme substrate that is suitable for intracellular detection of caspase-3 in live cells, merely by way of example. The present invention also provides a method for preparing any of the foregoing enzyme substrates and a method of using any of the foregoing substrates. Any method of using a composition of the present invention is contemplated as part of the present invention. The present invention further provides any kit comprising an enzyme substrate that may be useful. Merely by way of example, such a kit for determining apoptosis may comprise an enzyme substrate of the present invention and any other suitable, desirable or necessary component or components, such as any component useful for detection, or such as any useful detection device. Further, merely by way of example, the present invention provides a kit for detecting presence, absence, or activity of an enzyme which may comprise an inhibitor of activity of the enzyme, optionally, a promoter of activity of the enzyme, and an enzyme substrate for the enzyme, as well as a kit for determining an effect of a substance on an enzyme which may comprise an inhibitor of activity of the enzyme and an enzyme substrate for the enzyme. Any kit comprising an enzyme substrate of the present invention that has useful application is contemplated as part of the present invention.

Enzyme substrates and associated technology, including associated systems, kits, methods, and the like, of the present invention are provided. An enzyme substrate of the invention may comprise a biologically functional fluorescent dye and an enzyme-specific substrate moiety attached in such a way that the functionality of the functional dye is diminished. An enzymatic reaction may cleave at least a portion of the substrate moiety from the enzyme substrate to provide a more functional product dye. This product dye may be nonfluorescent or weakly fluorescent, in general, and relatively fluorescent, in a particular condition, such as when bound to a partner molecule, partner molecules, or an assembly of partner molecules. An enzyme substrate of the present invention may thus be useful in fluorescence detection, and/or in any of a variety of useful applications, such as the detection of enzymatic activity in a cell-free system or in a living cell, the screening of drugs, or the diagnosis of disease.

Various modifications, processes, as well as numerous structures to which the present invention may be applicable will be readily apparent to those of skill in the art to which the present invention is directed, upon review of the specification. Various references, publications, provisional and non-provisional United States or foreign patent applications, and/or United States or foreign patents, have been identified herein, each of which is incorporated herein in its entirety by this reference. Various aspects and features of the present invention have been explained or described in relation to understandings, beliefs, theories, underlying assumptions, and/or working or prophetic examples, although it will be understood that the invention is not bound to any particular understanding, belief, theory, underlying assumption, and/or working or prophetic example. Although the various aspects and features of the present invention have been described with respect to various embodiments and specific examples herein, it will be understood that the invention is entitled to protection within the full scope of the appended claims.

The invention claimed is:

1. A substrate selected from a compound having a structural formula, DYE-(B)$_m$, and a pro-enzyme substrate thereof, wherein DYE, when independent of DYE-(B)$_m$, comprises a dye selected from a biologically functional fluorescent dye and a fluorogenic dye, the dye being capable of binding to a partner biomolecule, partner biomolecules, or an assembly of partner biomolecules; wherein m is selected from 1, 2, 3, 4 and 5; and wherein each of at least one B, independently, comprises an enzyme substrate moiety that is capable of enzymatic transformation comprising cleavage of a bond involving the dye and at least one B, cleavage of a bond within at least one B, or formation of a bond involving at least one B; and wherein the dye is a phenanthrodium dye having a structural formula,

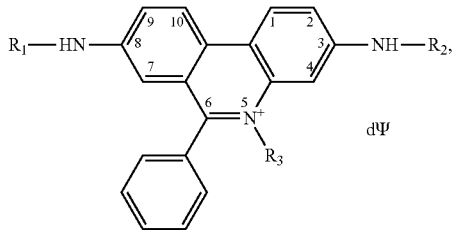

wherein:

B comprises a peptide or an amino acid;

at least one ligand of ligands R$_1$ and R$_2$ comprises B, where the C-terminal carbonyl of B is capable of forming an enzymatically cleavable peptide bond with an amino group of the dye;

if any one ligand of ligands R$_1$ and R$_2$ does not comprise B, said any one ligand comprises H;

ligand R$_3$ comprises a substituted or an unsubstituted C1 to C10 alkyl;

ψ comprises a cation selected from H+, Na+, K+, NH$_4$+, N,N,N-triethylammonium, and N,N-diisopropylethylammonium, or an anion selected from a halide, a sulfate, a phosphate, a perchlorate, a hexafluorophosphate, and a tetrafluoroborate; and d is a number of ψ sufficient to render overall charge of the substrate neutral.

2. The substrate of claim 1, wherein m is selected from 1 and 2.

3. The substrate of claim 1, wherein at least one B is a peptide.

4. The substrate of claim 1, wherein the enzymatic transformation comprises phosphorylation catalyzed by a kinase.

5. The substrate of claim 1, wherein B comprises an enzyme substrate moiety for a peptidase enzyme.

6. The substrate of claim 5, wherein B comprises an enzyme substrate moiety for an enzyme selected from a caspase, a trypsin, a chymotrypsin, an elastase, a cathepsin B, and a cathepsin L.

7. The substrate claim 1, wherein when B comprises a charged peptide, ligand R$_3$ comprises a substituted or an unsubstituted C4 to a C10 alkyl.

8. The substrate of claim 1, wherein B comprises an enzyme substrate moiety for a caspase-3 enzyme and ligand R$_2$ comprises H.

9. The substrate of claim 8, wherein B comprises Z-DEVD (SEQ ID NO: 1).

* * * * *

UNITED STATES PATENT AND TRADEMARK OFFICE
CERTIFICATE OF CORRECTION

PATENT NO. : 8,778,627 B2  
APPLICATION NO. : 13/326009  
DATED : July 15, 2014  
INVENTOR(S) : Fei Mao et al.

Page 1 of 1

It is certified that error appears in the above-identified patent and that said Letters Patent is hereby corrected as shown below:

Item (63) Related U.S. Application Data:

Delete "." after Pat. No. 8,092,784 and add --, which claims the benefit of provisional application No. 60/741,263, filed on November 30, 2005--

Signed and Sealed this  
Seventh Day of June, 2016

Michelle K. Lee  
*Director of the United States Patent and Trademark Office*